United States Patent [19]

Toner et al.

[11] Patent Number: 5,707,603
[45] Date of Patent: Jan. 13, 1998

[54] PYRIDINE COMPLEXING AGENTS AND TARGETING IMMUNOREAGENTS USEFUL IN THERAPEUTIC AND DIAGNOSTIC COMPOSITIONS

[75] Inventors: John L. Toner, Downingtown, Pa.; David A. Hilborn, Henrietta, N.Y.; Bruce J. Murray, Walworth, N.Y.; Timothy Z. Hossain, Ithaca, N.Y.; Robert A. Snow, West Chester, Pa.; Ashis K. Saha, Frazer, Pa.; Richard Philion, Averill Park, N.Y.; Clyde W. Shearman, West Chester, Pa.; Chandra Shah, Malvern, Pa.

[73] Assignee: Nycomed Imaging AS, Oslo, Norway

[21] Appl. No.: 375,276

[22] Filed: Jan. 19, 1995

Related U.S. Application Data

[63] Continuation of Ser. No. 880,117, May 7, 1992, abandoned, which is a continuation of Ser. No. 784,333, Oct. 29, 1991, Pat. No. 5,367,080, which is a continuation-in-part of Ser. No. 610,861, Nov. 8, 1990, abandoned.

[51] Int. Cl.$^6$ .......................... A61K 51/04; C07F 13/00; C07D 213/22
[52] U.S. Cl. .......................... 424/1.41; 424/1.53; 424/1.57; 424/1.65; 424/1.69; 424/1.73; 534/10; 534/14; 530/391.5; 530/391.7; 546/256; 546/257
[58] Field of Search .................. 424/9.34, 9.341, 424/9.35, 9.351, 9.361, 9.362, 1.45, 1.49, 1.53, 1.65, 1.69, 1.73, 1.41, 1.57; 534/10, 14, 15, 16; 530/391.5, 391.9; 546/256, 257

[56] References Cited

U.S. PATENT DOCUMENTS

| | | | |
|---|---|---|---|
| 4,637,988 | 1/1987 | Hinshaw et al. | 436/546 |
| 4,670,572 | 6/1987 | Hinshaw et al. | 556/1 |
| 4,745,076 | 5/1988 | Muller et al. | 436/537 |
| 4,761,481 | 8/1988 | Hale et al. | 546/296 |
| 4,767,611 | 8/1988 | Gordon | 424/9 |
| 4,794,191 | 12/1988 | Hinshaw et al. | 549/211 |
| 4,801,722 | 1/1989 | Hinshaw et al. | 549/211 |
| 4,837,169 | 6/1989 | Toner | 436/546 |
| 4,859,777 | 8/1989 | Toner | 546/256 |
| 4,960,895 | 10/1990 | Ohkara | 546/257 |
| 5,075,447 | 12/1991 | Muller et al. | 546/10 |
| 5,202,423 | 4/1993 | Kankare et al. | 530/391.5 |
| 5,204,448 | 4/1993 | Subramanian | 530/391.5 |

FOREIGN PATENT DOCUMENTS

| | | |
|---|---|---|
| 0 171 978 A1 | 2/1986 | European Pat. Off. . |
| 0 178 450 A2 | 4/1986 | European Pat. Off. . |
| 203047 | 11/1986 | European Pat. Off. . |
| 0 264 333 A2 | 4/1988 | European Pat. Off. . |
| 0 288 256 A2 | 10/1988 | European Pat. Off. . |
| 298939 | 1/1989 | European Pat. Off. . |
| 87/07955 | 12/1987 | WIPO . |
| 89/04826 | 11/1988 | WIPO . |
| 89/08263 | 9/1989 | WIPO . |
| 90/00550 | 1/1990 | WIPO . |
| 9000550 | 1/1990 | WIPO .......................... C07D 401/04 |
| 9011282 | 10/1990 | WIPO . |
| WO 91/10645 | 7/1991 | WIPO . |
| 9208494 | 5/1992 | WIPO .......................... A61K 47/48 |

OTHER PUBLICATIONS

Brechbiol et al. "Synthesis of 1-(p-Isothio cyanatobenzyl) Derivatives of DTPA & EDTA". . . *Inorg. Chem.* 25, 2772-81 (1986).
Chandler et al. (1981) J. Heterocyclic Chem. 18: 599–601.
S.E. Order et al, "Use of Isotropic Immunoglobulin in Therapy" *Cancer Research* 40, 3001-7 (Aug. 1980).
Scheinberg et al, "Tumor Imaging with Radioactive Metal Chelates Conjugated to Monoclonal Antibodies", *Science* 215, No. 19, 1511-13 (Mar. 1982).
Khan et al, "Myocardial Infarct Imaging of Antibodies to Canine Cardiac Myosin with Indium–111–Diethylenetriamine Pentaacetic Acid", *Science* 209, 295-7 (Jul. 1980).
Brechbiel et al, "Synthesis of 1-(p-Isothicyanatobanzyl) Derivities of DTPA and EDTA Antibody Labeling and Tumor Imaging Studies", *Inorg. Chem* 25, 2772-81 (1986).
Parker et al, "Implementation of Macrocycle Conjugated Antibodies for Tumor Targeting", *Pure and Applied Chem.* 61, No. 9, 1637-41 (1989).
Cox et al, "Synthesis of a Kinetically Stable Yttrium–90 Labelled Macrocycle–Antibody Conjugate", *J. Chem. Soc., Chem. Commun.* 797–8 (1989).
Craig et al, "Towards Tumor Imaging with Indium–III Labelled Macrocycle–Antibody Conjugates" *J. Chem. Soc. Chem. Comm.*, 794–6 (1989).
Mather et al, "Labelling Monoclonal Antibodies with Yttrium 90", *Eur. J. Nucl. Med.* 15, 307–12 (1989).

*Primary Examiner*—John Kight
*Assistant Examiner*—Lara C. Kelley
*Attorney, Agent, or Firm*—Fish & Richardson P.C.

[57] ABSTRACT

The invention provides targeting radioactive immunoreagents comprising a metal radionuclide ion, a complexing agent having structure A-I, as defined in the specification, and an immunoreactive group covalently bonded to the complexing agent. The present invention also provides novel complexing agents having the structure A-I, as defined in the specification. The targeting radioactive immunoreagents are particularly useful in therapeutic and diagnostic imaging compositions and methods.

27 Claims, 7 Drawing Sheets

IMMUNOCOMPETENCY, BSM (MUCIN) PLATES

LS174T TUMOR BEARING ANIMALS

PYRIDINE COMPLEXING AGENTS AND TARGETING IMMUNOREAGENTS USEFUL IN THERAPEUTIC AND DIAGNOSTIC COMPOSITIONS

This application is a continuation of U.S. application Ser. No. 07/880,117, filed May 7, 1992, now abandoned, which is a continuation of U.S. application Ser. No. 07/784,333, filed Dec. 29, 1991, now U.S. Pat. No. 5,367,080, which is a continuation-in-part of U.S. application Ser. No. 07/610,861 filed Nov. 8, 1990, now abandoned.

FIELD OF THE INVENTION

The present invention relates to novel immunoreagents and more particularly to targeting radioactive immunoreagents which find particular utility in therapeutic and diagnostic imaging compositions and methods. The present invention further relates to novel complexing agents.

BACKGROUND OF THE INVENTION

Prior to 1980, the targeting of tumor-bearing sites by radioimmunoglobulin had been demonstrated by a number of laboratories at different institutions (S. E. Order et al., "Use of Isotopic Immunoglobulin in Therapy," *Cancer Research* 40, 3001–7(August 1980)). By 1980 it was demonstrated that tumors would concentrate radiolabeled-antibodies to tumor associated antigens and that radiolabeled reagents employed allowed both diagnostic imaging of tumors, e.g., by gamma camera imaging (radioimmunoscintigraphy) and positron tomography, and therapeutic treatment, i.e., reduction in tumor size by the targeting radioactive immunoreagent.

Early targeting with radiolabeled immunoreagents was carried out with radioactive iodine. However, as noted by Scheinberg et al, "Tumor Imaging with Radioactive Metal Chelates Conjugated to Monoclonal Antibodies," *Science* 215, No. 19, 1511–13 (March 1982), iodine isotopes pose several problems, particularly with respect to scanning of tumor images. Of the three commonly available isotopic forms, only $^{123}$I has the appropriate emission characteristics for imaging and a short enough half-life to be safely used diagnostically. The gamma radiation of $^{125}$I is too weak for imaging. $^{131}$I has often been used but is undesirable because of its long half-life and high energy gamma and cytotoxic beta radiations. $^{131}$I has also been used therapeutically for large tumors, but appears ineffective in the treatment of small tumors. Moreover, rapid metabolism of radioiodinated antibodies allows incorporation of the iodine into the thyroid and active excretion of the iodine by the stomach and urinary tract. This dispersion of the radioactive iodine hinders imaging of specific tumors, since the tumors are hidden by background radiation.

In addition to tumor targeting with radioactive antibodies for diagnostic imaging and therapeutic treatment, similar targeting has been accomplished for diagnostic imaging of infarcts, specifically, myocardial infarcts, using antibodies to canine cardiac myosin [Khaw et al, "Myocardial Infarct Imaging of Antibodies to Canine Cardiac Myosin Indium-111—Diethylenetriamine Pentaacetic Acid," *Science* 209, 295–7 (July 1980)], and for imaging atherosclerosis by targeting atherosclerotic plaques. The same disadvantages in the use of radioactive iodine exist for diagnostic infarct imaging as for tumor imaging and therapeutic treatment.

It is known that $^{111}$In can be complexed with polyaminocarboxylic acids such as ethylene diaminetetraacetic acid (EDTA) and diethylenetriaminepentaacetic acid (DTPA). However, the covalent linkage of proteins (antibodies) to these complexing agents, accomplished by acylation with activated carbonyls, aromatic diazonium coupling, or bromoacetylation, is inefficient, even though the isocyanatobenzyl derivatives described by Brechbiel et al ["Synthesis of 1-(p-Isothiocyanatobenzyl) Derivatives of DTPA and EDTA. Antibody Labeling and Tumor Imaging Studies," *Inorg. Chem.* 25, 2772–81 (1986)] were created to facilitate covalent attachment of proteins with the complexing agents.

Recently, research efforts have been directed to improved antibodies (Ab's), e.g., monoclonal, specific antibodies for specific targeting, antibodies that complex or bind directly with radionuclides, preferred radionuclides and combinations thereof with antibodies and complexing agents. Some attempts have been made towards improving complexing agents.

Nonetheless, EDTA and especially DTPA and derivatives thereof have remained the prevalent complexing agents to covalently bind antibody and coordinately complex metallic radionuclides. However, the inadequacies of DTPA have been noted, for example, by Parker et al, "Implementation of Macrocycle Conjugated Antibodies for Tumor Targeting," *Pure and Appl. Chem,* 61, No. 9, 1637–41 (1989): "Conventionally the metal radionuclide has been complexed by an acyclic chelate (e.g. EDTA or DTPA) which is covalently linked to the antibody. None of the chelates is adequate because the metal tends to dissociate in vivo, . . .", and by Cox et al, "Synthesis of a Kinetically Stable Yttrium-90 Labelled Macrocycle-Antibody Conjugate", *J Chem. Soc., Chem. Commun.* 797–8 (1989): "Yttrium-90 is an attractive isotope for therapy . . . but its clinical use will be very limited because of bone marrow toxicity, resulting from acid-promoted release of $^{90}$Y from an antibody linked chelate such as diethylenetriamine-pentaacetic acid (DTPA)."

Previous attempts to develop improved complexing agents have provided materials which have their own shortcomings. For example, Craig et al "Towards Tumor Imaging with Indium-111 Labelled Macrocycle-Antibody Conjugates," *J. Chem. Soc. Chem. Commun.,* 794–6 (1989) describe macrocyclic is hexacoordinating ligands but state that "The limiting feature of this approach is that $^{111}$In labelling of the macrocycle is required before antibody conjugation. Indium binding by (4) is insufficiently fast at 37° C. for efficient radiolabeling . . . Other tribasic triazamacrocyclic ligands were screened therefore for their ability to bind indium rapidly under mild conditions (20° C., pH 5, <1h) yet still form a kinetically stable complex in vivo . . . However, only (6) proved effective when the ligand concentration was 10 µM, and under these conditions a 96% radiolabeling yield was determined (30 min, pH 5, 20° C.)."

Nevertheless, thirty minutes is still unsatisfactory. It would be highly desirable to have complexing agents superior to EDTA and DTPA which would coordinately bind preferred radionuclides such as In, Y, Sc, Ga, Ge, etc. within a few minutes, i.e., in less than about 5 minutes immediately prior to administration of the reagent to the patient, especially when a short-lived radionuclide must necessarily be generated from a longer-lived radionuclide at the time of treatment of the patient.

It should be noted that complexes of yttrium, a preferred radionuclide for therapy, tend to be less stable than those of indium [(Mather et al, "Labelling Monoclonal Antibodies with Yttrium 90," *Eur. J, Nucl. Med.,* 15, 307–312 (1989)] with respect to conventional complexes. Mather et al teach that biodistribution studies in cancer patients using radiolabeled antibodies have suggested that the in vivo stability of yttrium-labeled antibodies is not as great as that of their $^{111}$In-labelled counterparts and that these findings are supported by other recent publications in the field.

When chelating agents are covalently bonded to proteins (such as Ab's), the proteins usually are capable of accepting far more than one molecule of the chelating agent because they contain a host of amine and sulfhydryl groups through which the chelating agents are bound. It is often very important to determine how many chelating sites are bound to each protein molecule. The most convenient way to accomplish this is by spectrophotometric means. However, prior art chelating agents and chelates thereof have spectral absorptions that overlap with those of useful proteins, and an analytical determination of the number of chelating or chelated sites per molecule of protein cannot be made unequivocally by spectrophotometry since the overlapping spectral absorptions mask each other. It would thus be highly desirable to obtain chelating agents for conjugation to proteins whose spectrophotometric absorptions, and whose metal chelate spectrophotometric absorptions, do not overlap with those of the proteins to which the chelating agents are chemically bonded.

Another problem with some prior art compositions is that the chelator must be activated by a reducing agent before forming the radionuclide chelate. If the protein conjugates are to be formed prior to formation of the radionuclide chelate, then the reducing agent employed for activating the complexing agent can degrade the protein. For example, the preferred chelating agents currently used for complexing technetium (Tc) and rhenium (Re) complex to the metals via sulfur-containing groups which must be reduced with a reducing agent (dithiothreitol) to activate the chelator before forming the radionuclide chelate. If the protein conjugate containing disulfide bonds is formed prior to reduction, then the reducing agent can degrade the protein. It would be highly desirable to have chelating agents capable of forming conjugates with proteins before complexing with radionuclides.

In summary, the various currently available radiolabeled antibodies and chelating agents employed for making immunoreactive conjugates by covalently bonding a chelating agent to the immunoreactive protein, and radionuclide complexes thereof for use in diagnostic imaging and targeted therapeutics suffer from one or more of the following disadvantages: 1) toxicity; 2) dispersion of the reagent due to rapid metabolism; 3) inadequate emission characteristics; 4) inefficient covalent bonding with protein for conjugate preparation; 5) slow complexation with metals; 6) unstable metal complexation, e.g., with respect to temperature, time or pH; 7) inability to form conjugates and remain stable in storage until metal complexation is desired; 8) inability to spectrophotometrically analyze the radionuclide complex reagent; and 9) inability to complex without activation steps that degrade protein.

SUMMARY OF THE INVENTION

We have discovered targeting radioactive immunoreagents which solve the problems of the prior art discussed above. The targeting radioactive immmunoreagents of this invention comprise a metal radionuclide ion, a complexing agent which is a derivative of a pyridine, bipyridine, terpyridine, quaterpyridine, quinquepyridine, sexipyridine or phenanthroline, and an immunoreactive group covalently bonded through a protein reactive group to the complexing agent.

More particularly, in accordance with the invention, there is provided:

a targeting radioactive immunoreagent comprising a metal radionuclide ion, a complexing agent, and an immunoreactive group covalently bonded to the complexing agent, the complexing agent having the structure A-I

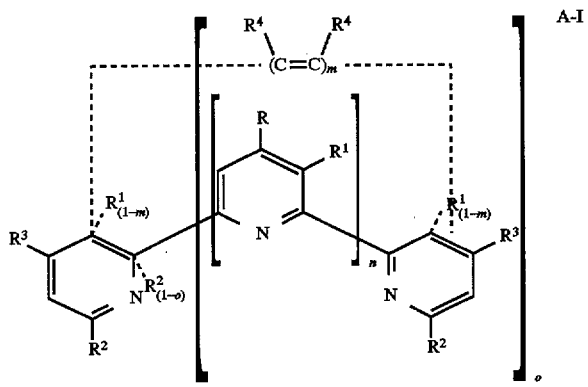

wherein

R represents hydrogen, alkyl, alkoxy, alkylthio, alkylamino, alkylformamido, aryl, aryloxy, heterocyclyl or a protein reactive group;

$R^1$ represents hydrogen, alkyl, alkoxy, alkylthio, alkylamino, alkylformamido, aryl, aryloxy, heterocyclyl or a protein reactive group;

$R^2$ represents hydroxy, carboxy, hydroxyalkyl, thioalkyl, carbonyliminodiacetic acid, methyleneiminodiacetic acid, methylenethioethyleneiminodiacetic acid, carboxyalkythioalkyl, hydrazinylidenediacetic acid, or a salt of such acids, or two $R^2$ groups, taken together, represent the atoms necessary to complete a macrocyclic ring structure containing at least one heteroatom coordinating site and at least one, preferably two, alkylene groups forming part of the ring structure;

$R^3$ represents hydrogen, alkyl, alkoxy, alkylthio, alkylamino, alkylformamido, aryl, aryloxy, heterocyclyl or a protein reactive group;

$R^4$ represents hydrogen or a protein reactive group;

n is 0, 1, 2, 3 or 4;

o is 0 or 1;

m is 0 or 1;

provided that at least one of n and m is 0 and at least one of R, $R^1$, $R^3$ and $R^4$ is a protein reactive group The pyridines have the structure A-II

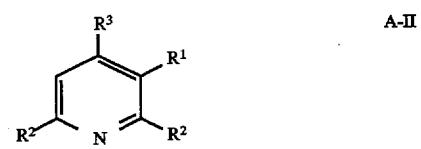

wherein $R^1$, $R^2$ and $R^3$ are as defined above.

The bipyridines, terpyridines, quaterpyridines, quinquepyridines and sexipyridines have the structure A-III

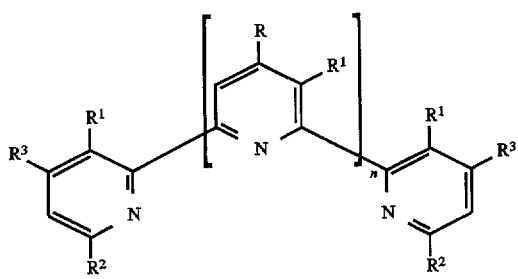

A-III wherein R, $R^1$, $R^2$ and $R^3$ are as defined above and n is 0, 1, 2, 3 or 4.

The phenanthrolines have the structure A-IV

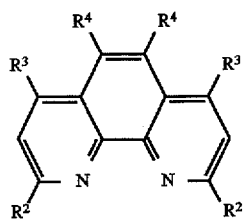

A-IV wherein $R^2$, $R^3$ and $R^4$ are as defined above.

This invention provides novel terpyridines, quaterpyridines, quinqepyridines, and sexipyridines having the structure A-I. Preferred terpyridines of the invention have the structure A-III above wherein n=1, and R is

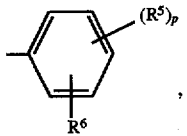

wherein $R^5$ is alkoxy or alkyl, p is 0,1,2,3 or 4 and $R^6$ is a protein reactive group.

This invention further provides novel phenanthrolines preferably having the structure A-IV above wherein at least one $R^4$ is a protein reactive group.

This invention also provides therapeutic and diagnostic compositions comprising the above-described targeting radioactive immunoreagent.

This invention further provides a method for diagnostic imaging a site in a patient comprising a) administering to the patient an effective amount of the above-described radioactive immunoreagent capable of targeting the site, and b) imagewise activating a radiation-sensitive element or device, such as, for example, a film or electronic sensor, with the radiation emitted from the targeted site.

A method for treating disease sites in a patient according to this invention comprises administering to the patient or a specimen from the patient an effective amount of a therapeutic composition comprising the above-described radioactive immunoreagent capable of targeting the site and a pharmaceutically acceptable carrier therefor.

It is an advantageous feature of this invention that the described targeting radioactive immunoreagents containing yttrium exhibit lower radiation toxicity, when compared to radioactive immunoreagents prepared with other yttrium chelators.

It is also an advantageous feature that the targeting immunoreagents of this invention are not rapidly metabolized and do not deleteriously disperse.

It is another advantageous feature that the described complexes efficiently form covalent bonds with proteins and other biological molecules.

Yet another advantageous feature of this invention is that the described immunoreagents exhibit good emission characteristics and are readily subject to spectrophotometric analysis.

Additionally, protein conjugates of the complexing agents can be formed and stored until metal complexation is desired, and complexation can be accomplished without activation steps that degrade protein.

Moreover, the complexing agents rapidly complex with metals, and the resulting chelates exhibit excellent stability with respect to time, temperature and pH.

Other advantageous features of this invention will become readily apparent upon reference to the following description of the preferred embodiments, when read in light of the accompanying drawings.

BRIEF SUMMARY OF THE INVENTION

FIG. 3 depicts the results of a biodistribution study of B72.3-TMT-$^{111}$In, a radioactive immunoreagent of the invention, and B72.3-DTPA-$^{111}$In.

DESCRIPTION OF THE PREFERRED EMBODIMENTS

Figure 1:
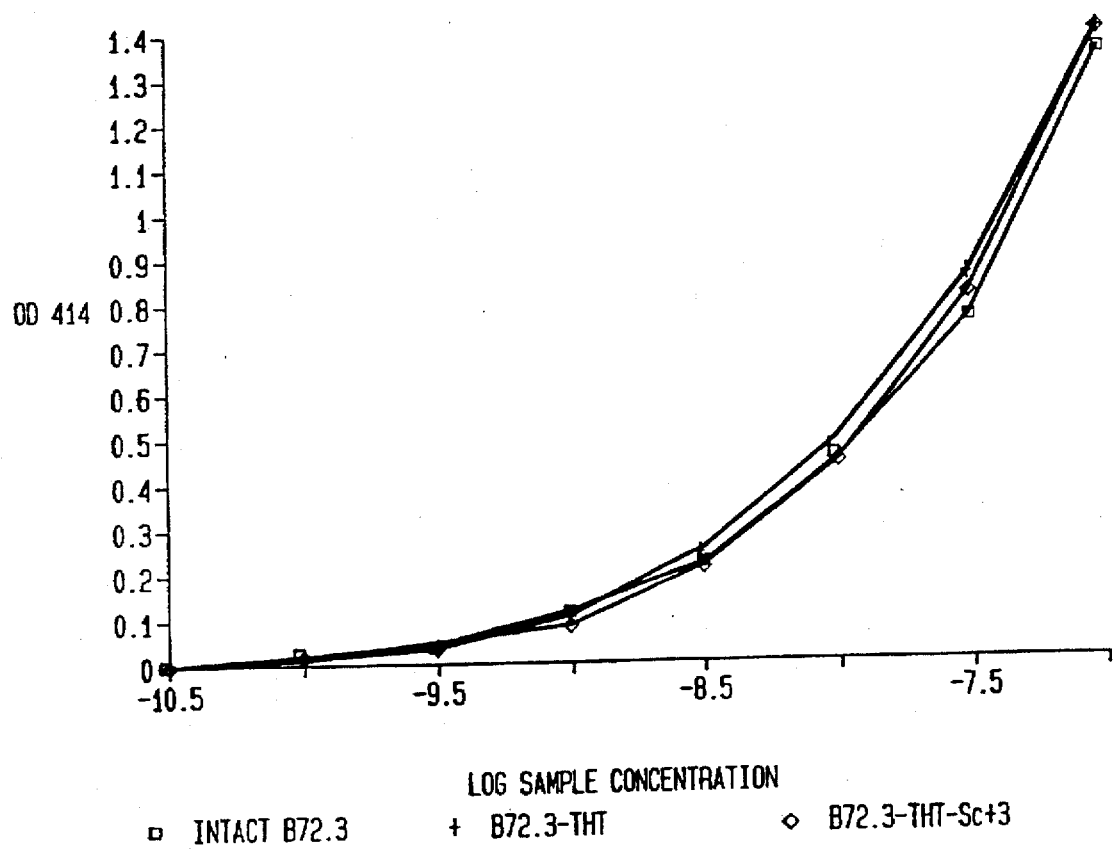
FIG. 1 depicts immunocompetency assays of B72.3-THT-$Sc^{+++}$, a radioactive immunoreagent of this invention, a B72.3-THT conjugate and unmodified B72.3 .

The description which follows primarily concerns usage of the targeting radioactive immunoreagents in therapeutic and diagnostic imaging compositions and methods. In addition, the targeting radioactive immunoreagents are useful as diagnostic reagents, for example, radioimmunoelectrophoresis reagents.

The immunoreagents of this invention comprise a metal radionuclide ion, a complexing agent, and an immunoreactive group covalently bonded to the complexing agent through a protein reactive group.

The complexing agent is a derivative of a pyridine, bipyridine, terpyridine, quaterpyridine, quinquepyridine, sexipyridine or phenanthroline, preferably having the structural formula A-I recited in the Summary above.

Each R in formula A-I independently is hydrogen; straight or branched alkyl, preferably containing from 1 to about 20 carbon atoms such as methyl, ethyl, propyl, isopropyl, butyl, s-butyl, t-butyl, 2-ethylhexyl, decyl, hexadecyl, octadecyl, etc.; alkoxy, the alkyl portion of which contains from 1 to about 20 carbon atoms as described for R above; alkylthio, the alkyl portion of which contains from 1 to about 20 carbon atoms as described for R above; alkylamino, the alkyl portion of which contains from 1 to about 20 carbon atoms as described for R above; alkylformamido, the alkyl portion of which contains from 1 to about 20 carbon atoms as described for R above; substituted or unsubstituted aryl, preferably containing from about 6 to 20 carbon atoms such as phenyl, naphthyl, phenanthryl, nitrophenyl, hydroxyphenyl, aminophenyl, hexadecylaminophenyl, octadecylaminophenyl, tolyl, xylyl, methoxyphenyl, 3-amino-4-methoxyphenyl, 4-methoxy-3-(N-methylhydrazinothioformamido)phenyl, 3-isocyanato-4-methoxyphenyl, 3-isothiocyanato-4-methoxyphenyl, methylthiophenyl, carboxyphenyl and alkylaryl such as alkylphenyl, the alkyl portion of which contains from 1 to about 20 carbon atoms as described for R above; aryloxy, the aryl portion of which contains from 6 to about 20 carbon atoms as described for R above; a substituted or unsubstituted heterocycly, preferably containing 5 or 6 nuclear carbon and heteroatoms such as N, S, P or O, such as pyridyl, methylpyridyl, nitropyridyl, methoxypyridyl, oxazolyl, imidazolyl, pyrazolyl and quinolyl; or a protein reactive group. In especially preferred embodiments, R is a 4-alkoxy-3-aminophenyl or a 4-alkoxy-3-isothiocyanato phenyl group.

Each $R^1$ is independently selected from the groups specified for R. $R^1$ preferably represents hydrogen or a protein reactive group.

Each $R^2$ is independently selected from hydroxy; carboxy; hydroxyalkyl, the alkyl portion of which preferably contains from 1 to 4 carbon atoms, such as hydroxymethyl; carbonyliminodiacetic acid, [—CON(CH$_2$COOH)$_2$]; methyleneiminodiacetic acid, [—CH$_2$N(CH$_2$COOH)$_2$]; methylenethioethyleneiminodiacetic acid [—CH$_2$SCH$_2$CH$_2$N(CH$_2$COOH)$_2$]; carboxyalkythioalkyl, the alkyl portions of which independently contain from 1 to 4 carbon atoms, such as —CH$_2$CH$_2$SCH$_2$CH$_2$COOH; 1-hydrazin-2-ylidenediacetic acid, such as 1-hydrazin-2-ylidenediacetic acid, [—NHN(CH$_2$COOH)$_2$] and 1-methyl-1-hydrazin-2-ylidenediacetic acid, [—N(CH$_3$)N(CH$_2$COOH)$_2$]; and 2,6-dicarboxy-4-piperidinyl or the salts of such acids, including, for example, metal salts of such acids formed from such metals as Na, K, Li, etc., and ammonium salts such as ammonium, tetraethylammonium, and tetramethylammonium salts. Alternatively, two $R^2$ groups, taken together, represent the atoms necessary to complete a macrocyclic ring structure containing (a) at least one heteroatom coordinating site for ions, and (b) at least one, preferably two, alkylene groups forming part of the ring structure. The macrocyclic ring-forming groups can be a heteroatom group substituted alkylene such as 2,2-bis(ethoxycarbonyl)-1,3-propylene; or heteroatom-containing groups such as oxybis (alkylene), for example oxybis(ethylene), oxybis (ethyleneoxymethylene), oxybis(ethyleneoxyethylene); alkyleneoxyalkyleneoxyalkylene, such as methyleneoxyethyleneoxymethylene; arylene-di(oxyalkylene), such as 1,4-dimethyl-5,6-phenylenebis(oxymethylene); 2,6-pyridylenebis(methyleneoxymethylene); 2-methoxy-5-methyl-1,3-phenylenebis(methyleneoxymethylene) and 1,10-phenanthrolin-2,9-ylenebis(methyleneoxymethylene); carboxymethyliminobis[(trimethylene(carboxymethyl)iminomethylene], [—CH$_2$N(CH$_2$COOH)(CH$_2$)$_3$—N(CH$_2$COOH)(CH$_2$)$_3$N(CH$_2$COOH)CH$_2$—]; carboxymethylthioethyliminobis[trimethylene (carboxymethylthioethyl)iminomethylene], [—CH$_2$N(CH$_2$CH$_2$SCH$_2$COOH)(CH$_2$)$_3$N(CH$_2$CH$_2$SCH$_2$COOH)(CH$_2$)$_3$N(CH$_2$CH$_2$—SCH$_2$COOH)CH$_2$—]; carboxymethyliminobis[ethylene(carboxymethyl)iminomethylene], [—CH$_2$N(CH$_2$COOH)CH$_2$CH$_2$N(CH$_2$COOH)CH$_2$CH$_2$N—(CH$_2$COOH)CH$_2$—]; carboxymethylthioethyliminobis[ethylene (carboxymethylthioethyl)iminomethylene], [—CH$_2$N(CH$_2$CH$_2$SCH$_2$COOH)—CH$_2$CH$_2$N(CH$_2$CH$_2$SCH$_2$COOH)CH$_2$CH$_2$N(CH$_2$CH$_2$SCH$_2$COOH)—CH$_2$—]; ethylenebis[(carboxymethyl)iminomethylene], [—CH$_2$N(CH$_2$COOH)—CH$_2$CH$_2$N(CH$_2$COOH)CH$_2$—]; carboxymethyliminobis(methylene), [—CH$_2$N(CH$_2$COOH)CH$_2$—]; or the salts of the exemplified carboxylic acid containing groups, including, for example, the metal and ammonium salts of such acids as described for $R^2$ above. In especially preferred embodiments, $R^2$ is methyleneiminodiacetic acid or a salt thereof.

Each $R^3$ is independently selected from the groups specified for R. $R^3$ preferably represents hydrogen.

Each $R^4$ is independently selected from hydrogen or a protein reactive group.

In formula A-I above, n is 0, 1, 2, 3 or 4; m is 0 or 1; and o is 0 or 1; provided that at least one of n and m is 0.

At least one of the R, $R^1$, $R^3$ and $R^4$ groups present is a protein reactive group. Preferably, no more than one of the R, $R^1$, $R^3$ and $R^4$ groups on each aromatic ring is a protein reactive group. Most preferably, only one of the R, $R^1$, $R^3$ and $R^4$ groups per molecule is a protein reactive group.

By "protein reactive group" is meant any group which can react with any functional groups typically found on or introduced into proteins. However, it is specifically contemplated that the protein reactive group can be conjugated to nonprotein biomolecules. Thus the protein reactive groups useful in the practice of this invention include those groups which can react with any biological molecule (including carbohydrates, nucleic acids and lipids) containing a reactive group, or a specific receptor-ligand interactive group, to form a linking group between the complexing agent and the immunoreactive group.

Preferred protein reactive groups can be selected from, but are not limited to: (1) A group that will react directly with the amine or sulfhydryl groups on the protein or biological molecule containing the immunoreactive group, for example, active halogen containing groups including, for example, chloromethylphenyl groups and chloroacetyl [Cl—CH$_2$CO—] groups, activated 2-leaving group substituted ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like; and other groups known to be useful in conventional photographic gelatin hardening agents; (2) A group that can react readily with modified proteins or biological molecules containing the immunoreactive group, i.e., proteins or biological molecules containing the immunoreactive group modified to contain reactive groups such as those mentioned in (1) above, for example, by partial oxidation of the protein to introduce an aldehyde or a carboxylic acid, in which case the "protein reactive group" can be selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 20 carbon atoms as described for R above. The aryl portions of the protein reactive group can contain from about 6 to about 20 carbon atoms as described for R above. (3) A group that can be linked to the protein or biological molecule containing the immunoreactive group, or to the modified protein as noted in (1) and (2) above by use of a crosslinking agent. Certain useful crosslinking agents, such as, for example, difunctional gelatin hardeners, bisepoxides and bisisocyanates become a part of, i.e., a linking group in, the protein-complexing agent conjugate during the crosslinking reaction. Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847, the disclosure of which is hereby incorporated herein by reference in its entirety, and the dication ethers of U.S. Pat. No. 4,877,724, the disclosure of which is hereby incorporated herein by reference in its entirety. With these crosslinking agents, one of the reactants must have a carboxyl group and the other an amine or sulfhydryl group. The crosslinking agent first reacts selectively with the carboxyl group, then is split out during reaction of the "activated" carboxyl group with an amine to form an amide linkage between the protein and metal complexing agents having the structure A-I above, thus covalently bonding the two moieties. An advantage of this approach is that crosslinking of like molecules, e.g., complexing agents with complexing agents, is avoided, whereas the reaction of difunctional crosslinking agents is nonselective so that unwanted crosslinked molecules are obtained. Especially preferred protein reactive groups include amino and isothiocyanato.

Especially preferred complexing agents include species 1–59 set forth below.

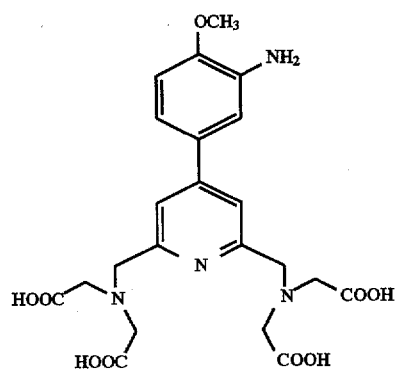

1

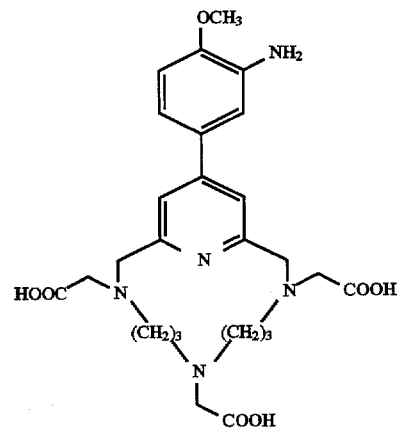

2

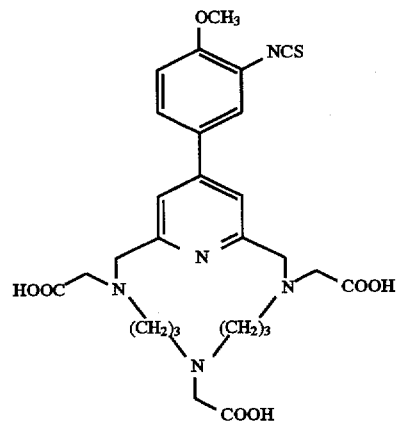

3

-continued
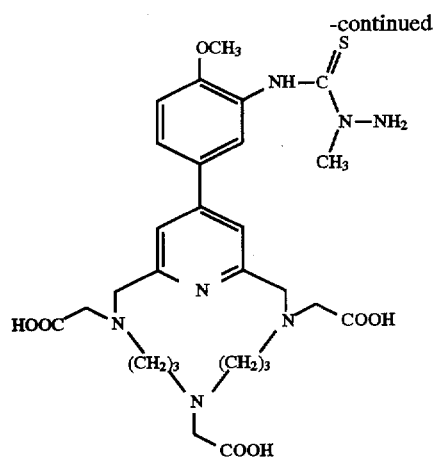
(4)
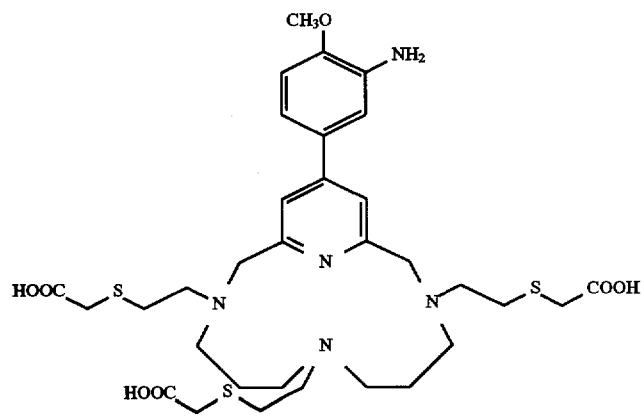
(5)
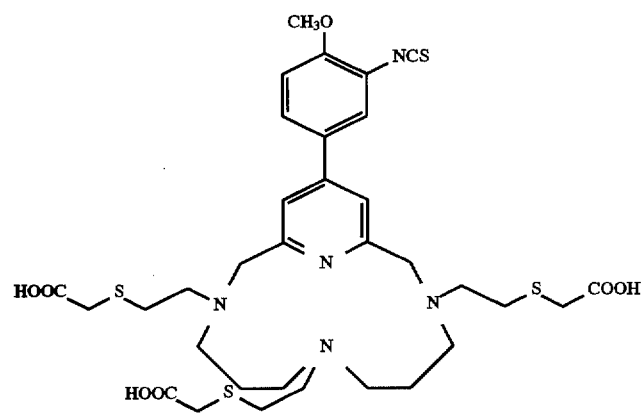
(6)
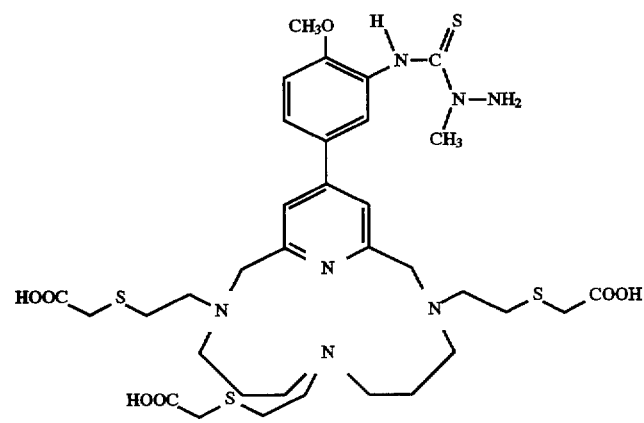
(7)

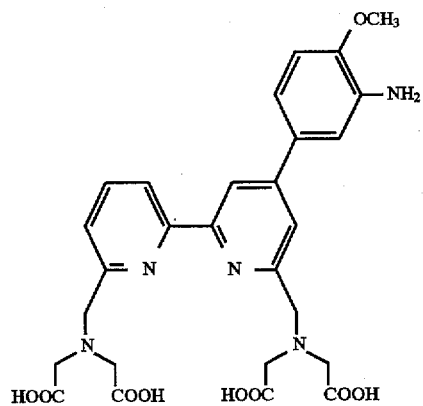
8
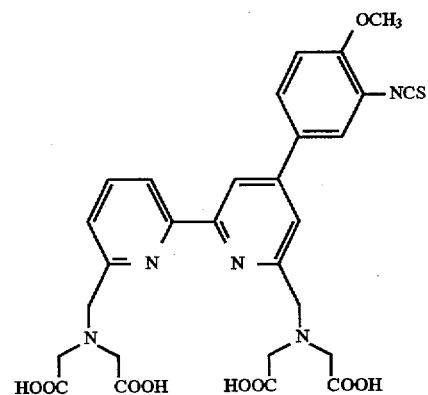
9
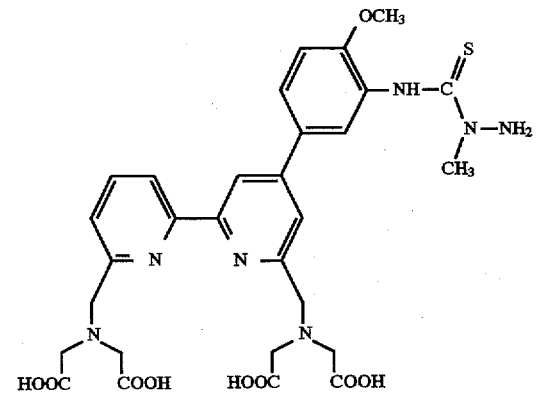
10
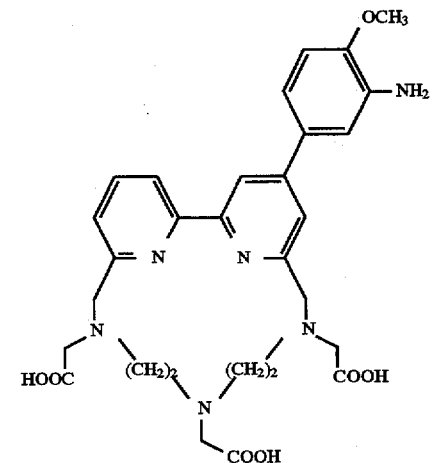
11

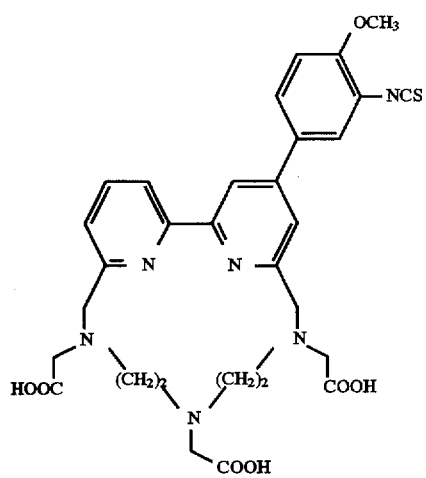
12
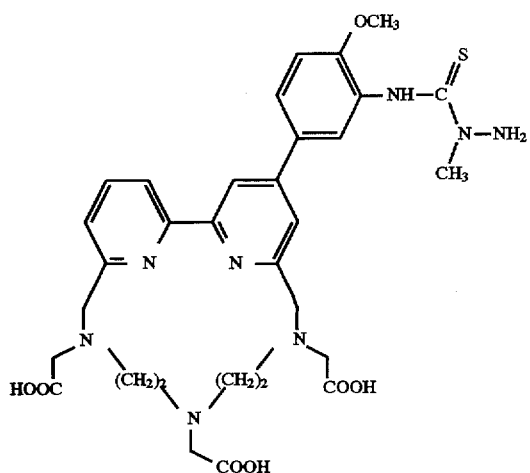
13
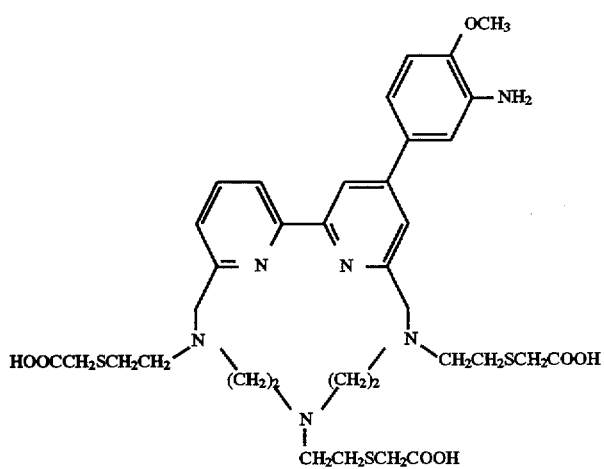
14

-continued
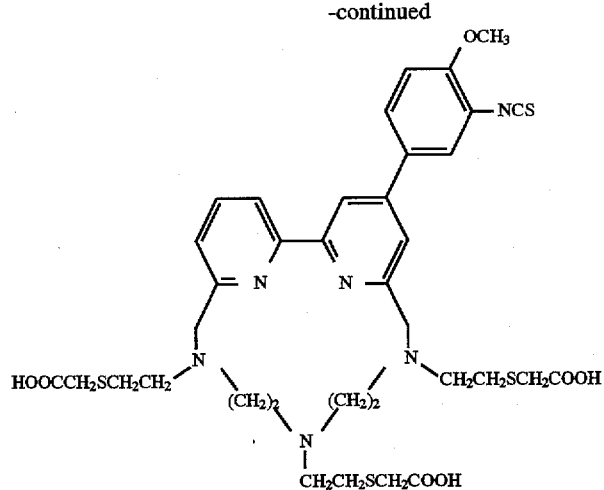
15
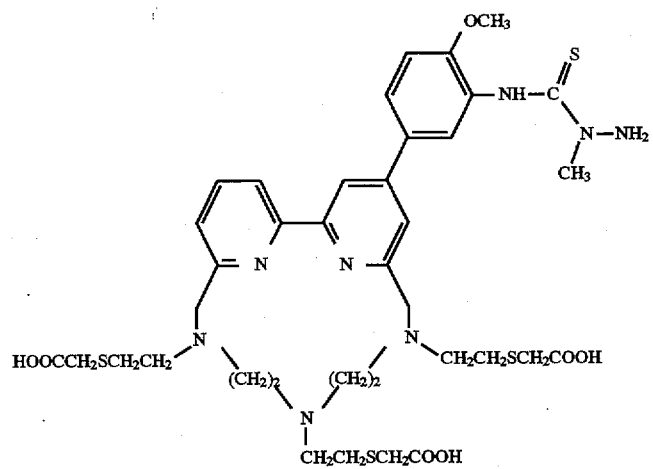
16
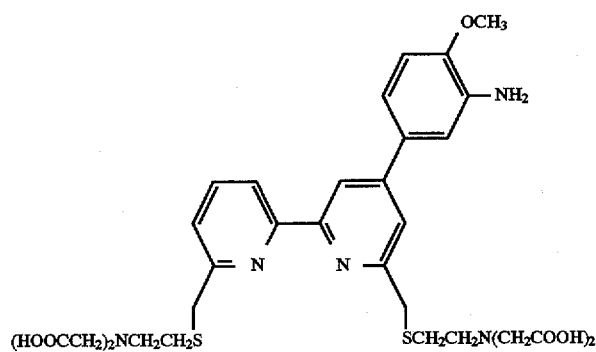
17
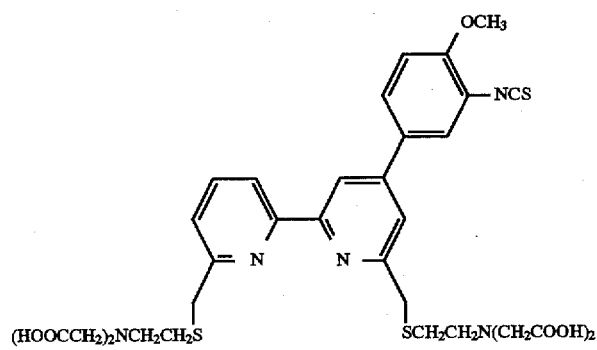
18

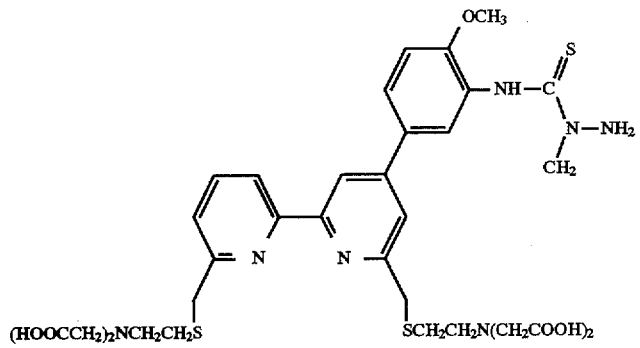
19
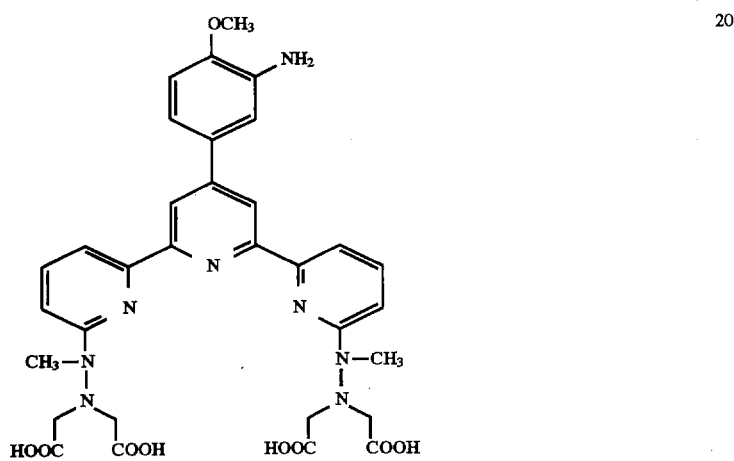
20
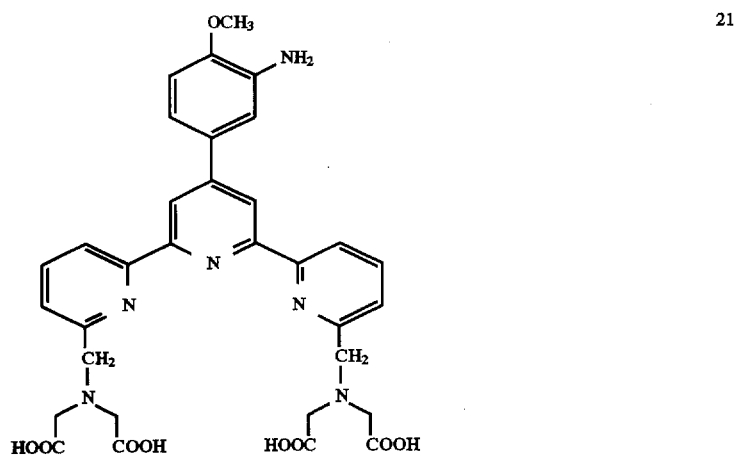
21

22
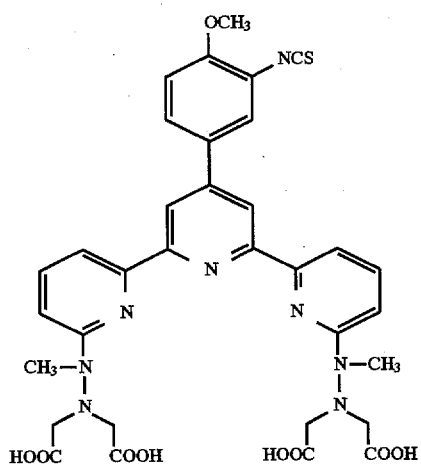
23
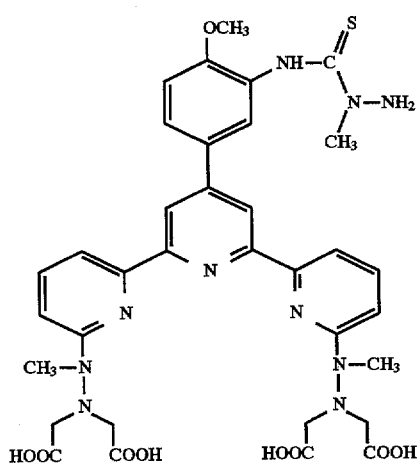
24
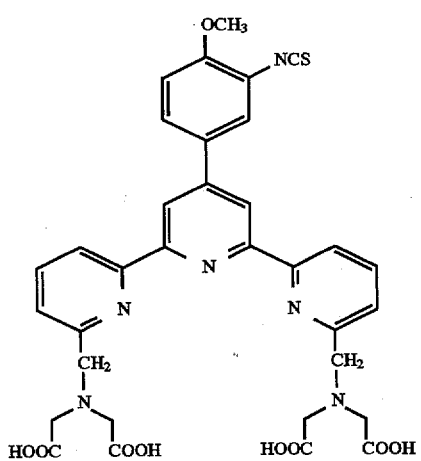

25
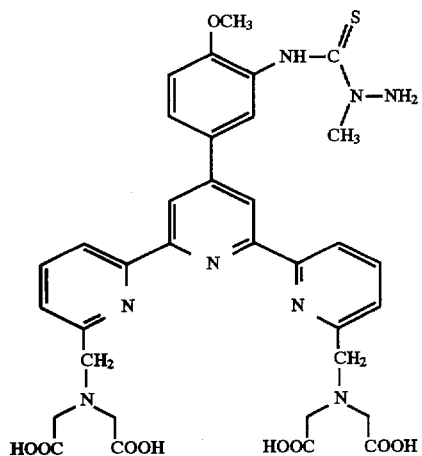
26
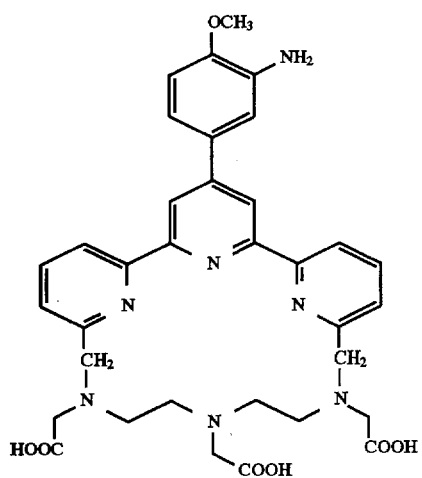
27
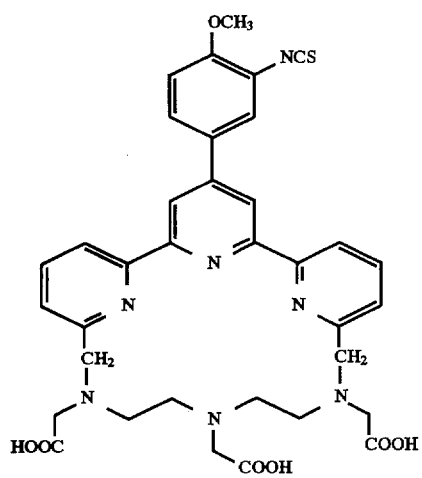

-continued
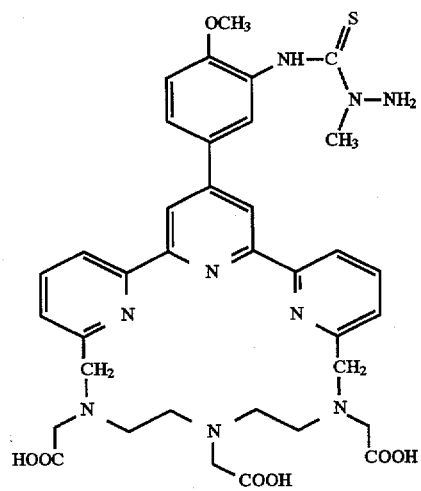
28
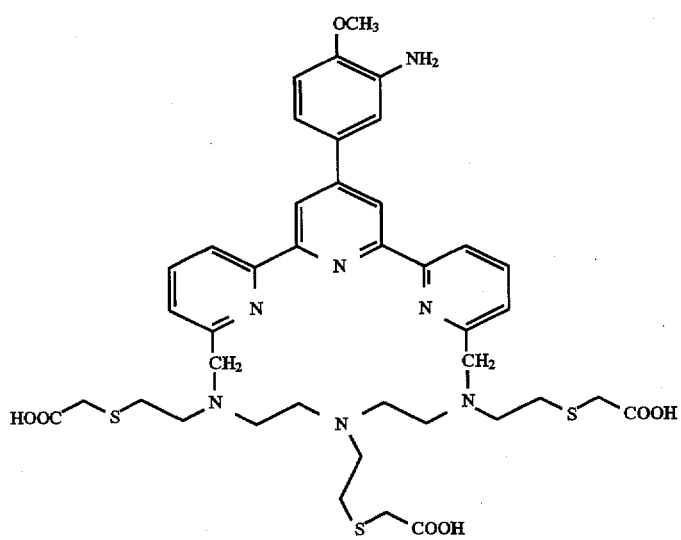
29
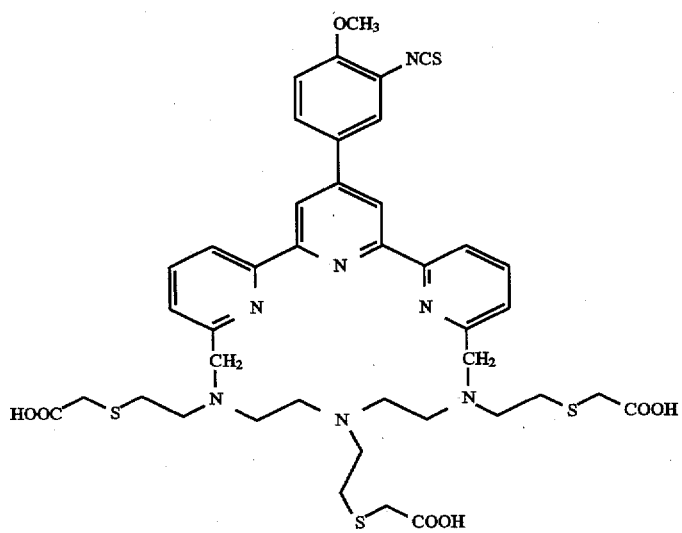
30

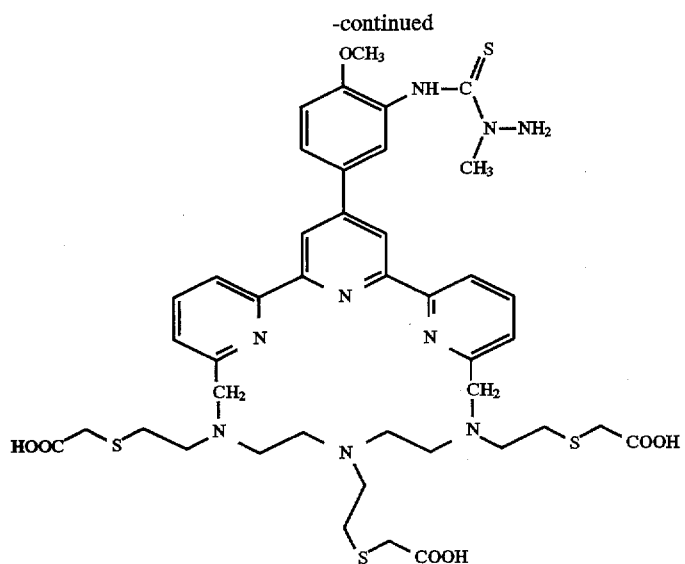
31
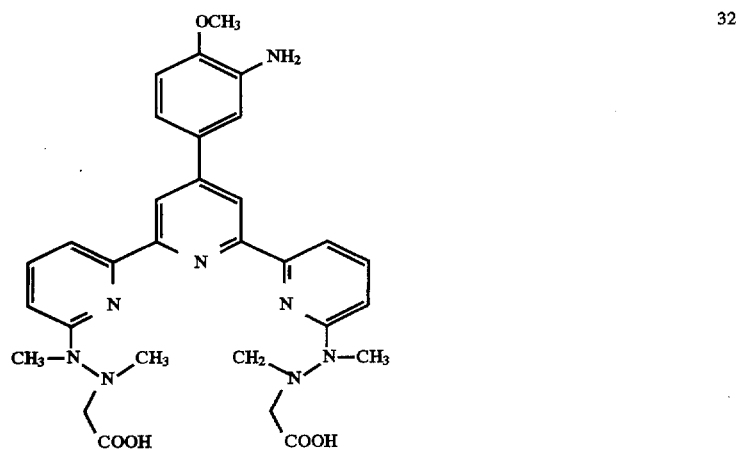
32
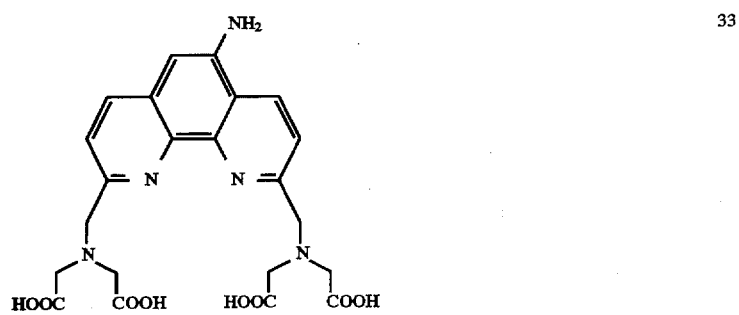
33
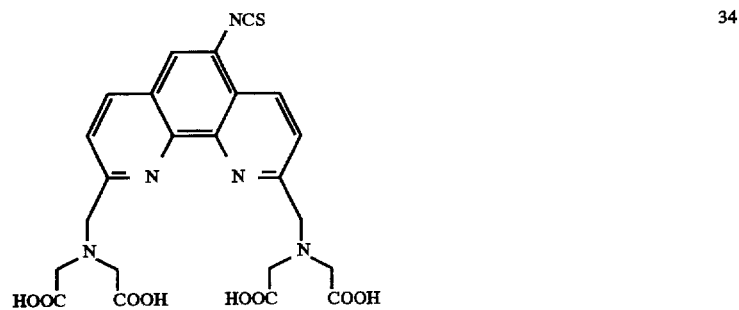
34

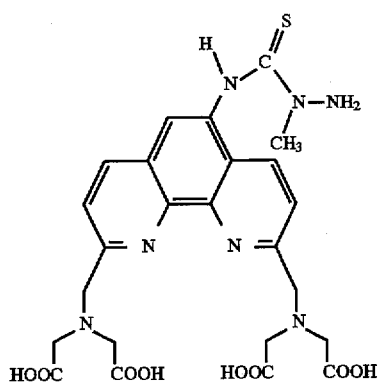
35
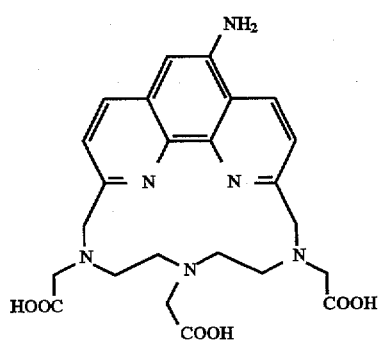
36
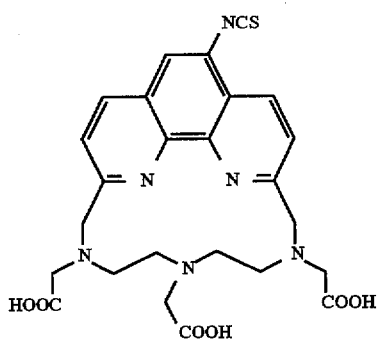
37
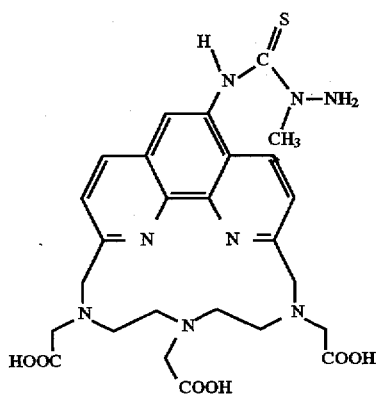
38

-continued
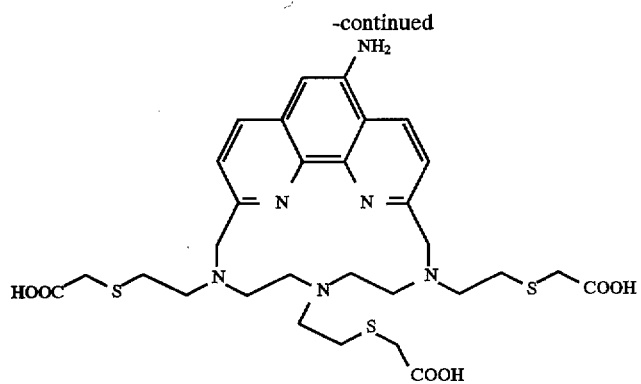
39
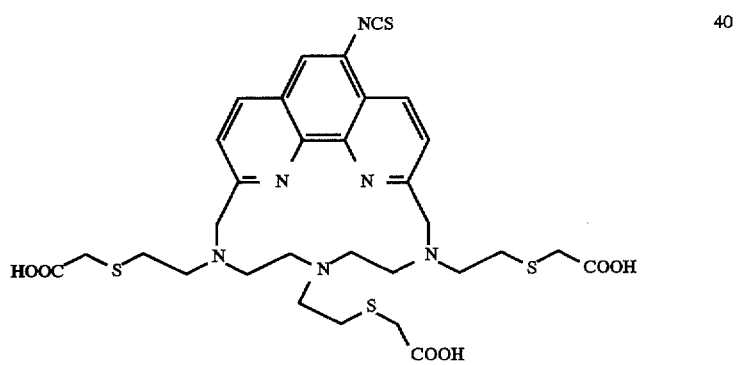
40
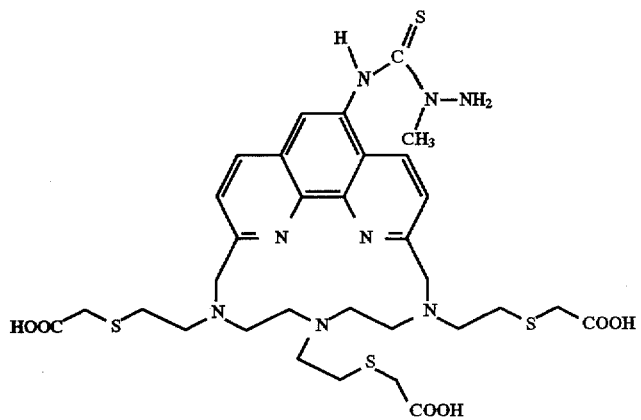
41
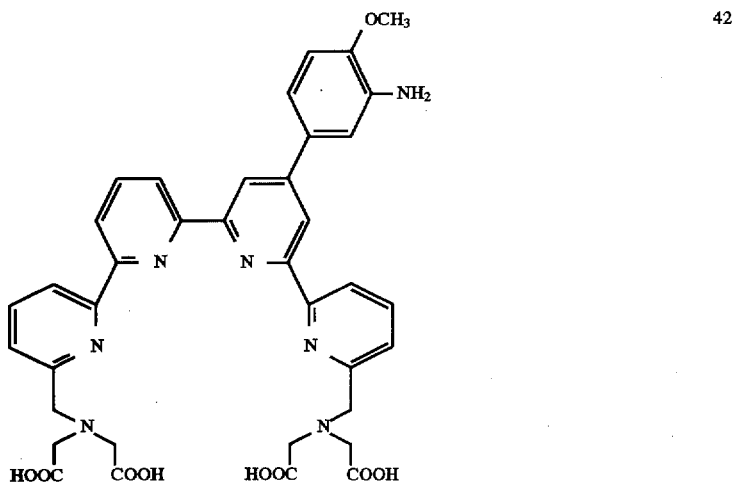
42

-continued
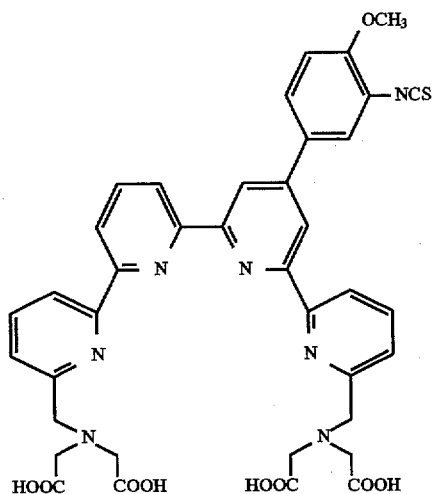
43
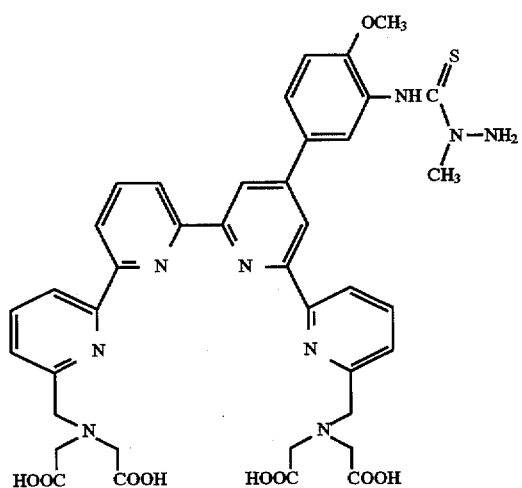
44
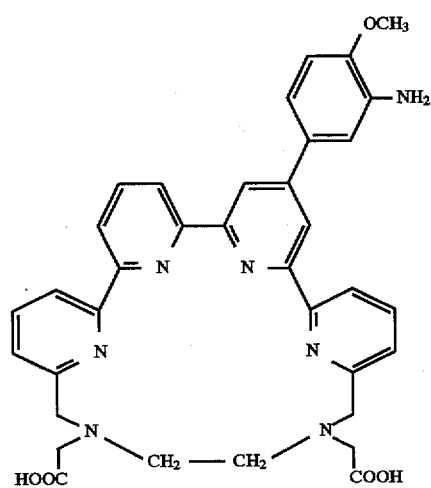
45

46
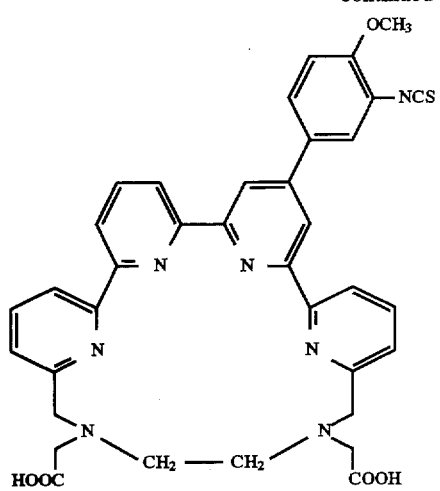
47
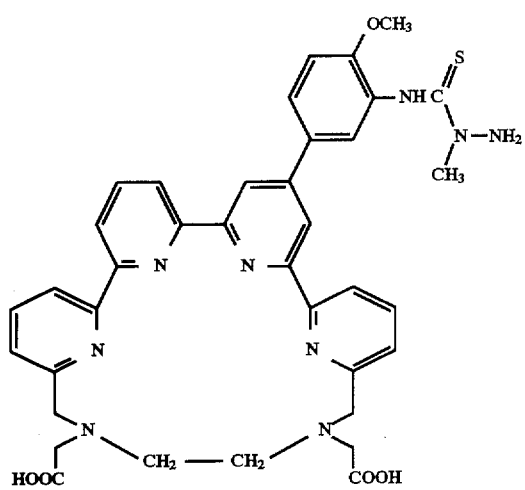
48
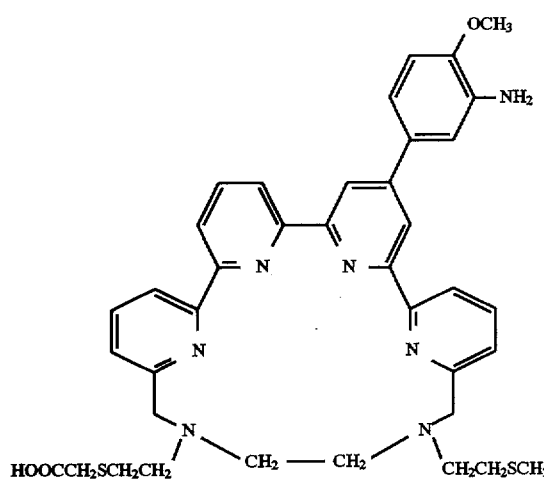

49
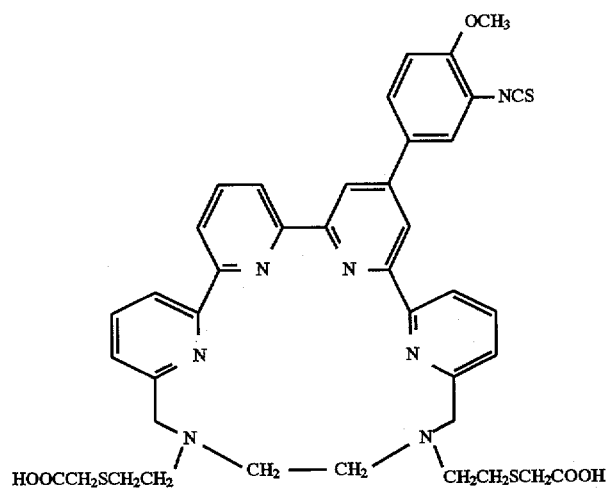
50
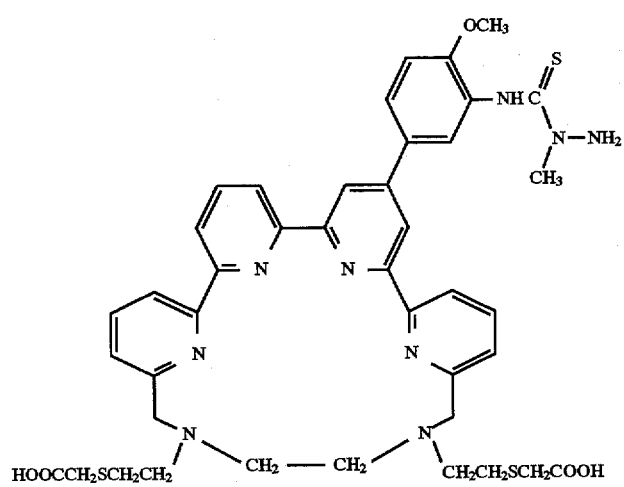
51
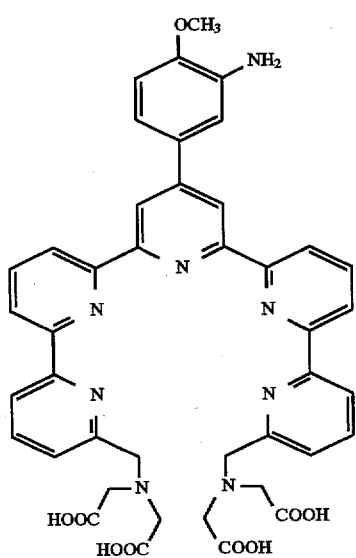

52
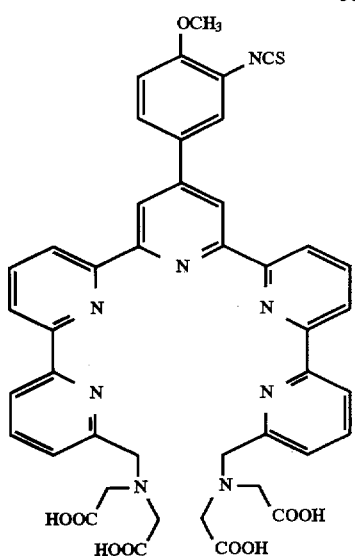
53
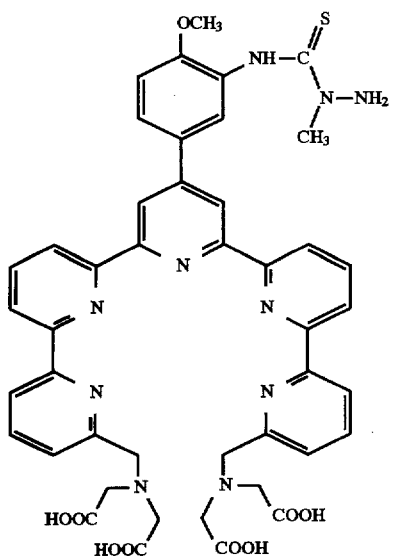
54
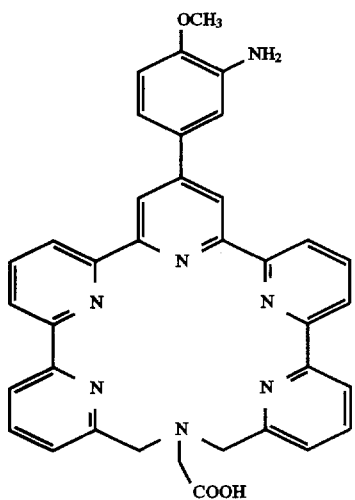

-continued
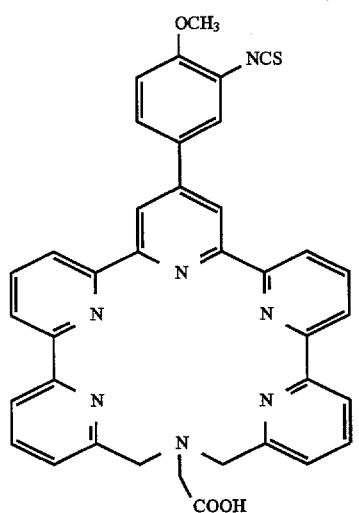
55
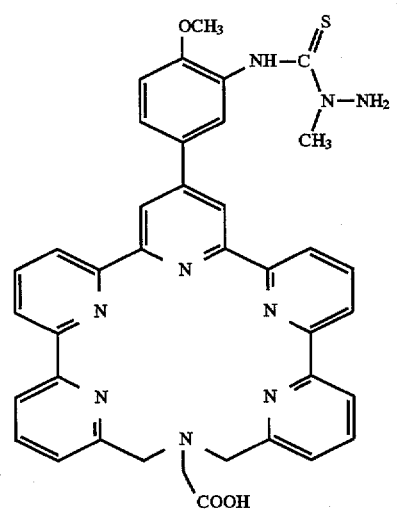
56
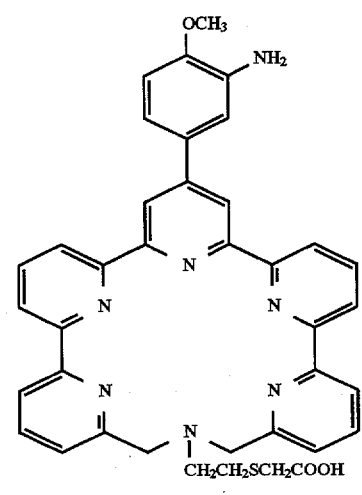
57

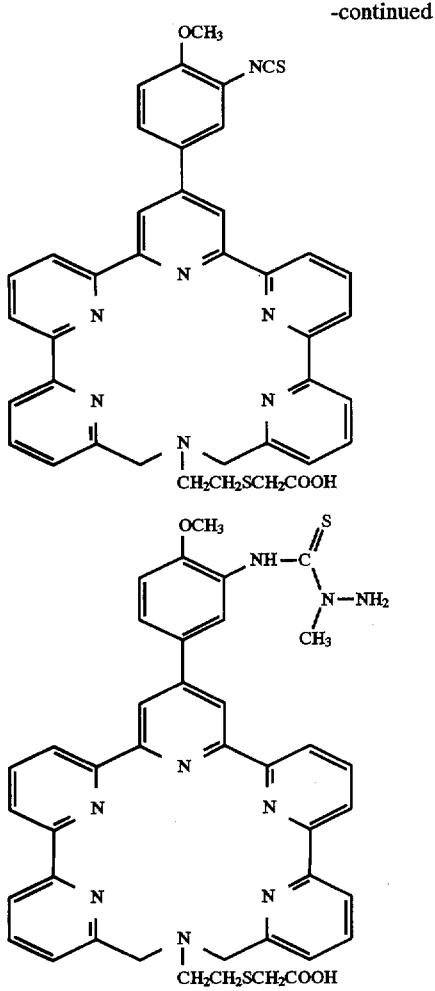

58

59

Preferred classes of complexing agents for use herein include terpyridines represented by structure A-III above and phenanthrolines represented by structure A-IV above. A particularly preferred class of complexing agents has the structure A-III above wherein n=1 and R is a substituted phenyl containing an alkyl or alkoxy substituent and a protein reactive group. Representative preferred species of complexing agents include compounds 20—=depicted above. The currently most preferred complexing agent is TMT isothiocyanate (compound 24).

This invention provides novel terpyridines having the structure A-III set forth in the summary above wherein n=1 and R is

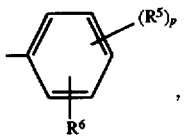

wherein $R^5$ is alkoxy or alkyl, p is 0,1,2,3 or 4 and $R^6$ is a protein reactive group. $R^5$ is alkyl, preferably containing from 1 to about 20, more preferably from 1 to 8 carbon atoms, such as methyl, ethyl and the like; or alkoxy, the alkyl portion of which contains from 1 to about 20, more prefereably from 1 to 8 carbon atoms, such as methoxy, ethoxy and the like. $R^6$ is a protein reactive group as described above. Preferred protein reactive groups include amino, alkylamino, arylamino, carbazido, semicarbazido, thiosemicarbazido, thiocarbazido, isocyanato and isothiocyanato. Especially preferred protein reactive groups include amino, isothiocyanato, and semicarbazido. Especially preferred species include TMT (compound 21) TMT isothiocyanate (compound 24), and THT (compound 20).

Preferred phenanthrolines according to this invention have the structure A-IV above wherein at least one $R^4$ is a protein reactive group. Preferred protein reactive groups include those specified for $R^6$ above.

The polypyridine and phenanthroline complexing agents having metal complexing sites, e.g., heteroatoms and iminodiacetate groups can be prepared by techniques known in the art. Suitable reaction schemes are illustrated in U.S. Pat. No. 4,837,169 and U.S. Pat. No. 4,859,777, the disclosures of which are hereby incorporated herein by reference.

The preparation of certain currently preferred compounds of this invention, namely:

4'-(3-amino-4-methoxyphenyl)-6,6"-bis(N',N'-dicarboxymethyl-N-methylhydrazino)-2,2':6',2"-terpyridine, tetrasodium salt (THT) and 4'-(3-amino-4-methoxy-phenyl)-6,6"-bis[N,N-di-(carboxymethyl)aminomethyl]-2,2':6',2"-terpyridine, tetrasodium salt (TMT) are illustrated in the following Reaction Scheme I:

Reaction Scheme I
Synthesis of THT and TMT
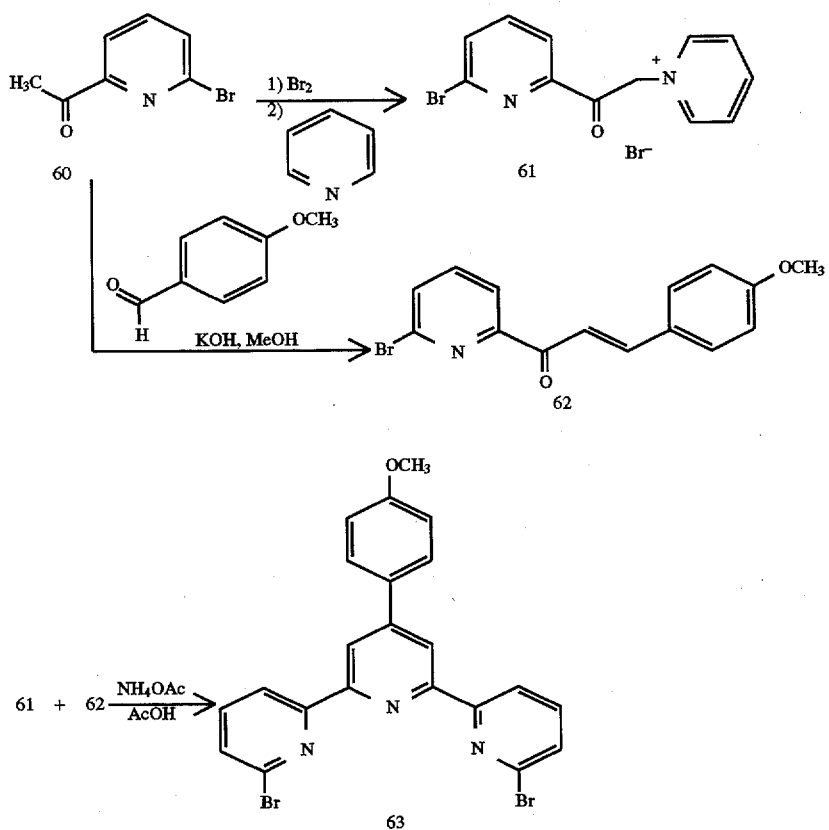
THT Synthesis
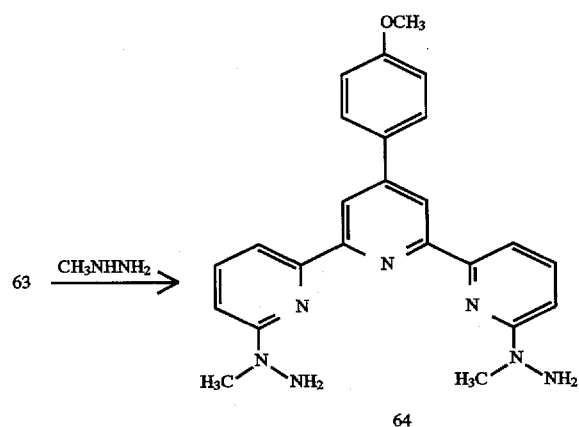

-continued
Reaction Scheme I

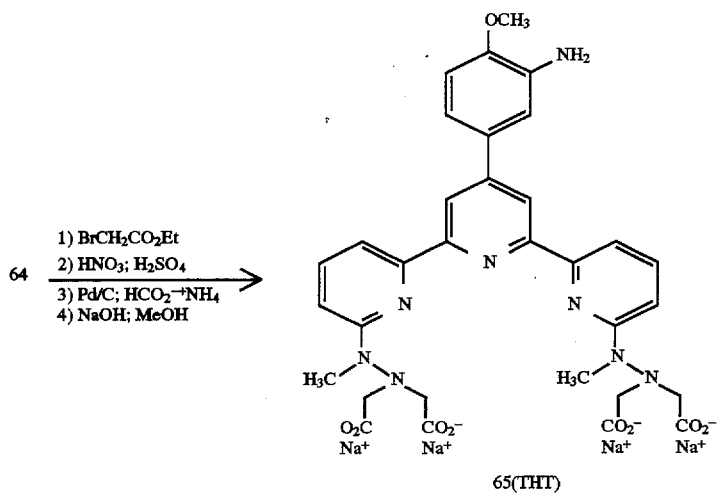

TMT Synthesis

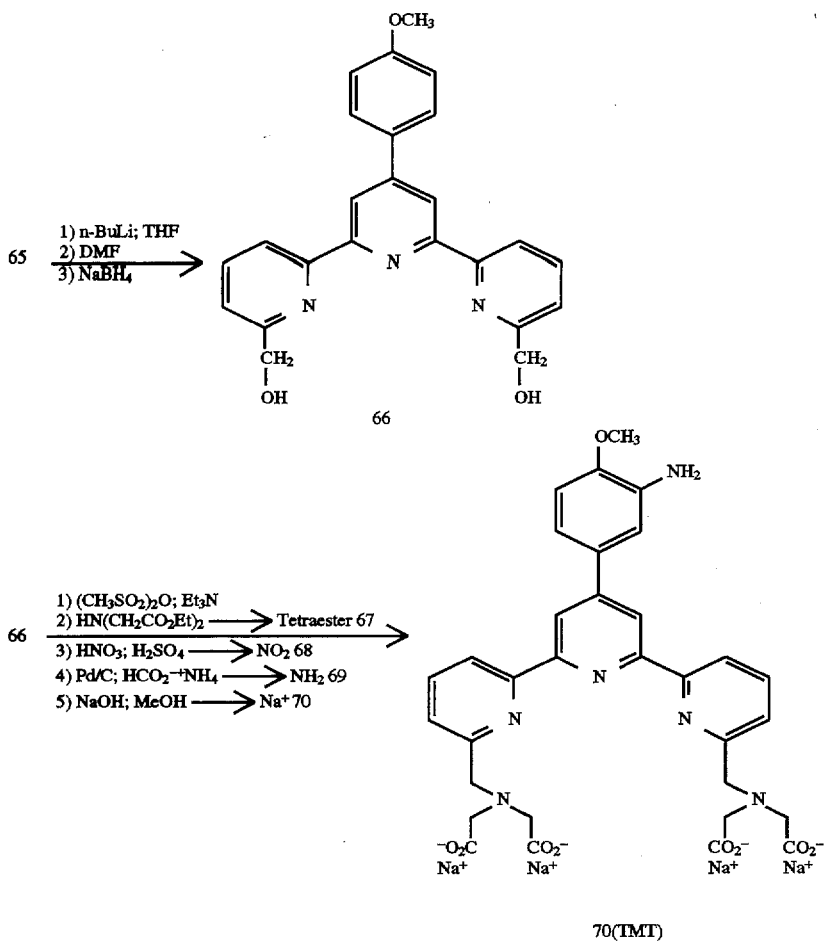

The introduction into the complexing agents of this invention of the requisite protein reactive group described above can be accomplished by conventional chemical reactions. For example, amine groups can be added to phenyl-substituted polypyridines and phenanthrolines by nitration followed by reduction of the nitro groups to amines. If desired, the amine groups can be readily converted to isocyanate groups by reaction with phosgene to produce the carbamoyl chloride which, upon heating, releases HCl to produce the isocyanate. Carboxy groups can be added by treatment of amine-containing polypyridines and phenanthrolines with agents such as glutaric anhydride, followed by suitable selective activation of the carboxyl functionality. Cyclic acetal protected aldehydes can be carried through the reaction sequence necessary to synthesize the polypyridine chelators, and then deprotected before protein conjugation.

The class of terpyridines conforming to Structure A-III above and containing a phenyl group substituted with an alkyl or alkoxy substituent and a protein reactive group is particularly advantageous from a synthetic standpoint. For example, the presence of the alkyl or alkoxy group on the dibrominated intermediate (63) provides enhanced solubility in THF which is a preferred solvent used in the preparation of the intermediate diol (66).

More particularly, TMT (70) is a member of a subclass of the pyridine-containing chelating species of structure A III, namely, the terpyridine system defined by structure (71) wherein R at the 4'-position can be a protein reactive group. In fact, it is a member of a further subclass within (71), which is defined as of the 4'-aryl substituted terpyridine family of compounds (72) wherein either X or Y is a protein reactive group.

Several synthetic routes can be applied to generate derivatives of (72) which contain protein reactive groups at X or Y, and particular, several derivatives wherein either X or Y is hydroxyl, alkyl, alkoxy, or a nitrogen or oxygen derivative connected to a protein reactive group are described below.

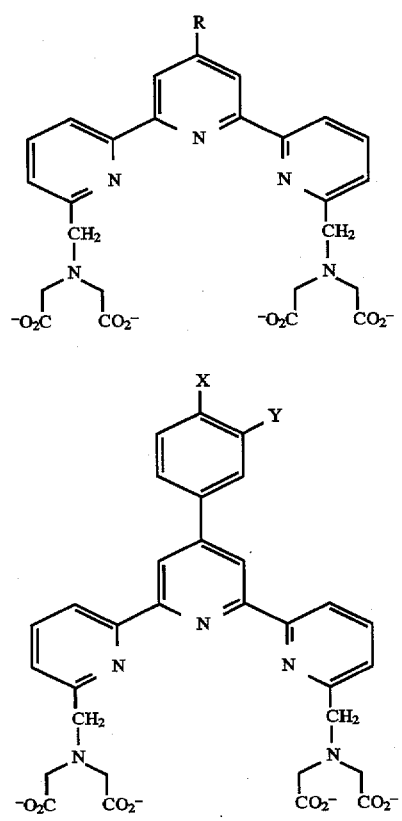

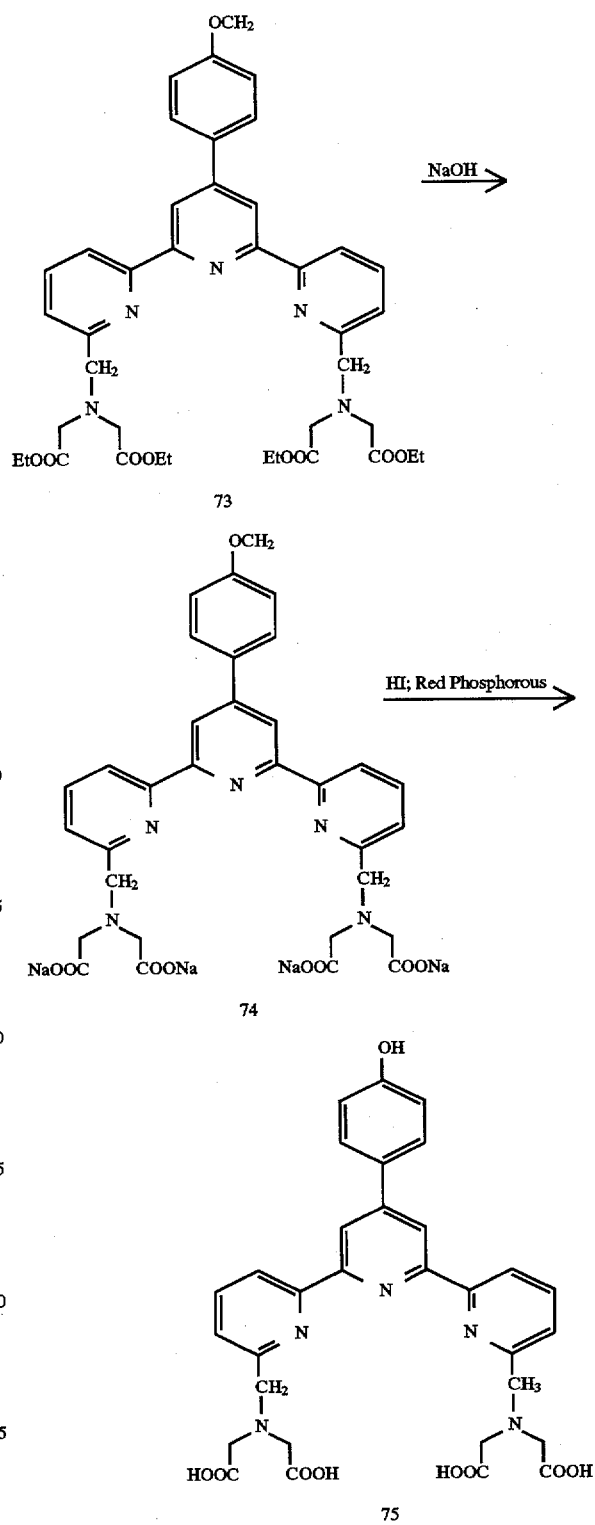

An intermediate in the synthesis of TMT is the tetraester (73). This can be saponified to the tetracarboxylate (74) using sodium hydroxide and then demethylated using HI and red phosphorous to provide the phenol (75).

Phenol (75) can be cyanoethylated with acrylonitrile and then treated with an alcohol such as ethanol in the presence of anhydrous HCl to provide the amidate (76a). Alternatively, the phenol can be alkylated as the phenolate with an alpha-cyano-omega-haloalkane followed by treatment again with alcoholic HCl to provide (76b).

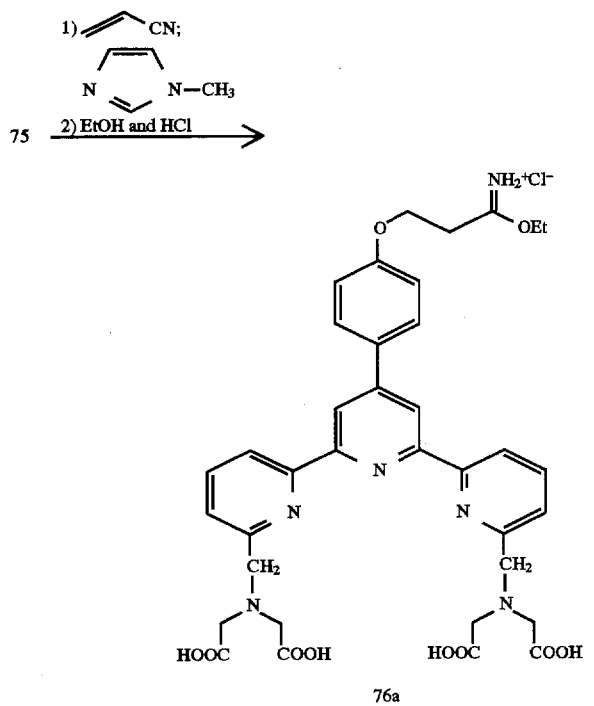
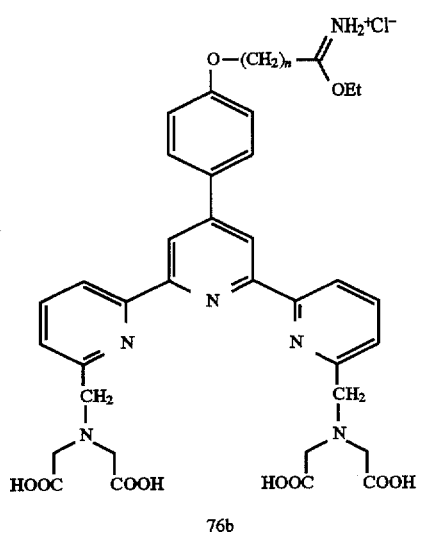
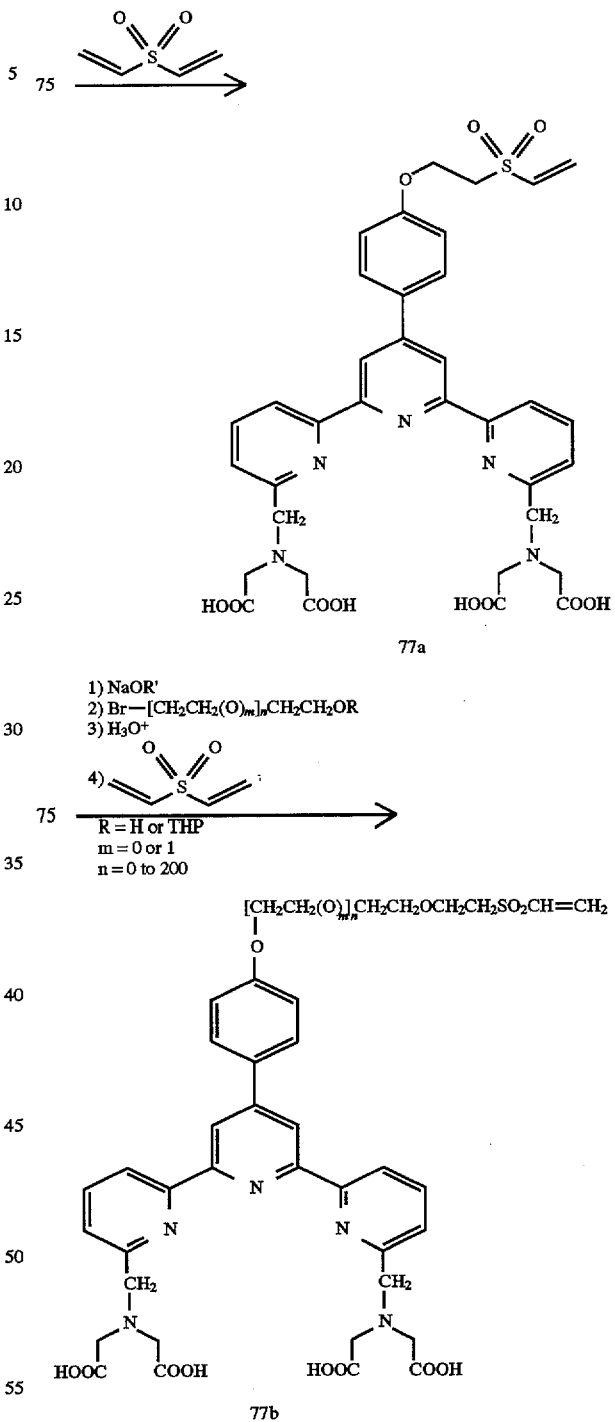

Phenol (75) can also be treated with divinyl sulfone to obtain a monoaddition compound (77a) that provides a vinyl sulfone protein reactive group. Alternatively, (75) can be alkylated with an omega-hydroxy-alpha-alkyl halide (or sulfonate) or with an omega-hydroxy-alpha-polyalkylenoxyalkyl halide (or sulfonate) and thence treated with divinyl sulfone to form the vinyl sulfone (77b). It is also possible to convert the halogeno-alcohol used to generate (77b) into a protected alcohol such as, for example, a tetrahydropyranyl (THP) ether derivative. The free alcohol can be liberated by treating the ketal with aqueous acid before reacting it with divinyl sulfone. The reaction with divinyl sulfone is preferably base catalyzed. In (77b), m is zero or one and n is zero or an integer from 1 to 200, but any oxyalkylene system will be useful.

In another synthetic scheme, (75) can be alkylated with an alpha haloacetate ester such as methyl bromoacetate and then treated with hydrazine to provide the hydrazide (78) which is capable of reacting with aldehyde functionality such as, for example, that introduced by oxidation of a carbohydrate moiety attached to an antibody.

Alternatively, hydrazide (78) can be treated with an aqueous acid such as HCl and then with sodium nitrite to provide the carbonyl azide (79). This can be reacted with amines on proteins at pH's above seven to provide amide linked chelates.

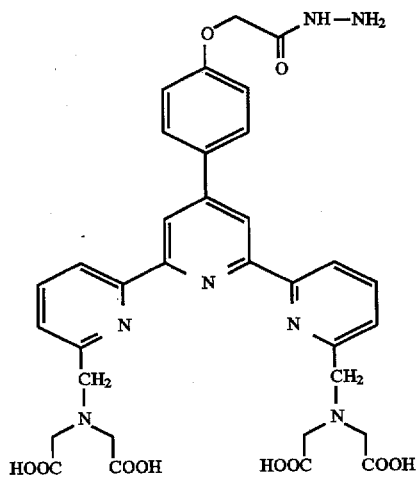

Alternatively, phenol (75) can alkylated to produce an alkylene or oxyalkylene spacer group which is terminated with a hydroxyl or protected hydroxyl functional group as in the case of the preparation of the vinyl sulfones (77b). The aliphatic alcohol can then be treated with an aryl chloroformate such as p-nitrophenyl chloroformate or 2,4,5-trichlorophenyl chloroformate to produce the carbonate (80). This arylchloroformate can react with amine groups or proteins such as amines in lysines and at peptide amine termini.

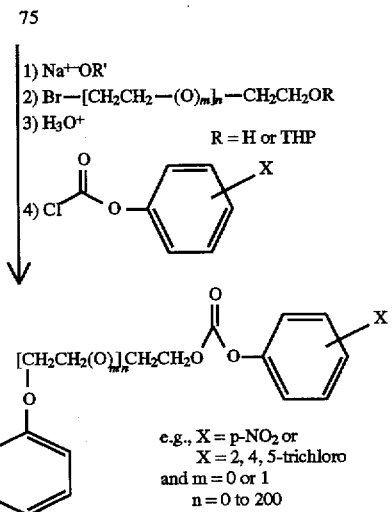

Alternatively, (75) can be reacted directly with cyanuric chloride to produce the cyanurate (81a), or an alcohol, derived from (75) by alkylation, which contains a spacer linkage such as the alcohol intermediate in the preparation of (80) can be so treated to produce the cyanurate (81b). These chlorocyanurates can react with amine groups on proteins.

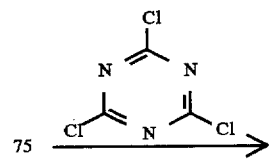

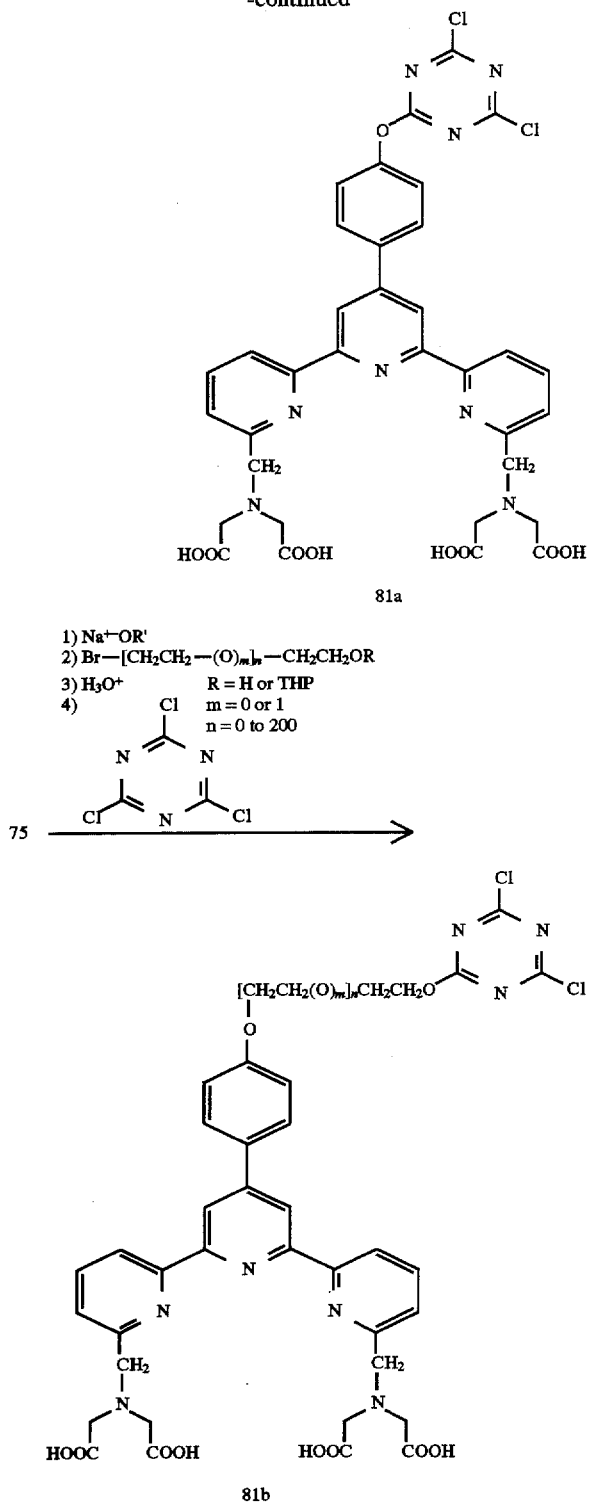

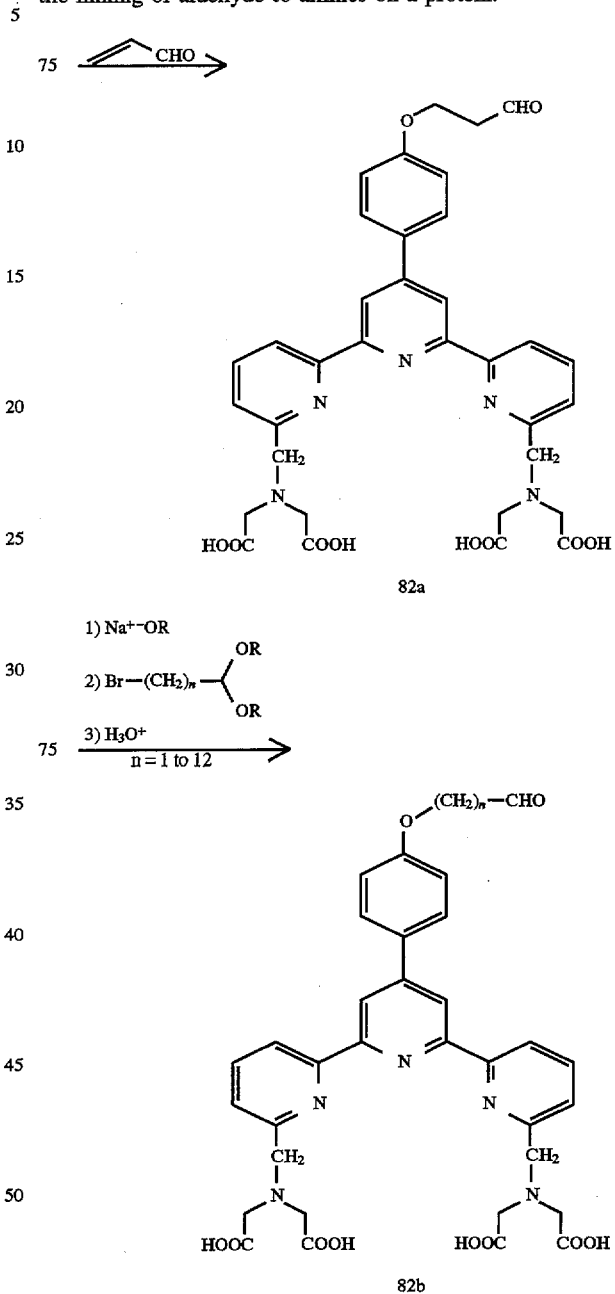

tion procedures (e.g., those incorporating the use of sodium cyanoborohydride as the reducing agent at a ph in the range of 4 to 7, preferably about pH 6, in an aqueous system) for the linking of aldehyde to amines on a protein.

Alternatively, phenol (75) can be converted to aldehyde (82a) by treatment with acrolein, and to aldehyde (82b) by treatment with a haloalkyl acetal (as an aldehyde protecting group) followed by deprotection of the aldehyde with aqueous acid. These aldehydes are suitable for reductive amina- Alternatively, phenol (75) can be converted to amine (83a) by treatment with acrylonitrile (e.g. in the presence of N-methylimidazole as catalyst) followed by hydrogenation of the nitrile in warm acetic acid solution using hydrogen and 10% palladium on carbon as a catalyst. In addition, (75) can be converted to amine (83b) by alkylation with an omega-haloalkyl nitrile followed by hydrogenation of the nitrile in warm acetic acid solution using hydrogen and 10% palladium on carbon as a catalyst.

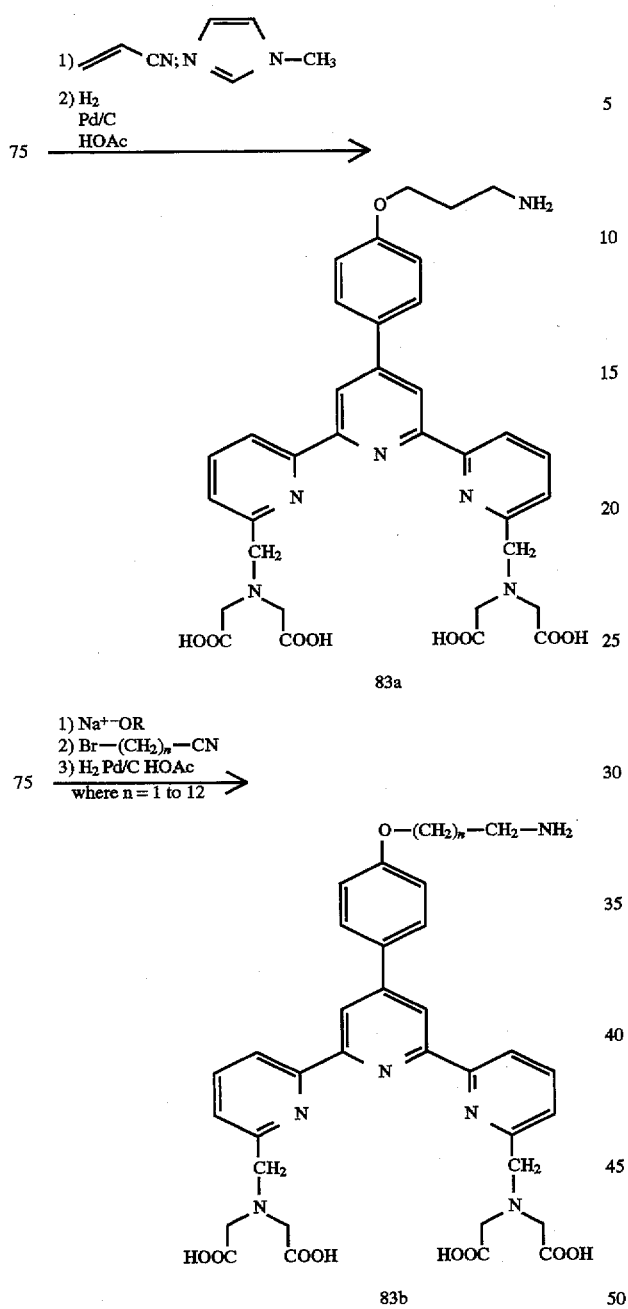

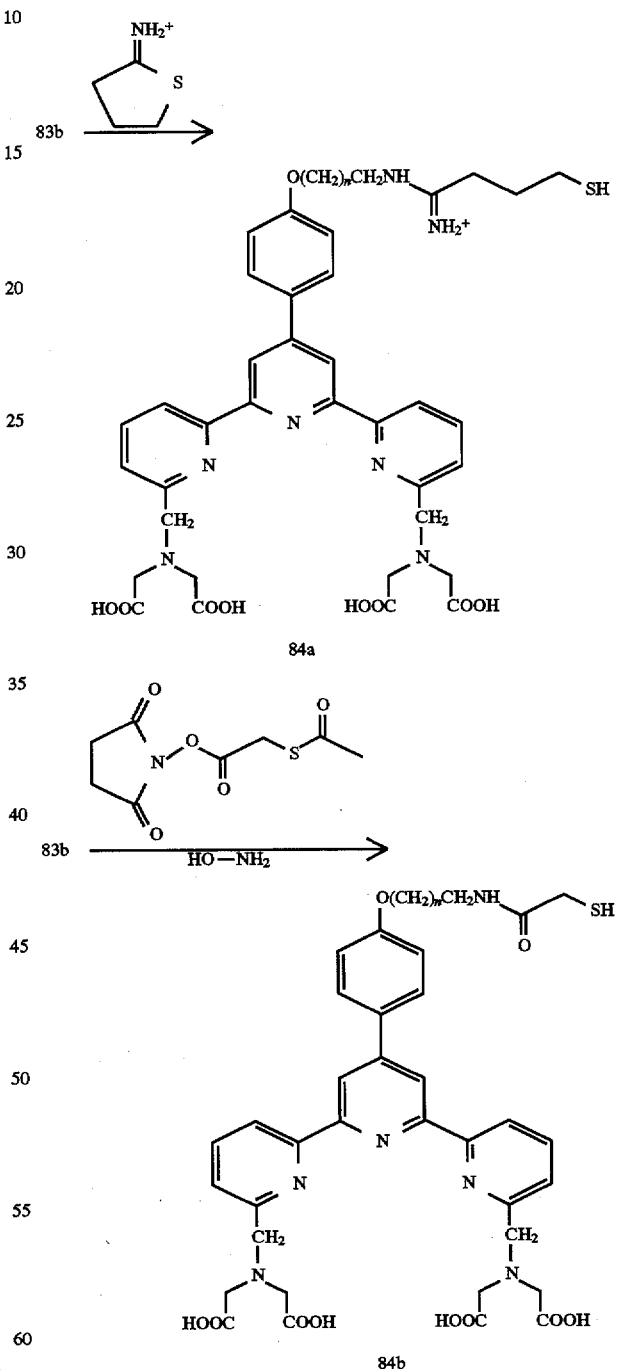

from Pierce Chemical Company). For example, the amines represented by (83b) can be treated with 2-iminothiolane to generate (84a) or with N-succinimidyl S-acetylthioacetate (SATA) followed by treatment with hydroxylamine to generate (84b). These species contain free sulfhydryl SH groups which can react with maleimide functionality that can be introduced at amine sites in a protein using reagents such as SMCC [N-(4-carboxycyclohexylmethyl)-maleimide N-hydroxysuccinimidate] and the like.

The above amines can be attached to proteins in several ways. For example, they are suitable for use in reductive amination procedures (e.g., incorporating the use of sodium cyanoborohydride as the reducing agent at a pH of about 6 in an aqueous system) to couple the amine with aldehyde functionality that is generated by the action of an oxidizing agent such as sodium periodate on a carbohydrate moiety attached to a protein (such as an antibody). Aldehyde functionality can also be generated on a protein using reagents such as 4-azophenylglyoxal (APG, available from Pierce Chemical Co.) which reacts selectively with arginine residues on the protein. These aldehydes can then be reacted with the amines (83a) and (83b) as above.

In addition, these amines can be attached to proteins by first being further elaborated with commonly available heterobifunctional reagents (such as are available commercially In addition, the amines represented by (83b) can be treated with SMCC [N-(4-carboxycyclohexylmethyl)-maleimide N-hydroxysuccinimidate] to generate (84c). These species contain maleimide functionality which can react with free sulfhydryl SH groups that can be introduced at amine sites in a protein using reagents such as 2-iminothiolane or with N-succinimidyl S-acetylthioacetate (SATA) followed by treatment with hydroxylamine. Free sulfhydryl sites can also be generated in a protein by the action of sulfhydryl-containing reducing agents such as dithiothreitol on disulfide bonds which may be present in the protein or desired protein fragment.

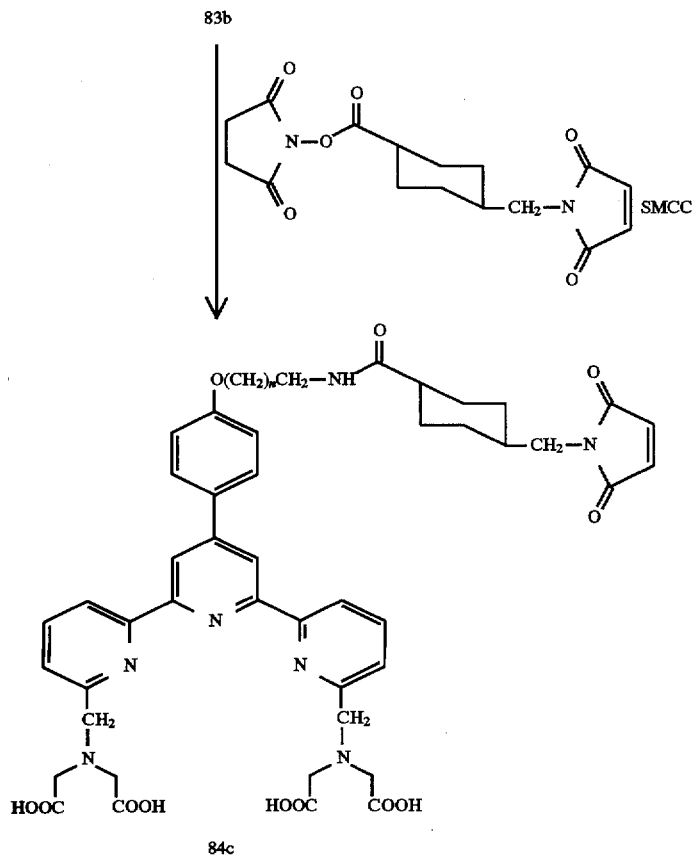

Also within the scope of this invention is the generation of linking chemistries from amine (85) where X is as defined above. Amine (85) can be treated with aqueous hydrochloric acid and sodium nitrite (to form HONO) which will then react with the amine to form the diazonium salt (86). This material can be coupled to tyrosine moieties on proteins via diazo linkages to the aromatic ring containing the hydroxyl group. This is represented schematically as (87) wherein represents a protein such as an antibody moiety containing a tyrosine hydroxy-aromatic ring (such as a tyrosine in an antibody such as ING-1).

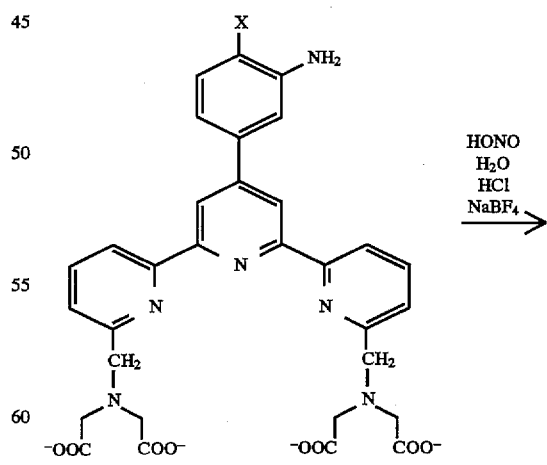

61

-continued

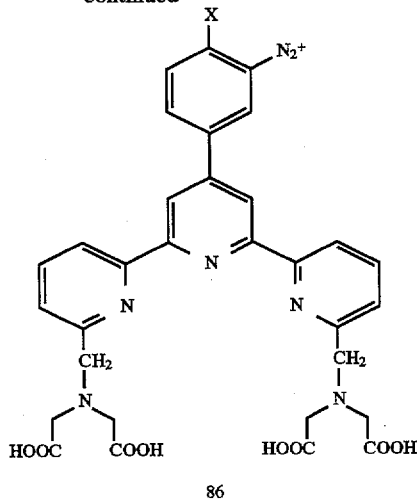
86

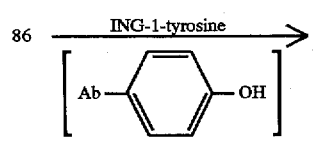

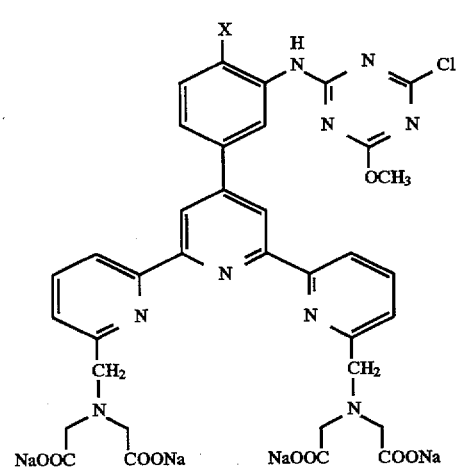
87

In addition, amine (85) can be treated with excess cyanuric chloride to produce the dichlorocyanuramide (88) and with 2-methoxycyanuric dichloride to produce the chloromethoxycyanuramide (89). Both of these derivatives can be reacted at amine groups such as lysine amines or the terminal amine groups of peptide chains in proteins. Reaction occurs via the displacement of chloride from the triazine ring.

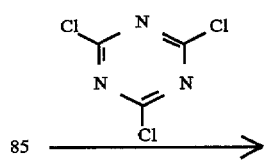

62

-continued

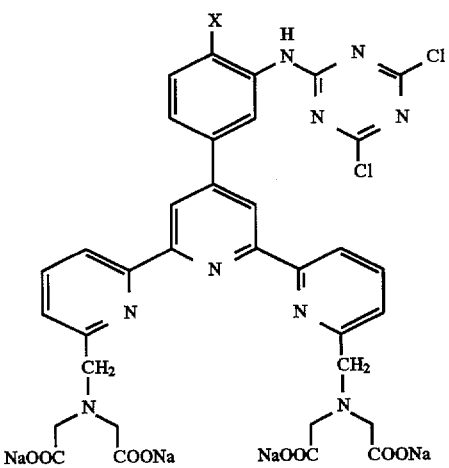
88

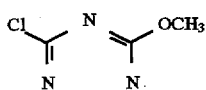

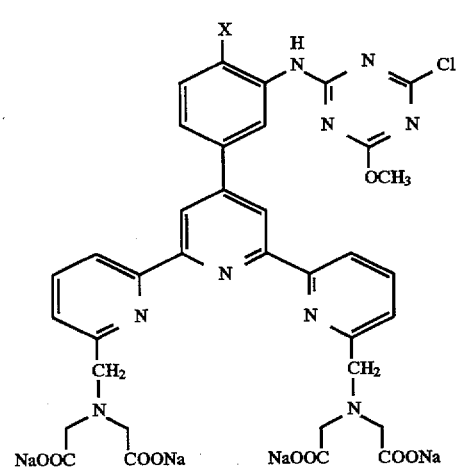
89

In addition, amine (85) can be reacted with the N-hydroxysuccinimido ester of alpha-iodoacetic acid or with alpha-iodoacetic acid anhydride to produce the iodoacetamide derivative (90). This material can be reacted with proteins containing free sulfhydryl groups such as those utilized in the reactions of maleimide derivative (84c) above. Iodoacetamide (90) will also react with amines on proteins, such as the epsilon amine of lysine and the terminal amine of a peptide chain.

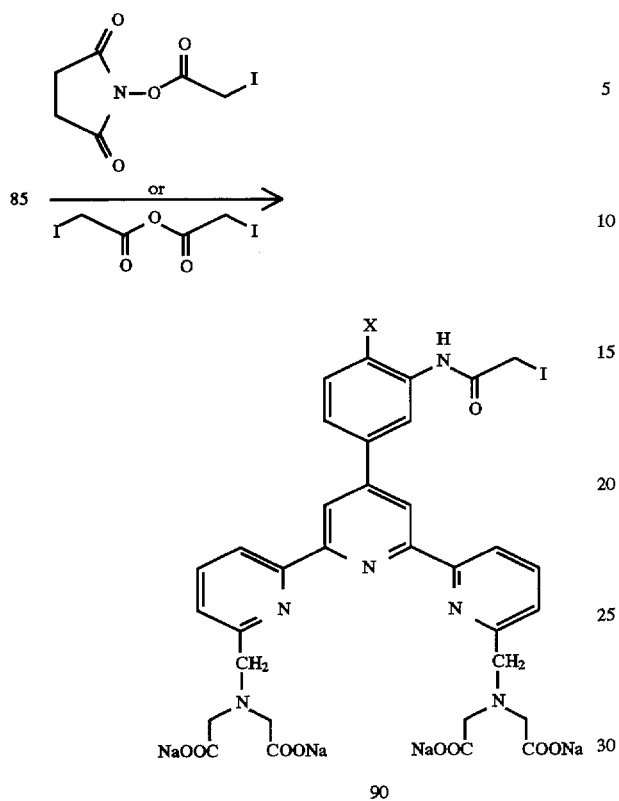

90

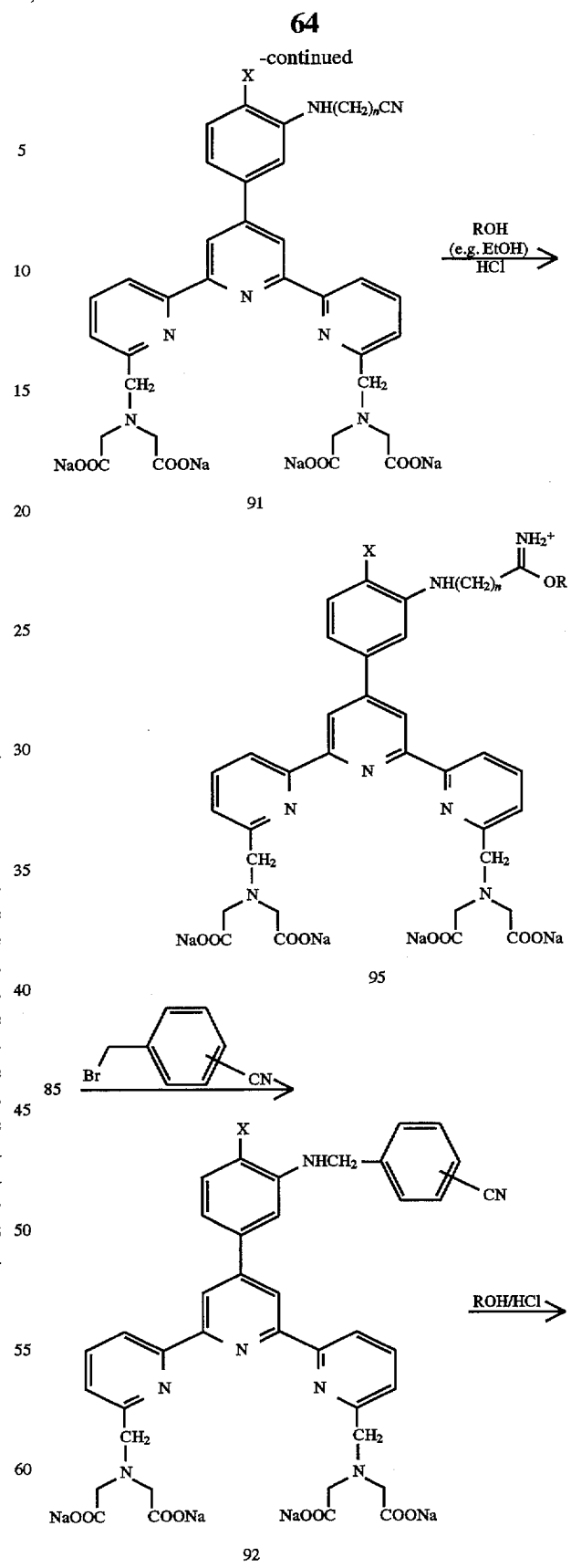

91

95

92

In addition, amine (85) can be alkylated with nitrile-containing alkylhalides such as Br—(CH$_2$)$_n$—CN to provide nitriles (91) wherein n is an integer from 1 to 20. Amine (85) can also be alkylated with nitrile-containing benzylic halides such as alpha-bromomethylbenzonitriles to provide nitriles (92). Furthermore, amine (85) can be acylated with active esters (or similarly activated carbonyl derivatives) of carboxylic acids which contain nitrile functionality (such as the cyanobenzoyl systems and the aliphatic acid derivatives such as cyanoacetic acid derivatives) to provide nitrile amides (93) and (94). Any of these nitriles can be converted into the corresponding amidates by the action of alcohol and anhydrous HCl to provide (95), (96), (97), and (98), respectively. These amidates will react with amines on proteins such as the epsilon amines of lysines and the terminal amines of peptide chains.

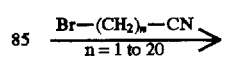

65
-continued
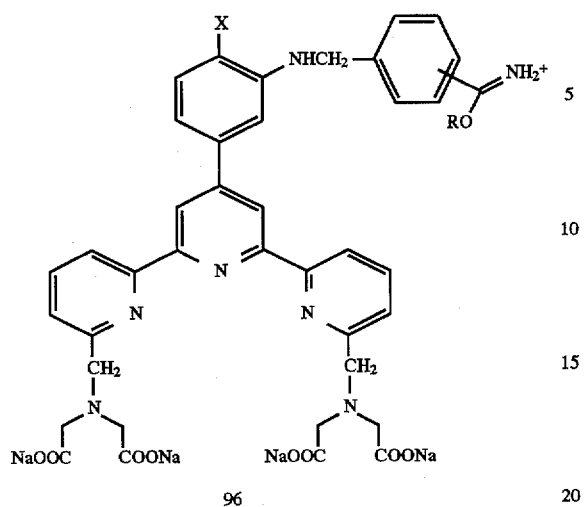
96
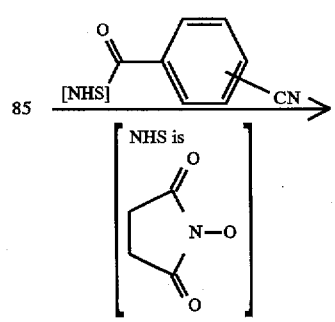
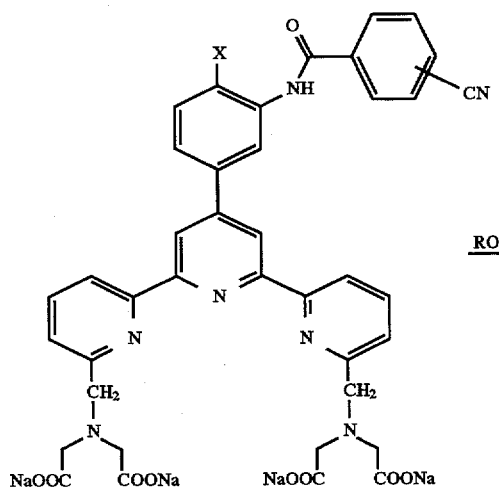
93
66
-continued
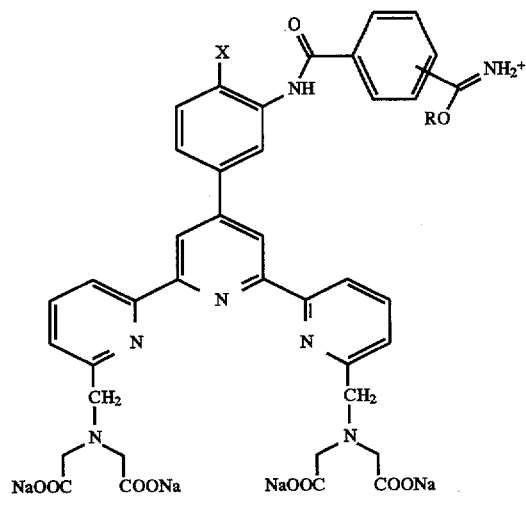
97
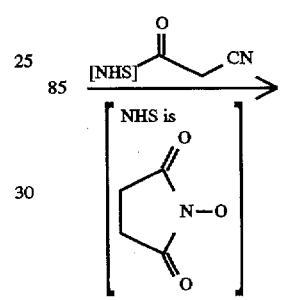
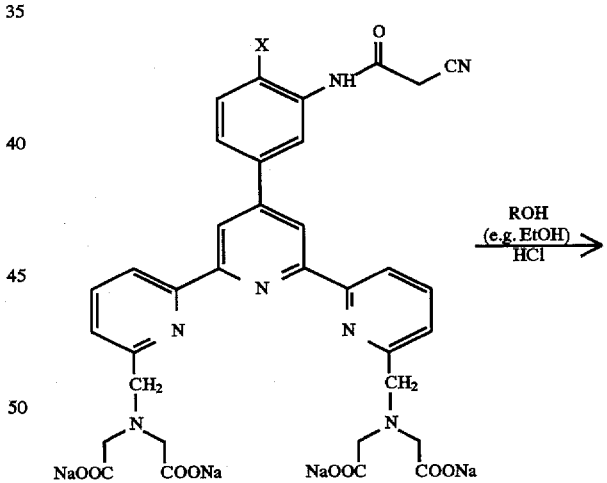
94

-continued

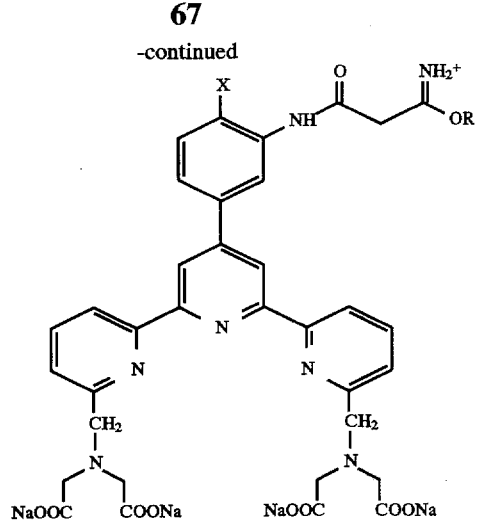

98

It should be recognized that in all of the above reaction schemes, the carboxylic acid species of the iminodiacetic acid moieties can be protonated or can be present as ionic species (represented, for example, as sodium salts). The extent of protonation and of deprotonation of any one species is a function of the pH of the reaction medium which contains both the protein reactive group containing reagent and the protein. The use of buffer salts such as, for example, phosphate, borate, citrate and acetate buffers to control the pH of the reaction medium is a part of this aspect of the invention.

While the foregoing discussion of synthetic routes useful for the preparation of representative protein reactive groups has been focused on certain preferred terpyridine systems defined by structure 71, it will be understood that these chemistries can be applied to the wider variety of compounds defined more generally by structure A-I as needed to carry out the purposes of this invention.

The products of the reaction of any of these protein reactive group containing chelators with proteins (or other immunoreactive groups) can be purified by conventional techniques such as diafiltration, HPLC, electrophoresis, and the like. The proteins (or other immunoreactive groups) may be subsequently modified with agents such as PEG (polyethylene glycol) reagents as is well known in the art to impart reduced immunogenicity to the modified proteins.

The modified proteins can be treated with radioisotopes of metal ions such as $^{90}Y^{+3}$ (as a non-limiting example) and the radionuclide-chelate-protein can be used for the therapeutic treatment of tumors, particularly if the protein is a tumor antigen specific antibody or fragment thereof.

The modified proteins can be treated with radioisotopes of metal ions such as $^{111}In^{+3}$ or $^{187}Y^{+3}$ (as non-limiting examples) and the radionuclide-chelate-protein so produced can be used for the diagnostic imaging of tumors in cancer patients, particularly if the protein is a tumor antigen specific antibody or fragment thereof.

The novel terpyridines and phenanthrolines of this invention can be prepared according to the above described synthetic techniques. Additional illustrative preparations are set forth in the examples which follow.

The targeting radioactive immunoreagent of this invention includes a radionuclide ion. The radionuclide ion can be selected, for example, from Sc, Fe, Pb, Ga, Y, Bi, Mn, Cu, Cr, Zn, Ge, Mo, Tc, Ru, In, Sn, Sm, Sb, W, Re, Po, Ta and Tl ions. Preferred radionuclides include $^{44}Sc^{+++}$, $^{64,67}Cu^{++}$, $^{111}In^{+++}$, $^{212}Pb^{++}$, $^{68}Ga^{++}$, $^{90}Y^{+++}$ and $^{212}Bi^{+++}$ ions. Of these, the most preferred are $^{90}Y^{+++}$ ions.

The metal radionuclide ion and the complexing agent are easily complexed by merely mixing an aqueous solution of the complexing agent with a metal radionuclide salt in an aqueous solution preferably having a pH of 4 to 11. The salt can be any water soluble salt of the metal such as halogen salts. The chelate is generally prepared in aqueous solution at a pH of between 5 and 9 and preferably from 6 to 8. The complex optionally is mixed with buffers such as acetate, phosphate and borate to produce the optimum pH.

The targeting immunoreagent of this invention includes an immunoreactive group covalently bonded to the complexing agent. The targeting immunoreagent thus comprises a conjugate of a complex having the structure A-I above and the immunoreactive group. The complexing agent and the metal radionuclide can be complexed either before or after the complexing agent is attached to the immunoreactive group. As used herein the term "immunoreactive group" is meant to include any organic compound which is capable of covalently bonding to the complexing agent and which is found in a living organism or is useful in the diagnosis, treatment or genetic engineering of cellular material or living organisms, and which has a capacity for interaction with another component which may be found in biological fluids or associated with cells to be treated such as tumor cells.

Depending upon the intended use, the immunoreactive group can be selected from a wide variety of naturally occurring or synthetically prepared materials, including, but not limited to enzymes, amino acids, peptides, polypeptides, proteins, lipoproteins, glycoproteins, hormones, drugs (for example digoxin, phenytoin, phenobarbitol, thyrozine, triiodothyronine, gentamicin, carbamazepine, and theophylline), steroids, vitamins, polysaccharides, viruses, protozoa, fungi, parasites, rickettsia, molds, and components thereof, blood components, tissue and organ components, pharmaceuticals, haptens, lectins, toxins, nucleic acids (including oligonucleotides), antibodies (including genetically engineered antibodies and fragments thereof), antibody fragments, antigenic materials (including proteins and carbohydrates), avidin and derivatives thereof, biotin and derivatives thereof, and others known to one skilled in the art.

Preferred immunoreactive groups for use in the practice of this invention are those which have a receptor molecule specific to a ligand of interest. Thus, a specific binding reaction involving the reagent can be used for the targeting expected. Examples of such ligand-receptor complexes include, but are not limited to antibody-antigen, avidin-biotin, repressor (inducer)—promoter of operons and sugar-lectin complexes. Additionally, complementary nucleic acids, i.e., a hybridized product of complementary strands, are also considered specific binding materials as the term is used herein.

Particularly preferred immunoreactive groups include (1) any substance which, when presented to an immunocompetent host, will result in the production of a specific antibody capable of binding with that substance, or (2) the antibody so produced, which participates in an antigen-antibody reaction. Thus, the immunoreactive group can be an antigenic material, an antibody, or an anti-antibody. Both monoclonal and polyclonal antibodies are useful. The antibodies can be whole molecules or various fragments thereof, as long as they contain at least one reactive site for reaction with the reactive groups on the complexing agent or with linking groups as described herein. Specifically contemplated as being included within these preferred immunoreactive groups are antibodies and proteins produced by the techniques of molecular biology. Such techniques are well known in the art and are described, for example, in U.S. Pat. Nos. 4,816,397 and 4,816,567.

In certain embodiments, the immunoreactive group can be an enzyme which has a reactive group for attachment to the complexing agent. Representative enzymes include, but are not limited to, aspartate aminotransaminase, alanine aminotransaminase, lactate dehydrogenase, creatine phosphokinase, dihydrofolate reductase, gamma glutamyl transferase, alkaline acid phosphatase, prostatic acid phosphatase, horseradish peroxidase and various esterases.

If desired, the immunoreactive group can be modified or chemically altered to provide reactive groups for attaching to the complexing agent by techniques known to those skilled in the art. Such techniques include the use of linking moieties and chemical modification such as described in WO-A-89/02931 and WO-A-89/02932, which are directed to modification of oligonucleotides, and U.S. Pat. No. 4,719,182 the disclosures of all of which are hereby incorporated herein by reference in their entirety.

Two highly preferred uses of the targeting immunoreagents of this invention are for the diagnostic imaging of tumors and the radiological treatment of tumors. Preferred immunological groups therefore include antibodies to tumor-associated antigens. Specific examples include B72.3 antibodies (described in U.S. Pat. Nos. 4,522,918 and 4,612,282) which recognize colorectal tumors, 9.2.27 anti-melanoma antibodies, D612 antibodies which recognize colorectal tumors, UJ13A antibodies which recognize small cell lung carcinomas, NRLU-10 (Tfs-2) antibodies which recognize small cell lung carcinomas and colorectal tumors, 7E11C5 antibodies which recognize prostate tumors, CC49 antibodies which recognize colorectal tumors, TNT antibodies which recognize necrotic tissue, PR1A3 antibodies, which recognize colon carcinoma [Richman, P. I. and Bodmer, W. F. (1987) Int. J. Cancer Vol. 39, pp. 317–328], ING-1 and other genetically engineered antibodies, which are described in International Patent Publication WO-A-90/02569, B174 antibodies (developed at Biomira, Inc. of Edmonton, Canada, which recognize squamous cell carcinomas, B43 antibodies which are reactive with certain lymphomas and leukemias and others which may be of particular interest.

Such antibodies and other useful immunological groups described above are large, complex molecules having multiple sites for appendage of the complexing agent. Consequently, the immunoreactive group can have appended to it additional complexing agents via one of the protein reactive groups. Thus, the term immunoreactive group is intended to include immunological groups having complexing agent molecules bonded thereto through one or more protein reactive groups.

Additionally, an antibody or fragment thereof containing a carbohydrate region can be attached to the complexing agent through the carbohydrate region of the antibody, such as described in U.S. Pat. No. 4,937,183, the disclosure of which is hereby incorporated herein by reference in its entirety. Useful methods for attaching an antibody are also described in U.S. Pat. Nos. 4,671,958; 4,699,784; 4,741,900; and 4,867,973. The term "protein reactive group" as defined herein is intended to include such linkages.

Other techniques for performing the covalent binding of the immunoreactive group to the radioactive metal complexing agents are known in the art and include simply mixing the materials together.

The radioactive immunoreagent of this invention can contain any ratio of metal radionuclide ion to complexing agent. In preferred embodiments, the mole ratio of metal ion to complexing agent is from about 1:100 to about 1:1.

The ratio of the complexing agent to the immunoreactive group can vary widely from about 0.5:1 to 10:1 or more. In some embodiments, the mole ratio of complexing agent to immunoreactive groups is from about 1:1 to about 6:1.

Figure 6:
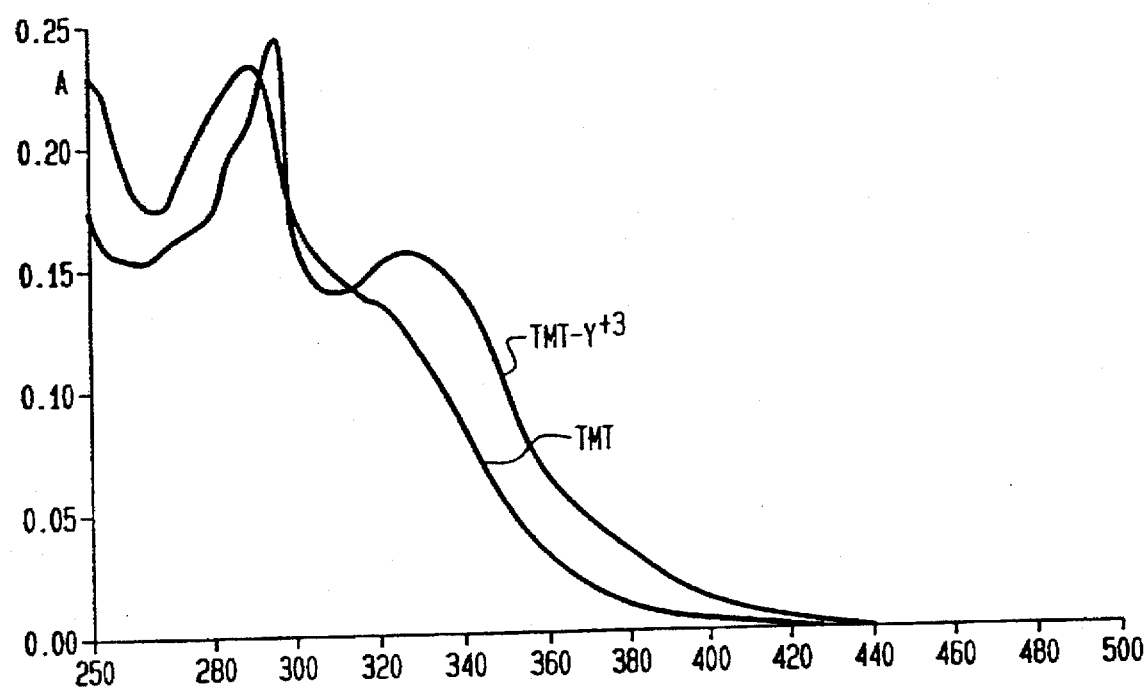
FIGS. 6 and 7 are absorption spectra of TMT, TMT-$Y^{+++}$ and TMT-$Pb^{++}$.
Figure 7:
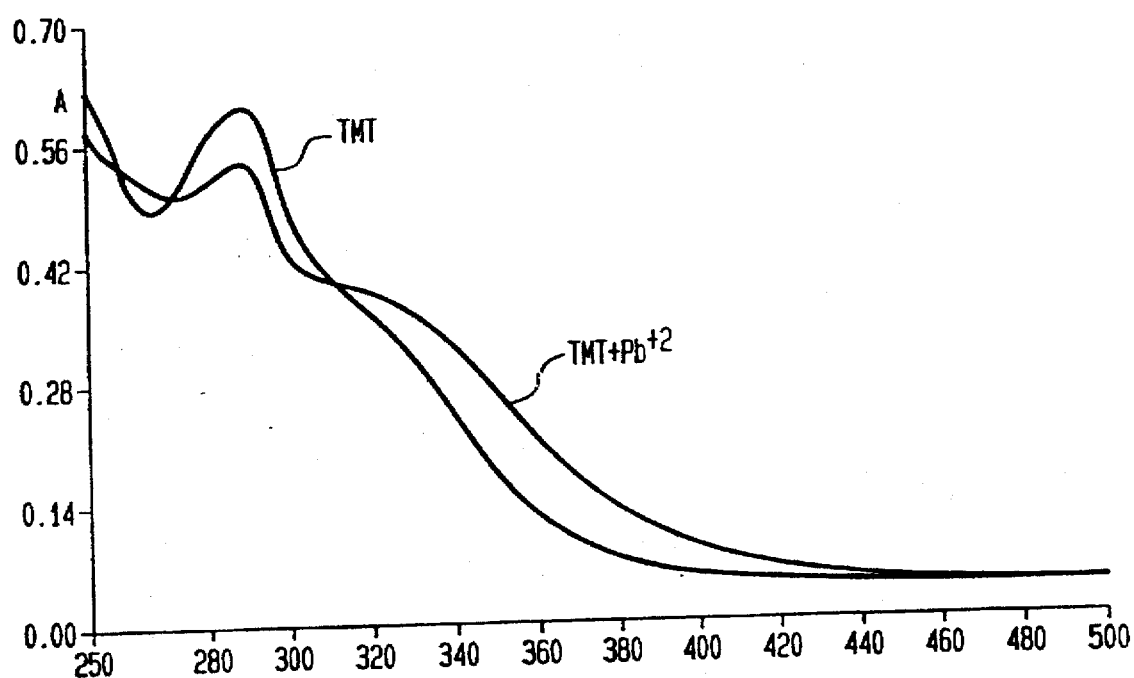

FIGS. 6 and 7 are absorption spectra of complexing agents and metal complexes of this invention. Portions of the spectra do not overlap with those of the proteins to which the complexing agents are chemically bonded. Similar spectral shifts were obtained between complexing agents of this invention and other representative cations such as $Ga^{+3}$, $Bi^{+3}$, $In^{+3}$, $Sc^{+3}$ and $Cu^{+2}$. Thus, the immunoreagent of this invention can be readily spectrophotometrically analyzed.

The following examples further illustrate the invention:

SECTION I:

COMPLEXING AGENTS/CHELATORS

Preparation 1

Preparation of 4'-(3-Amino-4-methyoxyphenyl)-6,6"-[N,N-di(carboxymethyl)amino-methyl]-2,2':6',2"-terpyridine, Tetrasodium Salt (TMT)

Part A

Pyridinium Bromide, 61

2-Acetyl-6-bromopyridine, 60, was synthesized by the method of J. E. Parks, B. E. Wagner, and R. E. Holm, *J. Organometal. Chem* 56, 53–66 (1973). 2-Acetyl-6-bromopyridine (20.0 g, 100 mmol) was treated with bromine (6.2 mL, 0.12 mol) at reflux in 200 mL of $CHCl_3$ for 45 min. The solution was cooled to room temperature then washed with dilute aqueous $NaHCO_3Na_2S_2O_3$. The organic phase was dried over $Na_2SO_4$, filtered, and evaporated to give an oil. The oil was dissolved in 200 mL of THF and 30 mL of pyridine was added. The resulting solution was refluxed for 30 min. The mixture was cooled and filtered to give 26.1 g of off-white powder (73%): mp 256° C. dec (discolors at 245° C.). Anal. Calcd. for $C_{12}H_{10}Br_2N_2O$: C, 40.26; H, 2.82; N, 7.82. Found: C, 40.12; H, 2.85; N, 7.79. The NMR and IR spectra were consistent with the assigned structure and the product was homogeneous by TLC.

Part B

Chalcone, 62

Potassium hydroxide (18.2 g, 325 mmol) was dissolved in 100 mL of $H_2O$, and 100 mL of methanol was added. 2-Acetyl-6-bromopyridine (65 g, 325 mmol) and (68 g, 650 mmol) of p-anisaldehyde were dissolved together in 400 mL of methanol, and the solution was poured into the KOH solution. Precipitation of product began within a few minutes, and the reaction was allowed to stand at room temperature overnight. The precipitate was collected, washed with isopropanol, and dried to yield 79 g (76%) of the product as a yellow solid, mp 100°–102° C. FDMS (m/e) 317M. An aliquot was purified by column chromatography on Woelm Silica gel, elution with 100% dichloromethane. Anal. Calcd for $C_{15}H_{12}BrNO_2$: C, 56.63; H, 3.80; N, 4.40. Found: C, 56.66; H, 3.87; N, 4.41. The NMR and IR spectra were consistent with the assigned structure and the product was homogeneous by TLC.

Part C

Dibromoterpyridine, 63

Pyridinium bromide 1 (11.3 g, 31.6 mmol) and chalcone 62 (10.0 g, 31.4 mmol) were refluxed in 100 mL of AcOH with 10 g of NH₄OAc for 16 hours. The solution was cooled and filtered, and the solid was washed with AcOH then EtOH to give 13.48 g of white crystals (86%): mp 203°–204.5° C. FDMS (m/e) 495 (M⁺). Anal. Calcd for $C_{22}H_{15}Br_2N_3O$: C, 53,1; H, 3.0; N, 8.5. Found: C, 52.9; H, 3.1; N, 8.4. The NMR and IR spectra were consistent with the assigned structure and the product was homogeneous by TLC.

Part D

Terpyridinediol, 66

Dibromide 63 (7.46 g, 15.5 mmol) in 100 mL of dry THF was added dropwise to a solution of 28.1 mL of 1.6M n-BuLi in 20 mL of dry THF under N₂ over a 12 min period. The temperature was maintained below −75° C. during the addition with a dry ice/acetone bath. The resulting dark green solution was stirred for 10 minutes followed by addition of 7.5 mL of dry DMF over a 2 min period. After 10 min, 90 mL of a 10% HCl solution was added and the resulting solution was stirred for 45 min with continued cooling. The mixture was partitioned between CHCl₃ and H₂O (both solvents pre-cooled to 4° C.) in a separatory funnel. The phases were shaken frequently and allowed to stand at ambient temperature for 15–30 minutes, until the color of the organic phase gradually changed from a greenish hue to golden yellow. The organic phase was washed with sat. NaCl then evaporated to leave a cream-colored residue. This material was triturated with CH₃CN to yield the product as an off-white solid (3.53 g, 60%), mp 225°–227° C. FDMS (m/e) 395M. Anal. Calcd for $C_{24}H_{17}N_3O_3$: C, 72.90; H, 4.33; N 10.63. Found: C, 72.44; H, 4.31; N, 10.46.

The crude dialdehyde (3.53 g, 8.93 mmol) was refluxed with 1 g of NaBH₄ in a mixture of 70 mL of THF and 70 mL of abs. EtOH for 15 min under N₂. After concentration in vacuo, the residue was refluxed for 30 min in dilute NaHCO₃, cooled, filtered, washed with H₂O, then dried to give diol 66 as a white solid (3.35 g, 94.4%). mp 187°–189° C. FDMS (m/e) 400 MH⁺, 399M Anal. Calcd for $C_{24}H_{21}N_3O_3$: C, 72.17; H, 5.30; N, 10.52. Found: C, 71.71; H, 5.20; N, 10.37. The NMR and IR spectra were consistent with the assigned structure and the product was homogeneous by TLC.

Part E

Tetraester, 67

Diol 66 (15.4 g, 38.5 mmol) was suspended in a mixture of 17 mL of Et₃N in 175 mL of CH₂Cl₂ with stirring at 8° C. To this suspension, a solution of(CH₃SO₂)₂O (16.8 g, 96.5 mmol) in 50 mL of CH₂Cl₂ was added dropwise over a 10 min period. The reaction mixture was shaken with water. The organic layer was dried over Mg₂SO₄, filtered, and concentrated nearly to dryness. Addition of EtOAc produced the bismesylate as white crystals which were collected and dried (17.2 g, 80.4%). A mixture of the bismesylate (0.50 g, 0.96 mmol), diisopropylethylamine (0.26 g, 2.0 mmol), and diethyl iminodiacetate (0.38 g, 2.0 mmol) was stirred for 16 hours in 20 mL of dry DMF. The mixture was concentrated in vacuo and the residue was partitioned between Et₂O and H₂O. The Et₂O phase was washed two additional times with water then dried over Na₂SO₄ and evaporated to give the product as a pale yellow oil (0.58 g, 82%). Anal. calcd for $C_{40}H_{47}N_5O_9$: C, 64.76; H, 6.39; N, 9.44. Found: C, 64.35; H, 6.17; N, 9.39. The NMR and IR spectra were consistent with the assigned structure and the product was homogeneous by TLC.

Part F

Nitrotetraester, 68

Terpyridine tetraester 67 (3.27 g, 4.41 mmol) was dissolved in 60 mL of conc. H₂SO₄ to give a red-orange solution. The mixture was cooled to 0° C. and a 1/10 (v/v) mixture of conc. HNO₃ in conc. H₂SO₄ was added such that 4.41 mmol of HNO₃ was delivered. The color of the solution turned pale yellow after addition was completed. The reaction mixture was stirred for 15 min at 0° C., then poured onto crushed ice. Dilute K₂CO₃ was added until pH 8 was reached. The aqueous solution was extracted three times with CH₂Cl₂. The organic layers were combined, dried over Na₂SO₄, and concentrated to give a yellow oil, which was chromatographed on silica gel (5% MeOH/CH₂Cl₂). The fractions containing product were combined and evaporated to give the product which was recrystallized three times from MeOH to yield an off-white solid (1.84 g, 53%): mp 76°–79° C. FDMS (m/e) 787 MH⁺, 786M Anal. calcd for $C_{40}H_{46}N_6O_{11}$: C, 61.06; H, 5.89; N, 10.68. Found: C, 60.69; H, 6.22; N, 11.04. The NMR and IR spectra were consistent with the assigned structure and the product was homogeneous by TLC.

Part G

Aminoterpyridine Tetraester, 69

Nitrotetraester 68 (1.80 g, 2.29 mmol) was dissolved in a mixture of 90 mL of THF and 90 mL of abs. EtOH. Ammonium formate (2.89 g, 45.8 mmol) dissolved in 16 mL of H₂O was added, followed by 4.8 g of 10% Pd/C (4.6 mmol). After stirring at room temperature for 2 h, the reaction was filtered through a diatomaceous earth filter pad. The filter pad was washed well with THF, abs. EtOH, and CH₂Cl₂. The filtrate was concentrated, and the residue was partitioned between CH₂Cl₂ and aqueous NaCl. The organic phase was concentrated then purified on silica gel with 10% MeOH/CHCl₃ to give the product as a straw-colored oil (0.80 g, 46%). FDMS (m/e) 757 MH⁺, 756

M Anal. calcd for $C_{40}H_{48}N_6O_9 \cdot 1/2H_2O$: C, 62.73; H, 6.45; N, 10.97. Found: C, 62.98; H, 6.47; N, 10.67. The NMR and IR spectra were consistent with the assigned structure and the product was homogeneous by TLC.

Part H

Aminotetraacid, 70 (TMT)

Amine tetraester 69 (0.75 g, 0.99 mmol) was stirred with 4 equiv of NaOH in a mixture of 50 mL of MeOH and 2 mL of H₂O for 16 hours at room temperature. The mixture was concentrated to give the product as a solid dihydrate (0.72 g, 94%): FABMS m/e 640 (M⁺ for tetracarboxylate). Anal. calcd. for $C_{32}H_{28}N_6Na_4O_9 \cdot 2H_2O$: C, 50.01; H, 4.20; N, 10.93. Found: C, 49.82; H, 4.12; N, 10.74. The NMR and IR spectra were consistent with the assigned structure and the product was homogeneous by TLC.

Preparation 1a

Alternative Preparation of 4'-Amino-(4-methoxyphenyl)-6,6"-[N,N-di(carboxymethyl)amino-methyl]-2,2':6',2"-terpyridine, Tetrasodium Salt (TMT)

Step 1

2-Acetyl-6-bromopyridine, 60

A 5 L 3-neck flask was charged with 2,6-dibromopyridine (181 g; 0.75 mole) and 2.0 L ether. The suspension was stirred under nitrogen at −60° C. and then n-butyllithium (300 mL; 2.5M) was added from a pressure equalizing dropping funnel over 20 minutes. The bath was lowered and the near solution was allowed to warm to −50° C. After 15 minutes, the dark yellow solution was re-cooled to −78° C. in a dry ice/ether bath and dimethylacetamide (70 g; 0.86 mole) in 70 mL ether was added at such a rate that the temperature did not exceed −75° C. The addition took about one hour for completion, after which the bath was removed to allow the reaction to warm to −60° C. A solution of ammonium chloride (50 g; 0.93 mole) in 150 mL of $H_2O$ was added dropwise over 10 minutes under nitrogen and the temperature rose to −40° C. The mixture was stirred for 45 minutes and the layers were separated. The aqueous layer was back-extracted with 500 mL ether and the pooled organic layers were washed twice with $H_{2O}$ and once with saturated salt solution. The organic layer was dried over $MgSO_4$ and, after evaporating to dryness, gave 150 g of yellow oil. This material, after pooling with another run of the same scale, was kugelrohred at 80° C./0.1 mm Hg to give 257 g (86%) of a near colorless oil that crystallized readily on cooling; silica gel TLC system: 90 hexane: 10 ether.

Step 2

1-[2-(6-Bromo-2-pyridinyl)-2-oxoethyl]pyridinium iodide

To a stirred solution of 2-acetyl-6-bromopyridine (100 g; 0.5 mole) in 600 mL pyridine was added iodine (127 g; 0.5 mole). The mixture was heated on a steam bath for 45 minutes, and the product crystallized on cooling. The solid was filtered and the light yellow crystalline cake was rinsed twice with methylene chloride. After drying, 183 g (90%) was obtained. MP 176°–178° C.; silica gel TLC system: 95 acetone: 5 isopropanol.

Step 3

1-(2-Bromopyridyl)-3-(4-methoxyphenyl)-2-propenone, 62

To a stirred solution of 2-acetyl-6-bromopyridine (50 g; 0.25 mole) in 450 mL methanol was added 4-anisaldehyde (48 g; 0.35 mole). The mixture was cooled in a water bath to 20° C. and then a solution of KOH (18 g; 0.28 mole) in 100 mL $H_2O$ was added rapidly. After about 30 seconds, the product crystallized and the temperature rose to 35° C. The light yellow mixture was stirred for 30 minutes and filtered. The cake was rinsed twice with isopropanol, and after drying, gave 68 g (86% yield). MP 106.1°–106.5° C.; silica gel TLC system: 90 hexane:10 ethyl acetate.

Step 4

6,6"-Dibromo-4'-(4-methoxyphenyl)-2,2':6',2"-terpyridine, 63

A mixture of the chalcone (product of Step 3) (64 g; 0.20 mole), the pyridinium iodide (product of Step 2) (81 g; 0.20 mole) and ammonium acetate (77 g; 1.0 mole) in 600 mL acetic acid was heated at 95° C. for 3 hours and then overnight at 60° C. The reaction mixture was cooled to 15° C. and the crystalline cake was rinsed with $H_2O$ three times. After drying overnight 76.5 g (83%) pale yellow crystalline product was obtained. MP 205°–206° C.; silica gel TLC system: 90 hexane:10 ethyl acetate; $H_2O$ determination :(Karl Fisher) found 0.02% $H_2O$.

Step 5

4'-(4-methoxyphenyl)-2,2':6'2"-terpyridine-6,6"-dicarboxaldehyde

A 3 L flask was charged with 400 mL THF and, while stirring under nitrogen, was cooled in a dry ice/ether bath to −78° C. A solution of n-butyllithium (55 mL; 2.5M) was transferred via nitrogen pump to a pressure equalizing dropping funnel and added to the THF solution. After stirring 15 minutes, the temperature of the mixture was at −78° C. and the solid bis-bromide (product of Step 4) (21 g; 42 mole) was added (Gooch tube) portion wise over an 11 minute period. The temperature did not exceed −75° C. during the addition. Gradually, the suspension changed from brown to brown-green, but solids were still evident after 10 minutes. The bath was lowered and the reaction mixture was allowed to warm to −70° C. over a 10 minute period. The dark green solution was re-cooled to −78° C. and a cold solution (−15° C.) of DMF (dimethyl formamide) (20 mL) in 15 mL THF was added over a three minute period using a nitrogen pump. The temperature rose to −60° C., and, after stirring for 10 minutes, the mixture (−72° C.) was quenched with an aqueous HCl solution (80 mL HCl diluted to 240 mL in $H_2O$) over a ten minute period. During the acid quench, the color turns dark yellow, and that is an indicator of product formation. The temperature rose to −35° C., and the green-yellow sludge was allowed to stir for 45 minutes with no external cooling. The reaction mixture was then quenched into 2 L of $H_2O$ and stirred for 2½ hours. The yellow suspension was filtered through coarse filter paper, and the yellow cake was washed with 400 mL of $H_2O$. After drying overnight, the recovery of crude crystalline product ranged from 72–79%. A purified sample (crystallized from ethyl acetate), had a melting point of 228°–229° C.; silica gel TLC system: 94 toluene:4 methanol:2 isopropylamine.

Step 6

6,6"-Bis(Hydroxymethyl)-4'-(4-methoxyphenyl)-2,2':6',2"-terpyridine, 66

To stirred suspension of the bis-aldehyde from Step 5 (18.5 g; 46.8 mmoles) in 250 mL absolute ethanol at room temperature was added, portion wise, $NaBH_4$ (2.3 g; 60.8 mmoles) over about 10 minutes. Refluxing the mixture for 15 minutes gave a yellow solution, which was stirred for an additional 30 minutes and then diluted with 150 mL $H_2O$. A precipitate developed. After stirring for one and one-half hours, the mixture was filtered. The light tan crystals, after drying, weighted 16 g (86% yield). The crude crystalline product was used without further purification in the next step. MP 140°–141° C.

Step 7

Bismesylate of terpyridine of Step 6

A suspension of the bis(hydroxymethyl)terpyridine from Step 6 (15.4 g; 38.5 mmoles) in 175 mL $CH_2Cl_2$ and triethylamime (17 mL; 120 mmoles) was stirred and cooled to 8° C. A solution of methanesulfonic anhydride (16.8 g; 96.5 mmoles) in 50 mL $CH_2Cl_2$ was added dropwise over 10–15 minutes. The mixture gradually went into solution and, near the end of the addition, a color change from red-orange to yellow-green was observed. A silica gel TLC (toluene:MeOH:isopropylamine—92:6:2.) taken shortly afterwards showed no starting material and a single spot. The mixture was quenched into 200 mL $H_2O$, and the layers, were separated. The aqueous layer was extracted with $CH_2Cl_2$ and the pooled organic layers were washed with $H_2O$. Filtration through a pad of $MgSO_4$ and ¾" silica gel gave a near colorless filtrate that was concentrated to dryness. The crude mixture was diluted with ethyl acetate and the crystalline slurry was cooled and filtered. After drying overnight, 17.2 g (82%) of white crystals were obtained. MP 190°–192° C.

Step 8

Tetraester, 67

To a solution of the bis-mesylate of Step 7 (32.5 g; 58.5 mmoles) in 180 mL N-methylpyrrolidinone (NMP) and ethyldiisopropylamine (17 g; 131 mmoles) was added diethyl iminodiacetate (25 g; 131 mmoles). The mixture was heated on the steam bath for 35 minutes and then stirred overnight at room temperature. After quenching into 300 mL of $H_2O$, the mixture was extracted with ethyl acetate (2×250 mL) and then washed with $H_2O$. The organic layer was concentrated in vacuo and dried under high vacuum to give a light red syrup (51.7 g). An NMR spectrum (DMSO) was consistent for the desired product, plus NMP. The crude syrup was filtered through a short silica gel column, and elution with ether:hexane—80:20 gave a clear colorless syrup (41 g) that was pure by TLC (ether:hexane:triethylamine—60:38:2.).

Step 9

Nitrotetraester, 68

A solution of the tetraester of Step 8 (tetraester 67) (3.1 g; 40.6 mmoles) in 160 mL of trifluoroacetic acid was cooled to 15° C., and potassium nitrate (4.4 g; 44 mmoles) was added in one portion. The mixture was stirred for several minutes, and then concentrated $H_2SO_4$ (22 g; 230 mmoles) was added dropwise over a 15 minute period. A slight exotherm was observed. At the end of the addition, the temperature had risen to 20° C. The light yellow mixture was stirred for 30 minutes and a TLC sample showed no starting material. Most of the trifluoroacetic acid was recovered by distillation under reduced pressure and the residue was decanted into 500 mL of 10% $K_2CO_3$ and 250 mL of ethyl acetate. The layers were separated and re-extracted with ethyl acetate. The combined organic layers were washed with $H_2O$, then salt solution, and then dried over $MgSO_4$. The filtrate was concentrated to near dryness, and then dissolved in 90 mL hot absolute ethanol. The mixture was cooled in an ice bath, and the crystals were collected by filtration and rinsed with ethanol. After drying overnight under vacuum, 29 g (90%) of white crystalline product was obtained. MP 81°–82° C.; TLC system: 70 ether:25 hexane:5 triethylamine.

Step 10

Aminoterpyridinetetraester, 69

To a solution of nitrotetraester 68 (product of Step 9) (28.3 g; 36 mmoles) in 700 mL 1:1THF/absolute ethanol under argon was added 10% Pd/C (10 g; 10 mmoles). After stirring several minutes, a solution of ammonium formate (9.4 g; 149 mmoles) was added dropwise over 3–5 minutes. Within 10 minutes there was some frothing at the vortex of the stirrer and a mild exotherm from 22° C. to 28° C. was noted. A TLC indicated the reaction was about 70% complete after 1 hour. The reaction was stirred for an additional hour and then refluxed on a steam bath for ½ hour. Stirring was continued for another 1 hour and then the reaction mixture was cooled to 20° C. The mixture was carefully filtered through a pad of Solka Floc and the catalyst was rinsed with a total of 400 mL of absolute ethanol. The pale yellow filtrate was evaporated to dryness under vacuum and 25.3 g (95% recovery) was obtained. Further rinsing of the catalyst with 150 mL DMF gave, after evaporation, another 1.4 g of dark syrup (5% recovery) that was not significantly different from the product of the alcohol rinse. The pooled material was purified by flash chromatography using a column that was packed (4.5" wide×2.5" high) with silica gel 60 (EM Science) under nitrogen with hexane containing 1% triethylamine. The material was dissolved in a minimum amount of toluene and applied to the top of the column. The column was eluted with 30:70 ether/hexane and the flow rate was adjusted to about 100 mL/minute. Gradually increasing the polarity to 70:30 ether/hexane and 1% triethylamine gave a total of about 15 g of colorless syrup that was a single spot by TLC. (TLC system—ether:hexane:methanol:triethylamine—70:25:4:1).

Step 11

TMT, 70

To a solution of the amino terpyridinetetraester 69 of Step 10 (39.,0 g; 51.5 mmoles) in 450 mL of absolute ethanol was added a solution of NaOH (8.39 g/100 mL of triple distilled $H_2O$). After stirring for about 1 minute, the clear pale yellow solution became turbid, and, gradually, a precipitate developed. The mixture was filtered after two hours, and the resulting light yellow solid was rinsed twice with ethanol and once with hexane. Examination under a polarizing microscope confirmed a crystalline structure. The solid was dried in the vacuum oven for 15 hours; 33.9 g (90% yield) was obtained. NMR, IR and UV spectra were consistent with the assigned structure, and the product was homogeneous by TLC [PAW 40: acetone 10 (PAW=pyridine 54: acetic acid 16: water 30)]. Karl Fisher ($H_2O$) found 6.18% $H_2O$ ; MP>290° C.; gas chromatography (solvent residue) found 0.07% ethanol.

Preparation 2

Preparation of 4'-(3-amino-4-methyoxyphenyl)-6.6"-bis(N'N'-dicarboxymethyl-N-methylhydrazino)-2, 2':6',2"-terpyridine, tetrasodium salt (THT), 65

Part A 6,6"-Bis(N-methylhydrazino)-4'-(4-methoxyphenyl)-2,2':6',2"-terpyridine 6,6"-Dibromo-4'-(4-methoxyphenyl)-2,2':6',2"-terpyridine, 63, (1.0 g, 2 mmol) was refluxed in 20 mL of methylhydrazine for 16 hours under nitrogen. The solution was cooled, and the resulting precipitate filtered, and dried to a constant weight to give 0.68 g of cream-colored solid, mp 218°–220° C. FDMS (m/e) 428 MH⁺, 427M⁺. Anal. calcd for $C_{24}H_{25}N_7O$. 0.25 $H_2O$: C, 66.72; H, 5.96; N, 22.70. Found: C, 66.85; H, 5.85; N, 23.0. The NMR and IR spectra were consistent with the assigned structure.

Part B 6,6"-Bis(N',N'-di(ethoxycarbonylmethyl)-N-methylhydrazino)-4'-(4-methoxyphenyl)-2,2':6',2"-terpyridine The bis(methylhydrazine)terpyridine of Part A (3.50 g, 82 mmol), ethyl bromoacetate (13.2 mL, 820 mmol), 2,6-lutidine (9.6 mL, 820 mmol), and sodium iodide (0.35 g, 2 mmol) were added to 350 mL of acetonitrile, and the solution was refluxed under N2 for 48 hours, when an additional 4.1 mL (370 mmol) of ethyl bromoacetate and 4.8 mL (410 mmol) of 2,6-lutidine were added. The reaction solution was refluxed for an additional 48 hours, and cooled. A copious amount of white salt resulting from excess bromoacetate and lutidine was filtered and discarded. The filtrate was concentrated, and the concentrated material was dissolved in dichloromethane, and extracted two times with dilute aqueous sodium chloride. The organic phase was concentrated under high vacuum until free of odors of bromoacetate and lutidine. The crude oil was purified on a Woelm silica gel column (36×2 in.). The column was eluted initially with 100% dichloromethane followed by 50/1 dichloromethane/acetone, with gradual increase of the concentration of acetone to 25/1 dichloromethane/acetone. Concentration of purified fractions gave 2.91 g (46%) of light straw-colored oil. A fraction of the purified oil, upon standing at room temperature, crystallized, and after trituration with methanol gave a white solid, mp 100°–103° C. Anal. calcd for $C_{40}H_{49}N_7O_9$: C, 62.24; H, 6.40; N, 12.70. Found: C, 62.31; H, 6.32; N, 12.69. The NMR and IR spectra were consistent with the assigned structure, and the product was homogeneous by TLC.

Part C 6,6"-Bis(N',N'-di(ethoxycarbonylmethyl)-N-methylhydrazino)-4'-(4-methoxy-3-nitrophenyl)-2,2':6',2"-terpyridine The terpyridine tetraester of Part B (0.659 g, 0.84 mmol) was dissolved in 5 mL of conc $H_2SO_4$ to give a red-orange solution. The mixture was cooled to 0° C., and a mixture of conc $HNO_3$ in conc $H_2SO_4$ was added such that 0.84 mmol of $HNO_3$ was delivered. The color of the solution turned pale yellow after addition was completed. The reaction mixture was stirred for 15 minutes at 0° C., then poured onto crushed ice. Dilute $K_2CO_3$ was added until pH 8 was reached. The aqueous solution was extracted three times with $CH_2Cl_2$. The organic layers were combined and dried over $Na_2SO_4$, and concentrated to give a yellow oil, which was chromatographed on silica gel (20/1 methylene chloride/acetone). The fractions containing product were combined and evaporated to give the product, a pale yellow glass. Yield 0.15 g (22%). Anal. calcd for $C_{40}H_{48}N_8O_{11}$: C, 58.82; H, 5.92; N, 13.72. Found: C, 58.76; H, 5.61; N, 13.84. FDMS (m/e) 816M. The NMR and IR spectra were consistent with the assigned structure, and the product was homogeneous by TLC.

Part D

4'-(3-Amino-4-methoxyphenyl)-6,6"-bis(N',N'-di(ethoxycarbonylmethyl)-N-methylhydrazino)-2,2':6',2"-terpyridine The nitrotetraester of Part C (0.72 g, 0.88 mmol) was dissolved in a mixture of 30 mL of THF and 30 mL of ethanol. Ammonium formate (1.08 g, 17.1 mmol) dissolved in 6 mL $H_2O$ was added, followed by 1.8 g of 10% Pd/C (1.7 mmol). After stirring at room temperature overnight, the reaction was filtered through a diatomaceous earth filter pad. The filter pad was washed well with THF, absolute EtOH, and $CH_2Cl_2$. The filtrate was concentrated, and the residue was dissolved in chloroform, and the chloroform solution was washed two times with water. The organic phase was concentrated to an oil. Addition of methanol to the oil resulted in crystallization of the oil. The material was slurred in 20 mL of methanol, and filtered, and air dried to yield 0.64 g of cream colored solid (92.7%). Anal. calcd for $C_{40}H_{50}N_8O_9$: C, 61.06, H, 6.40; N, 14.24. Found: C, 60.74; H, 6.39; N, 14.01. The NMR and IR spectra were consistent with the assigned structure and the product was homogeneous by TLC.

Part E

4'-(3-Amino-4-methoxyphenyl)-6-6"-bis(N',N'-dicarboxymethyl-N-methylhydrazino)-2,2':6',2"-terpyridine, tetrasodium salt (THT), 65

The amine tetraester of Part D (0.60 g, 0.76 mmol) was stirred with 4 equivalents of NaOH in a mixture of 25 mL of MeOH and 1 mL of $H_2O$ for about 16 hrs at room temperature. The mixture was concentrated to give a quantitative yield of solid tetracarboxylate. Anal. calcd for $C_{32}H_{30}N_8Na_4O_9 \cdot 2H_2O$: C, 48.12; H, 4.29; N, 14.03. Found: C, 48.01; H, 3.97; N, 12.77.

Preparation 3

Preparation of 6,6"-Bis(N',N'-di-carboxymethyl-N-methylhydrazino)-4'-(3-isocyanato-4-methlxyphenyl)-2,2':6',2"-terpyridine. Sodium Salt The THT amine tetrasodium salt of Preparation 2, Part E (0.39 g, 0.51 mmol) was dissolved in 80 mL of methanol. At room temperature, 0.58 g (0.50 mmol) of thiophosgene in 1.0 mL tetrahydrofuran was added, followed by addition of 0.51 g (0.50 mmol) of triethylamine in 1.0 mL of tetrahydrofuran. The reaction was then concentrated to a residue, which was slurried in dichloromethane, and filtered to yield 0.26 g (65%) of yellow solid. The infrared spectrum was consistent with the assigned structure. The product was believed to be the monocarboxylic acid trisodium salt.

Preparation 4

Preparation of 5-Amino-2,9-Bis[N,N-di-(carboxymethyl)aminomethyl]-1,10-phenanthroline. Tetrasodium Salt Part A 2,9-Dimethyl-5-nitro-1,10-phenanthroline Neocuproine hydrochloride, hemihydrate (25.0 g, 99 mmol) was dissolved in 100 mL of concentrated nitric acid. 200 mL of concentrated sulfuric acid was added, and the reaction was heated at reflux for 2.5 hours, and then allowed to stand at room temperature for 8 days. The reaction mixture was then gradually added to a mixture of about 3 Kg of ice and 351 g (8.8 mole) of $LiOH \cdot H_2O$, while stirring with a glass rod. During the neutralization procedure, ice was added as necessary so that unmelted ice was always present during the neutralization, and the neutralization reaction was also simultaneously cooled by an acetone/ice bath. After the addition was completed, the pH of the reaction mixture was 12. The aqueous mixture was extracted two times with methylene chloride, first with 1000 mL, and then with 400 mL. The methylene chloride fractions were combined, and extracted once with 500 mL of distilled $H_2O$. The methylene chloride phase was concentrated to a residue, and triturated with 500 mL of acetonitrile. The solid was filtered, washed with acetonitrile, and dried under vacuum to give 10.3 g of cream yellow solid, which was dissolved in 100 mL of refluxing acetonitrile, allowed to crystallize at room temperature, and was filtered to give 8.5 g (34%) of cream-yellow crystals, mp 184°–186° C. FDMS (m/e) 253M Anal. calcd for $C_{14}H_{11}N_3O_2 \cdot 0.25\ H_2O$: C, 65.23; H, 4.50; N, 16.30. Found: C, 65.57; H, 4.45; N, 16.27. The NMR and IR spectra were consistent with the assigned structure and the product was homogeneous by TLC.

Part B 2,9-Di(bromomethyl)-5-nitro-1,10-phenanthroline 2,9-Dimethyl-5-nitro-1,10-phenanthroline (1.0 g, 4 mmol) and N-bromosuccinimide (1.42 g, 8 mmol) were mixed together into a homogeneous mixture in a beaker, and added all at once to 20 mL of refluxing (181° C.) o-dichlorobenzene. The heating was continued at the reflux temperature for 2 minutes, and then the reaction was allowed to cool to room temperature. The reaction mixture was purified on a column (18×2 in.) of Woelm silica gel, by elution with 100% dichloromethane, to give 0.47 g (29%) of purified material, a yellow oil. Rf on TLC, 0.5 (40/1 $CH_2Cl_2$/acetone). Trituration of an aliquot of the purified product gave a gray-white solid, which decomposed at 146° C. Anal. calcd for $C_{14}H_9Br_2N_3O_2 \cdot 0.5\ H_2O$: C, 40.02; H, 2.39; N, 10.00. Found: C, 40.36; H, 2.67; N, 9.77. FDMS (m/e) 409 M The NMR and IR spectra were consistent with the assigned structure.

Part C 2,9-Bis [N,N-di(ethoxycarbonylmethyl) aminomethyl]-5-nitro-1,10-phenanthroline 2,9-Di(bromomethyl)-5-nitro-1,10-phenanthroline (2.28 g, 5.5 mmol) and 2.08 g (11 mmol) of 1,8-bis (dimethylamino)naphthalene were dissolved together in 25 mL of 1-methyl-2-pyrrolidinone, and 2.08 g (11 mmol) of diethyl iminodiacetate was added. The reaction was sealed with a ground glass stopper, and after approximately 10 minutes of stirring at room temperature, white precipitate began forming. The reaction was then placed in the refrigerator (at 4° C.) and stored for about 20 hours. The reaction mixture was partitioned between 400 mL of diethyl ether and 400 mL of distilled $H_2O$ and the ether fraction was extracted a total of 5 times with 400 mL portions of distilled $H_2O$. The ether phase was concentrated and dissolved in 400 mL of methylene chloride. The methylene chloride phase was extracted once with distilled $H_2O$, dried with a mixture of Celite diatomaceous earth and sodium sulfate, filtered, and then concentrated to a dark oil. A column of Woelm silica gel was prepared in 10/1 methylene chloride/methanol (20 inches in height by 2 inches in diameter), and the crude oil was applied to the column in methylene chloride. About 50 mL of methylene chloride was applied to the column, and then the column was eluted with 10/1 $CH_2Cl_2$/methanol. Fractions (100 mL each) were collected, and the fractions of pure product as observed by TLC (10/1 methylene chloride/methanol, Rf 0.4) were combined and concentrated to yield 1.17 g (34%) of product as an oil of reddish-amber hue. FDMS (m/e) 628 MH$^+$. Anal. calcd for $C_{30}H_{37}N_5O_{10} \cdot 2H_2O$: C, 54.29; H, 6.23; N, 10.55. Found: C, 54.71; H, 5.58; N, 10.53. The NMR and IR spectra were consistent with the assigned structure.

Part D

5-Amino-2,9-bis[N,N-di(ethoxycarbonylmethyl) aminomethyl]-1,10-phenanthroline 2,9-Bis[N,N-di(ethoxycarbonylmethyl)aminomethyl]-5-nitro-1,10-phenanthroline (3.37 g, 5.4 mmol) was dissolved in a solution of 100 mL tetrahydrofuran and 200 mL absolute ethanol. A solution of 6.8 g (108 mmol) of ammonium formate in 22 mL of distilled $H_2O$ was added, followed by 5.72 g of palladium on carbon (10%) (50% wet with water for safety). The reaction was stoppered with a gas bubbler, stirred at room temperature for 30 minutes, and then filtered through a diatomaceous earth filter pad. The solvents were then removed on a rotary evaporator. The residue was dissolved in 300 mL of dichloromethane which was then extracted with 300 mL of distilled water. The organic phase was extracted with 300 mL of saturated sodium chloride, dried with a mixture of Celite diatomaceous earth and sodium sulfate, filtered, and then concentrated under high vacuum to a dark amber oil which weighed 2.90 g. The oil was treated with 9.0 mL of propionitrile to induce the crystallization of a yellow solid. The solid was filtered, washed with 13 mL of propionitrile, 15 mL of hexanes, and then air dried to a constant weight of 1.04 g (32%); mp 137°–139° C. FDMS (m/e) 598 MH$^+$, 597 M. Anal. calcd. for $C_{30}H_{39}N_5O_9 \cdot H_2O$: C, 58.52; H, 6.71; N, 11.38. Found: C, 58.28; H, 6.55; N, 11.53. The NMR and IR spectra were consistent with the assigned structure.

Part E

5-Amino-2,9-bis[N,N-di(carboxymethyl) aminomethyl]-1,10-phenanthroline, Tetrasodium Salt 5-Amino-2,9-bis[N,N-di(ethoxycarbonylmethyl) aminomethyl]-1,10-phenanthroline (0.90 g, 1.5 mmol) was dissolved in 200 mL of methanol. Sodium hydroxide (0.25 g, 6.25 mmol) dissolved in 10.0 mL of distilled $H_2O$ was added. The reaction flask was stoppered and the reaction mixture was stirred magnetically for 24 hours at room temperature. The solvent was removed by rotary evaporation. The solid residue was triturated with methylene chloride and filtered to yield 0.81 g (94%). The tetrasodium salt was hygroscopic, and a significant amount remained adhered to the glass wall of the filtration funnel. Anal. calcd for $C_{22}H_{19}Na_4N_5O_8 \cdot 3H_2O$: C, 42.11; H, 4.02; N, 11.16. Found: C, 42.01; H, 3.71; N, 11.03; The IR and spectrum and FAB mass spectrum were consistent with the assigned structure.

Preparation 5

Preparation of 2,9-Bis[N,N-di(carboxy-methyl) aminomethyl]-5-isothiocyanato-1,10-phenanthroline, Sodium Salt 5-Amino-2,9-bis[N,N-di(carboxymethyl)aminomethyl]-1,10-phenanthroline, tetrasodium salt (0.16 g, 0.28 mmol) was dissolved in a solvent mixture of 20 mL methanol/4 mL distilled $H_2O$. Thiophosgene (0.28 mmol, i.e., 1.0 mL of a solution of 0.32 g thiophosgene in 10.0 mL THF) was added, followed immediately 0.28 mmol of triethylamine (1.0 mL of a solution of 0.28 g of triethylamine in 10.0 mL THF). The reaction was stirred at room temperature, and then immediately concentrated. A residue of 0.16 g (94%) of yellow solid was isolated. The IR spectrum was consistent with the assigned structure.

Preparation 6

Preparation of 6,6"-[N,N-di(carboxy methyl) aminomethyl]-4'-(3-isothiocyanato-4-methoxyphenyl)-2,2'-6',2"-terpyridine, Tetrasodium Salt TMT, 70, of Preparation 1 (0.31 g, 0.42 mmol) was dissolved in 30 mL of methanol. One milliliter of THF containing 0.42 mmol of thiophosgene was added followed by 1.00 mL of THF containing 0.42 mmol of triethylamine. The reaction solution was immediately concentrated to a residue which was then triturated with triethylamine. The solid was collected by filtration and washed with dichloromethane to give 0.30 g of product. The IR spectrum was consistent with the assigned structure.

Prescription 7

Trisodium 15-amino-3,5,6,8,9,11-hexahydro-4,7,10-tris(carboxymethyl)-2,17:12,14-dietheno-1,4,7,10,13-pentaazabenzocyclopentadecine

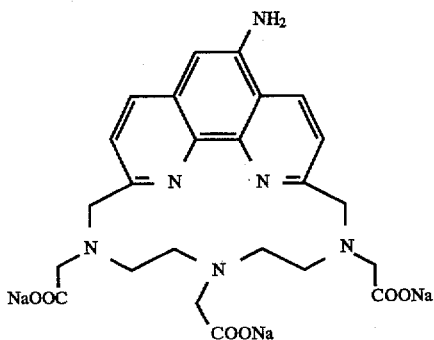

Part A.

3,5,6,8,9,11-Hexahydro-15-nitro-4,7,10-tris(p-toluenesulfonamido)-2,17:12,14-dietheno-1,4,7,10,13-pentaazabenzocyclopentadecine

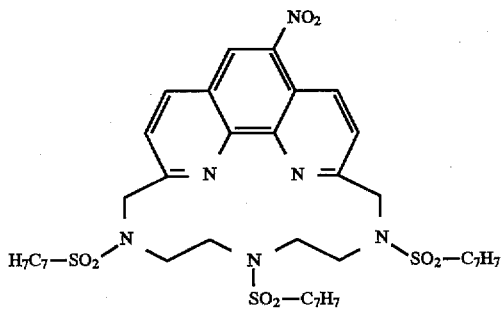

100 mL of N-methylpyrrolidin-2-one containing 2% by weight of 2,9-bisbromomethyl-5-nitro-1,10-phenanthroline prepared in Preparation 4, Part B is added via a syringe pump over 2 hours into 20 mL of magnetically stirred N-methylpyrrolidin-2-one which is held under argon at 20° C. Simultaneously, a 2% solution in N-methylpyrrolidin-2-one of one equivalent of the disodium salt of diethylenetriamine N,N',N"-tri-p-toluenesulfonamide is added. The reaction is stirred for 6 additional hours after the addition at 20° C., 200 mL of the solvent is then distilled under high vacuum, the residual solution is cooled and added to 100 mL of ice water. The resulting precipitate is isolated by filtration, washed with cold water, and triturated with acetonitrile to provide the crude tri-p-toluenesulfonamide derivative.

Part B.

3,4,5,6,7,8,9,10,11-Nonahydro-15-nitro-2,17:12,14-dietheno-1,4,7,10, 13-pentaazabenzocyclopentadecine

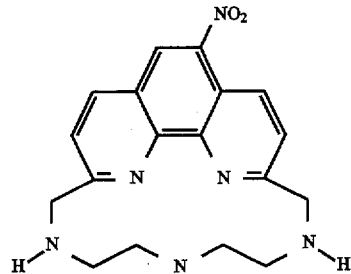

One part of crude macrocycle prepared in Part A is dissolved in 10 parts of concentrated sulfuric acid (96%), and the reaction mixture is stirred and heated to 110° C. under argon. After 24 hours, the solution is cooled with vigorous stirring in an ice water bath and is treated with 10% sodium hydroxide solution until the pH reaches 10. The aqueous phase is extracted five times with equal volumes of chloroform, the extracts are combined and are dried over anhydrous sodium sulfate. The salts are then removed by filtration, and the filtrate is evaporated under argon. The crude triamine can be purified by crystallization from ethanol/water.

Part C.

3,5,6,8,9,11-Hexahydro-15-nitro-4,7,10-tris(ethoxycarbonylmethyl)-2,17:12,14-dietheno-1,4,7,10,13-pentaazabenzocyclopentadecine

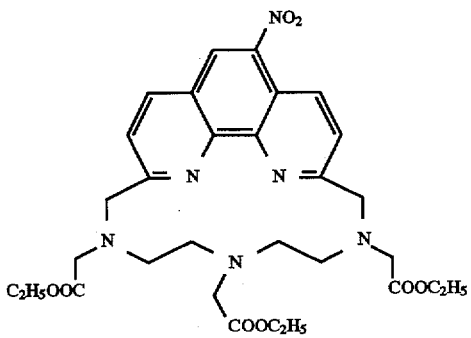

A mixture of one part of the triamino macrocycle prepared in Part B with 10 parts of sodium carbonate and 3 parts of ethyl bromoacetate as a 3 percent by weight solution in anhydrous acetonitrile is stirred under argon for 24 h at 60° C. The reaction mixture is then cooled to room temperature, filtered, and the solvent is evaporated. The residue can be further purified by trituration in cold ether.

Part D.

15-Amino-3,5,6,8,9,11-hexahydro-4,7,10-tris
(ethoxycarbonylmethyl)-2,17:12,14-dietheno-1,4,7,
10,13-pentaazabenzocyclopentadecine

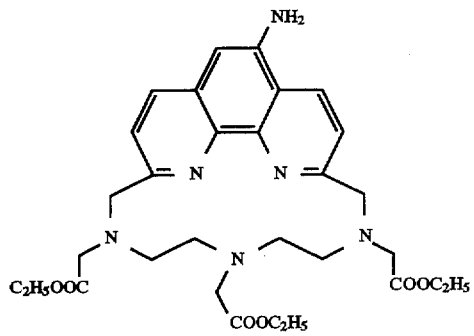

One part by weight of the nitrotriester of Part C is dissolved in 100 parts by weight of a 50/50 mixture of tetrahydrofuran (THF) and ethanol. Two equivalents of ammonium formate in six times the weight of water is added followed by 2 equivalents of 10% Pd/C. The reaction mixture is stirred at room temperature overnight under argon. Then the reaction mixture is filtered under argon, and the filtered catalyst is washed well with THF, ethanol, and then dichloromethane under argon. The combined filtrate and washings are concentrated, the residue is dissolved in chloroform, and the choroform solution is washed twice with water. The organic phase is concentrated to an oil, and crystallization is promoted by the addition of methanol. The product is triturated in methanol, filtered, and then dried in air.

Part E.

Product A.

The amine triester of Part D is stirred at room temperature with three equivalents of sodium hydroxide in 5% aqueous methanol for 24 h. The solvent is removed under vaccuum and the product (A) is triturated with a little cold methanol. The product A is isolated by filtration.

Preparation 8.

Trisodium 15-isothiocyanato-4,7,10-tris
(carboxymethyl)-2,17:12,14-dietheno-1,4,7,10,13-
pentaazabenzocyclopentadecine

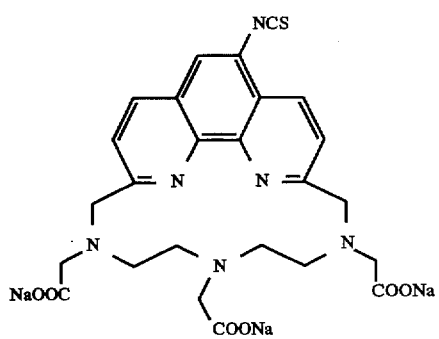

One part by weight of the amine trisodium salt from Preparation 7, Part E, is stirred in 200 parts of methanol at room temperature. This is treated at ambient temperature with one equivalent of thiophosgene dissolved in two parts by weight of tetrahydrofuran followed by one equivalent of triethylamine dissolved in two parts by weight of tetrahydrofuran. After one hour, the reaction mixture is concentrated to a residue, slurried in dichloromethane, and the product is isolated by filtration.

Preparation 9.

Trisodium 2-Methyl-3-thio-4-{15-[3,5,6,8,9,11-
hexahydro-4,7,10-tris(carboxymethyl)-2.17:12,14-
dietheno-1,4,7,10,13-
pentaazabenzocyclopentadecinyl]}-semicarbazide

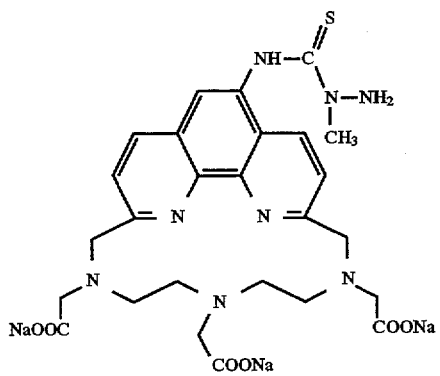

To a freshly prepared and stirred mixture of one part by weight of the trisodium salt of 15-isothiocyanato-4,7,10-tris (carboxymethyl)-2,17:12,14-dietheno-1,4,7,10,13-benzopentaazacyclopentadecine prepared in Preparation 8 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation 10.

Tetarsodium 2-Methyl-3-thio-4-{5-([6,6"-di-bis
(carboxymethyl)aminomethyl]-2:2', 6':2"-terpyridin-
4'-yl)-2-methboxyphenyl}-semicarbazide

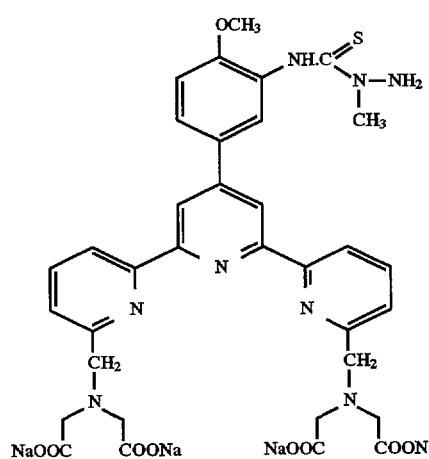

To a freshly prepared and stirred mixture of one part by weight of the tetrasodium salt of the TMT-isothiocyanate prepared in Preparation 6 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation 11.

Tetrasodium 2-methyl-3-thio-4-{5-([6,6"-bis(N',N'-dicarboxymethyl-N-methylhydrazino)-2:2', 6:2" terpyridines-4'-yl]-2-methoxyphenyl)}semicarbazide

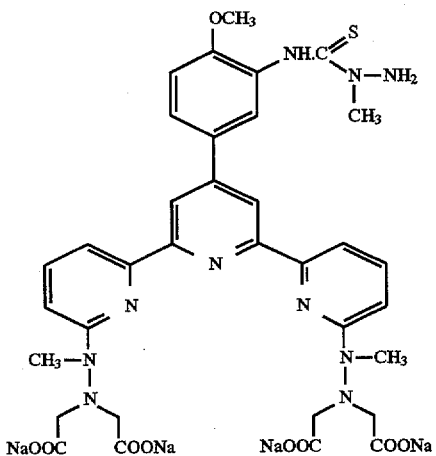

To a freshly prepared and stirred mixture of one part by weight of the tetrasodium salt of the THT-isothiocyanate prepared in Preparation 3 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation 12.

Tetrasodium 2-Methyl-3-thio-4-[2,9-di-bis (carboxymethyl)aminomethyl-1,10-phenanthrolin-5-yl]semicarbazide

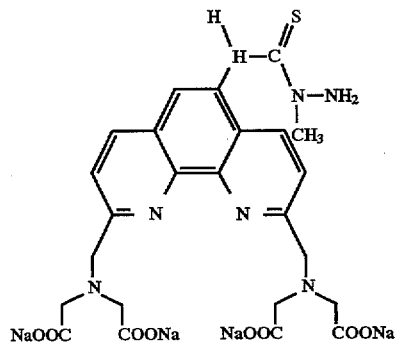

To a freshly prepared and stirred mixture of one part by weight of the tetrasodium salt of the PheMT-isothiocyanate prepared in Preparation 5 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation 13.

Macrocyclic Chelator: Disodium 1,7-dicarboxymethyl-[4'-(3-amino-4-methoxyphenyl)-2, 2':6'2"-terpyridino]-1,4,7,10,13,16-hexzaa-18-crown-6

Part A 6,6"-Dicyano-4"-(4-methoxyphenyl)-2,2':6',2"-terpyridine

A mixture of 6,6"-dibromo-4'-(4-methoxyphenyl)-2,2':6', 2"-terpyridine (0.0745 mol), cupurous cyanide (0.296 mol), sodium cyanide (0.297 mol), and 300 mL of dimethylformamide is allowed to react at 160° C. for 6 h. After cooling, the reaction mixture was transferred into 1500 mL of water and the resulting mixture is stirred for 2 h and filtered. The solid residue is dissolved in a solution of sodium cyanide (200 g in 400 mL water) and the resulting solution is stirred overnight. The desired solid product is filtered, triturated with water (6×600 mL), and dried to yield a white powder.

Part B.

6,6"-Bis(aminomethyl)-4'-(4-methoxyphenyl)-2, 2':6'2"-terpyridine

A mixture of 6,6"-dicyano-4'-(4-methoxyphenyl)-2,2':6', 2"-terpyridine (4 mmol) and 480 mg 10% Pd/C in 130 mL of acetic acid is hydrogenated (H$_2$, 50 psi) at 45° C. for 22 h. The reaction mixture is filtered and the solvent is stripped to yield the desired diamine as the acetate salt, which is triturated with methanol followed by removal of solvent and drying to yield the desired diamine acetate.

Part C.

6,6"-Bis(aminomethyl)-4'-(4-methoxyphenyl)-2, 2':6'2"-terpyridine pyridine-2,6-dicarboxylic acid cyclic dilactam

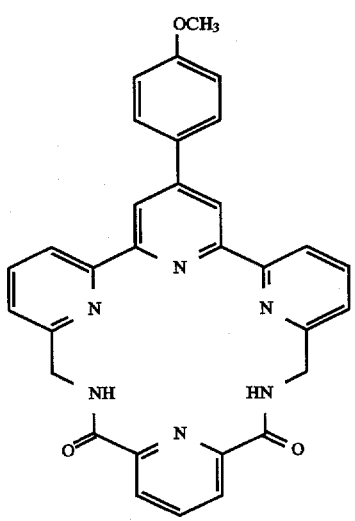

13(a)

A solution of 6,6"-bis(aminomethyl)-4'-(4-methoxyphenyl)-2,2':6'2"-terpyridine (2 mmol) in tetrahydrofuran (41 mL) and a solution of diisopropylamine (4 mmol) in dimethylformamide (9 mL) are added with stirring into 350 mL of THF. To the above solution is added dropwise a solution of 2,6-pyridinedicarbonyl chloride in THF (50 mL) and the reaction mixture is stirred overnight. The solvents are distilled under diminished pressure and the residue dissolved in 250 mL of $CH_2Cl_2$. The organic layer is washed successively with water (2×30 mL), 0.01N HCl solution (2×25 mL), water (1×20 mL), 5% $NaHCO_3$ solution (2×25 mL), and water (2×20 mL). After drying ($Na_2SO_4$), the solvent is distilled to yield the desired dilactam which is then purified by silica gel chromatography.

Part D.

Disodium 1,7-dicarboxymethyl-[4'-(3-amino-4-methoxyphenyl)-2,2':6'2"-terpyridino]-1,4,7,10,13,16-hexaaza-18-crown-6

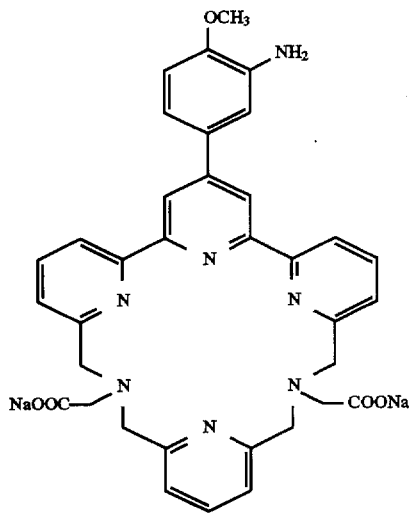

13(b)

The cyclic dilactam (a) of Part C above is reduced with diborane to provide the diamine which is reacted with ethyl bromoacetate to provide the bis(ethyl acetate). This is then nitrated with nitric acid and sulfuric acid to provide the 4'-(4-methoxy-3-nitrophenyl)-2,2':6'2"-terpyridinyl derivative. The nitro group is then reduced with ammonium formate in the presence of palladium on carbon, and the ester groups are saponified with sodium hydroxide to provide the desired macrocyclic chelate (b).

Preparation 14.

Macrocyclic Chelator: Trisodium 1,4,7-tris(carboxymethyl)-[4'-(3-amino-4-methoxyphenyl)-2,2':6',2"-terpyridino]-1,4,7,10,13,16-hexaaza-18-crown-6

Part A.

Terpyridine-hexa-azacyclic tritoluenesulfonamide

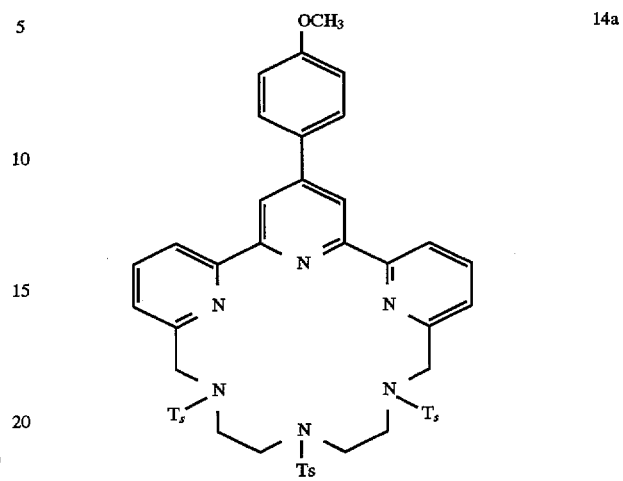

14a

To a solution of 6,6"-bis(mesyloxymethyl)-4'-(4-methoxyphenyl)-2,2':6'2"-terpyridine (2 mmol) in 60 mL of DMF/acetonitrile,(1:1), which is warmed to 80° C. under nitrogen, is added, in portions, a solution of N,N',N"-tritosyl-(N,N-bisaminoethyl)amine disodium salt in 20 mL of DMF. The reaction mixture is allowed to react at 80° C. for 7 h and the solvents are distilled under diminished pressure. The residue is dissolved in 150 mL of methylene chloride; the organic layer is washed with water, dried, and the solvent then distilled under diminished pressure to yield crude terpyridine-hexaaza cyclic tritoluenesulfonamide, 14(a). The desired tritoluenesulfonamide is purified by column chromatography (silica gel).

Part B.

Trisodium 1,4,7-tris(carboxymethyl)-[4'-(3-amino-4-methoxyphenyl)-2,2':6'2"-terpyridino]-1,4,7,10,13,16-hexaaza-18-crown-6

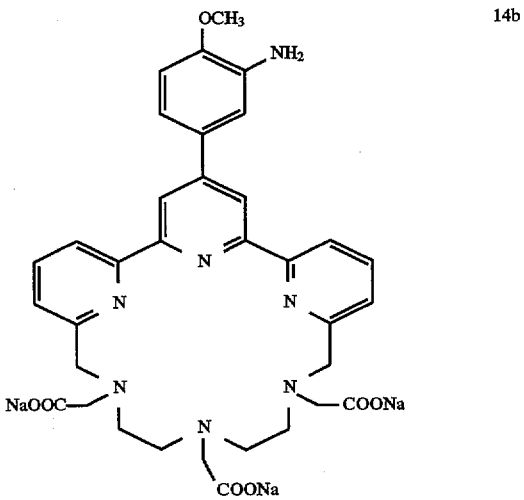

14b

The tritoluenesulfonamide, 14(a), of Part A above is hydrolyzed in sulfuric acid to remove the toluenesulfonamide groups and provide the macrocyclic terpyridinyl triamine derivative. This triamine is reacted with ethyl bromoacetate to provide the tris(ethyl acetate). This is nitrated with nitric acid and sulfuric acid to provide the 4'-(4-methoxy-3-nitrophenyl)-2,2':6'2"-terpyridinyl derivative. Then the nitro group is reduced with ammonium formate in the presence of palladium on carbon, and the ester groups are saponified with sodium hydroxide to provide the desired macrocylic chelator 14(b).

SECTION II:

IMMUNOREAGENTS

Preparation of Conjugates of an Antibody with TMT and with THT

Part A

Procedure to Attach Chelator to Antibodies

TMT or THT was attached to antibodies by oxidation of the carbohydrate groups on the antibodies with $NaIO_4$ to produce aldehyde groups on the antibodies. A solution (110 mL) of 0.1M $NaIO_4$ in purified water was added to one mL of a 4 mg/mL solution of B72.3* antibody in PBS (10 mM sodium phosphate, 0.15M NaCl), pH 6.0. The pH of the resulting solution was readjusted to 6.0 and incubated for 1 hour at room temperature in the dark. After this incubation, excess periodate was removed by passing the antibody solution through a Sephadex G50 column that had been equilibrated with PBS, pH 6.0. One mL fractions were collected and the two fractions giving the highest absorbance at 280 nm were pooled.

*B72.3 is a well known antibody to colorectal tumor-associated antigens which was first disclosed by the National Institute of Health (NIH) (U.S. Pat. No. 4,522,918).

A 0.33M solution of each chelating agent (TMT or THT) was prepared by dissolving the solid chelating agent in PBS, pH 6.0. This raised the pH of the solution to over pH 9.0 so the pH was adjusted to about 6.8 with 6M HCl. Two hundred mL of each chelator solution was added to separate 2 mL portions of the antibody solution and the pH of each resulting solution was adjusted to pH 6.0. These mixtures were incubated for 5 h at room temperature in the dark. Then $NaCNBH_3$ (Aldrich 29,694–5; 5M in about 1M NaOH) was added to each solution to a final concentration of 10 mM, and the pH was adjusted to 6.0 to reduce the Schiff base formed by the aldehyde. The mixtures were incubated overnight at room temperature. The solutions were then centrifuged (Eppendorf Model 5412) to remove undissolved chelate that precipitated overnight and were concentrated to 1 mL in a Centricoh 30 (Amicon) microconcentrator. These solutions were passed through Sephadex G50 columns to remove excess chelator and $NaCNBH_3$. One mL fractions were collected and the two fractions of each chelator solution containing the highest absorbance at 280 nm were pooled. The pooled fractions were dialyzed against 0.01M sodium acetate, 0.15M NaCl , pH 6.0 with two changes of buffer. If further precipitates were formed during analysis, they were removed by centrifugation.

Typically, the conjugate preparations produced by this procedure had an average molar ratio of TMT or THT to antibody of about 1.7.

Part B.

Analysis of Ratio of Chelator to Antibody

The concentrations of antibody in the conjugate solutions were determined using the BioRad protein assay using bovine immunoglobulin as the protein standard. The concentration of THT was determined spectrophotometrically using the measured extinction coefficient at 350 nM For TMT-B72.3 conjugate a portion (about 0.5 mg ) of the conjugate was put into 1 mL of 0.01M sodium acetate, 0.15M NaCl buffer, pH 6.0 and an excess of $Eu^{+3}$ was added. The absorbance of this solution at 330 nm was used to determine the amount of chelate in these solutions.

Part C.

In Vitro Functional Test (Immunocompetency Assay) of Antibody-Chelate Conjugate (Immunoreagent)

The wells of Linbro EIA II Plus microtiter plates were coated with antigen by adding 100 mL/well of a solution of 4 mg/mL of bovine submaxillary mucin (Sigma M4503), an antigen reactive with the B72.3 antibody, in PBS (phosphate buffered saline) and incubated for 1 h at room temperature. After washing the plate three times with PBS, pH 6.8, the wells were blocked by adding 200 mL/well of a 1% BSA (bovine serum albumin, Sigma A-7906)-PBS, pH 6.8 solution and incubated for 1 h at room temperature. The plates were again washed three times with PBS, pH 6.8. Samples of the conjugates were prepared at a concentration of $1 \times 10^{-7}$M in PBS, pH 6.8 containing 1% horse serum (Sigma S-7390), and dilutions in this same buffer were made from these solutions. One hundred µL of each sample dilution were added to wells, in duplicate. After a 1 h room temperature incubation, the plates were washed three times with PBS, pH 6.8 and then scored by the addition of 100 µL per well of a 1:1000 dilution of a rabbit anti-mouse F(ab')2-HRP conjugate (Jackson Labs, 315-035-047) in PBS, pH 6.8 containing 1% horse serum. After a 1 h room temperature incubation, the wells were washed three times with PBS, pH 6.8. Color developed upon the addition of 100 µL per well of ABTS-HRP substrate (Kirkegaard and Perry Labs, Product #506502 and 506402). The reaction was stopped by the addition of an equal volume of 4N $H_2SO_4$. The color was read using a 414 nm filter in a Titertek Multiscan instrument after 15 min.

Figure 2:
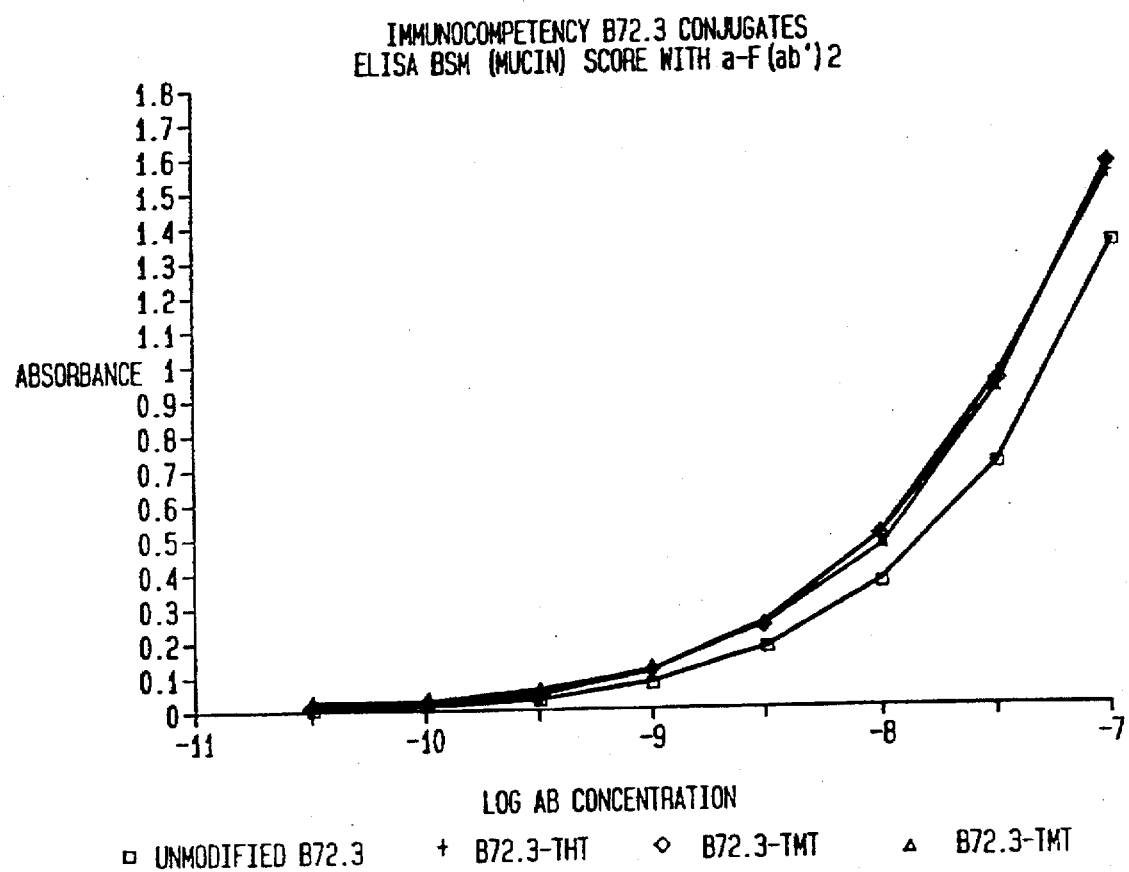
FIG. 2 depicts immunocompetency assays of a B72.3-THT conjugate, two preparations of B72.3-TMT conjugates and unmodified B72.3.

When tested by this procedure, the immunoconjugates of B72.3 with TMT or THT were found to have immunoreactivity comparable to native B72.3. The data are presented in FIGS. 1 and 2. FIG. 1 also contains the curve for a scandium complex of the B72.3-THT conjugate prepared in the same manner as the Europium complex described hereinbefore.

EXAMPLES 1–2

Preparation and Evaluation of Radioactive Immunoreagents (Antibody-TMT Conjugate) Labelled with Radionuclides ($^{111}In^{90}Y$), Using as a Comparative Control, of a DTPA Conjugate A. In Vivo Functional Test of Chelate-Antibody Conjugates-Biodistribution Experiments 1. Test Materials. The immunoconjugates tested were a B72.3-TMT conjugate prepared as described above or a B72.3-DTPA conjugate in which the DTPA was attached (through a linker arm) to oxidized carbohydrate on the antibody using procedures similar to those described for TMT attachment.

2. Labeling Conjugates with Radioisotopes. The antibody-chelate conjugates to be labeled with either $^{111}In$ or $^{90}Y$ were in phosphate buffered saline, pH 6.0. The radionuclides (about 1 mCi) were added to the conjugate solution (1 mL containing about 1 mg of antibody-chelate Conjugate), mixed, and incubated about 30 min at room temperature. Any non-chelated metal was removed from each conjugate preparation by HPLC gel filtration (TSK3000SW column). The column effluent was monitored for both protein (OD280 nm) and radioactivity (radioactivity monitor). The specific activity of the purified labeled conjugates was calculated from this data. The conjugates were used for biodistribution studies immediately.

3. General Procedure. Five mice were used in each test group for the $^{90}$Y biodistribution study and 3 mice in each group for the $^{111}$In study. Target doses for each mouse were 10 mg of radioactive conjugate per dose, i.e.'s 20–100 µg of antibody per µL, and greater than 50 µCi per dose. Both non-tumor bearing and tumor bearing mice were injected on Day 0.

4. Tumor Growth Initiation. Each nude mouse (nu/nu: Swiss Background, Taconic Farms, Germantown, N.Y.) was injected subcutaneously in the left rear flank with one million LS174T cells in exponential growth phase, in about 0.2 mL of sterile medium or saline from cell culture. The mice were examined for tumor growth until tumors became measurable. Thereafter, tumors were measured to the nearest 0.1 mm across two perpendicular diameters (length×width) using digital calipers until the product of the length times the width was between 50 and 100 square millimeters for all the mice.

5. Injection Protocol. On a desirable day following tumor cell (day 0) inoculation, each mouse was injected with the labeled conjugate. The radiolabeled antibody for each dose was drawn up into a separate 1 cc insulin syringe with a 28G, ½ inch needle for administration. Three 10 µL aliquots of each test material were saved for gamma counting to determine the injected dose.

Each syringe containing test material was numbered in order of administration. Each syringe was weighed and counted in a dose calibrator set to quantitate the radionuclide. This information was recorded. The mice were anesthetized by injecting i.p. 0.15 mL of a sterile solution containing ketamine HCl at 11 mg/mL and xylazine at 3 mg/mL. The test material was injected via the retroorbital venous sinus. Each mouse was counted in the dose calibrator immediately after injection, the syringes were reweighed, recounted and the data recorded.

6. Methods of Evaluation. Each animal was weighed to the nearest 0.1 g on Day 0 and just prior to dissection. Immediately prior to imaging and/or dissection, each animal was counted in the dose calibrator following standard operating procedures. Each carcass was counted after dissection. Immediately prior to dissection, each animal had its tumor measured to the nearest 0.1 mm across two perpendicular diameters (length×width) using digital calipers. A blood sample was collected from each animal into a tared culture tube and then the tube was reweighed. Each animal was sacrificed by cervical dislocation. Organs (lungs, spleen, liver, colon, right kidney, left kidney, tumor, bone marrow, muscle) were dissected and trimmed to remove extraneous tissue and then weighed to the nearest milligram. Radioactivity of the dissected organs was determined by gamma counting.

Figure 3:
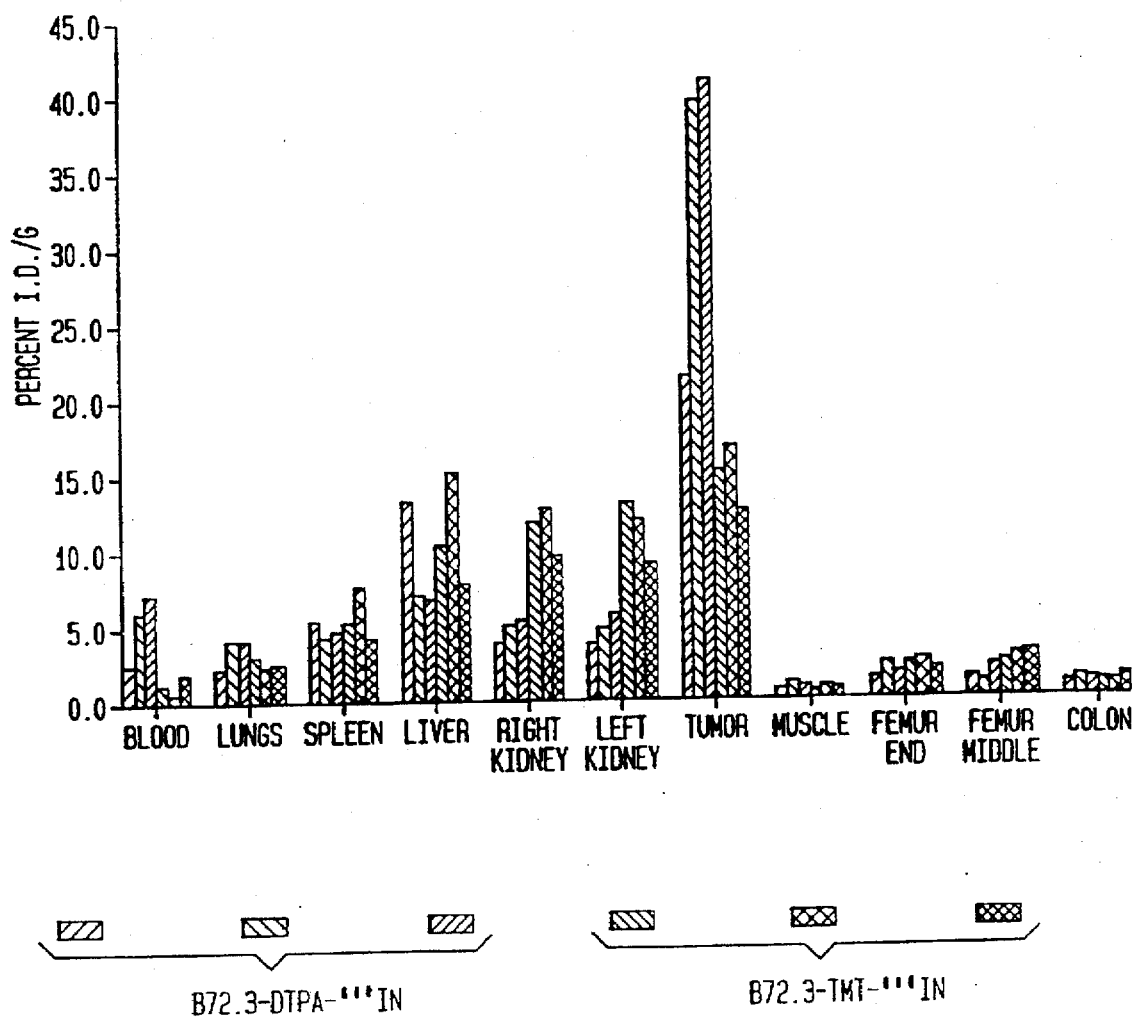

7. Results. The biodistributions shown in FIG. 3 are for six mice four days after injection of the radioactive immunoreagents. The data from the $^{111}$In biodistribution test indicate that the radiolabeled TMT conjugate of B72.3 did target the radioactivity to the tumor. Although liver and kidney levels were slightly greater than the B72.3-DTPA-$^{111}$In conjugate, the B72.3-TMT-$^{111}$In conjugate could be used for $^{111}$In tumor targeting.

Figure 4:
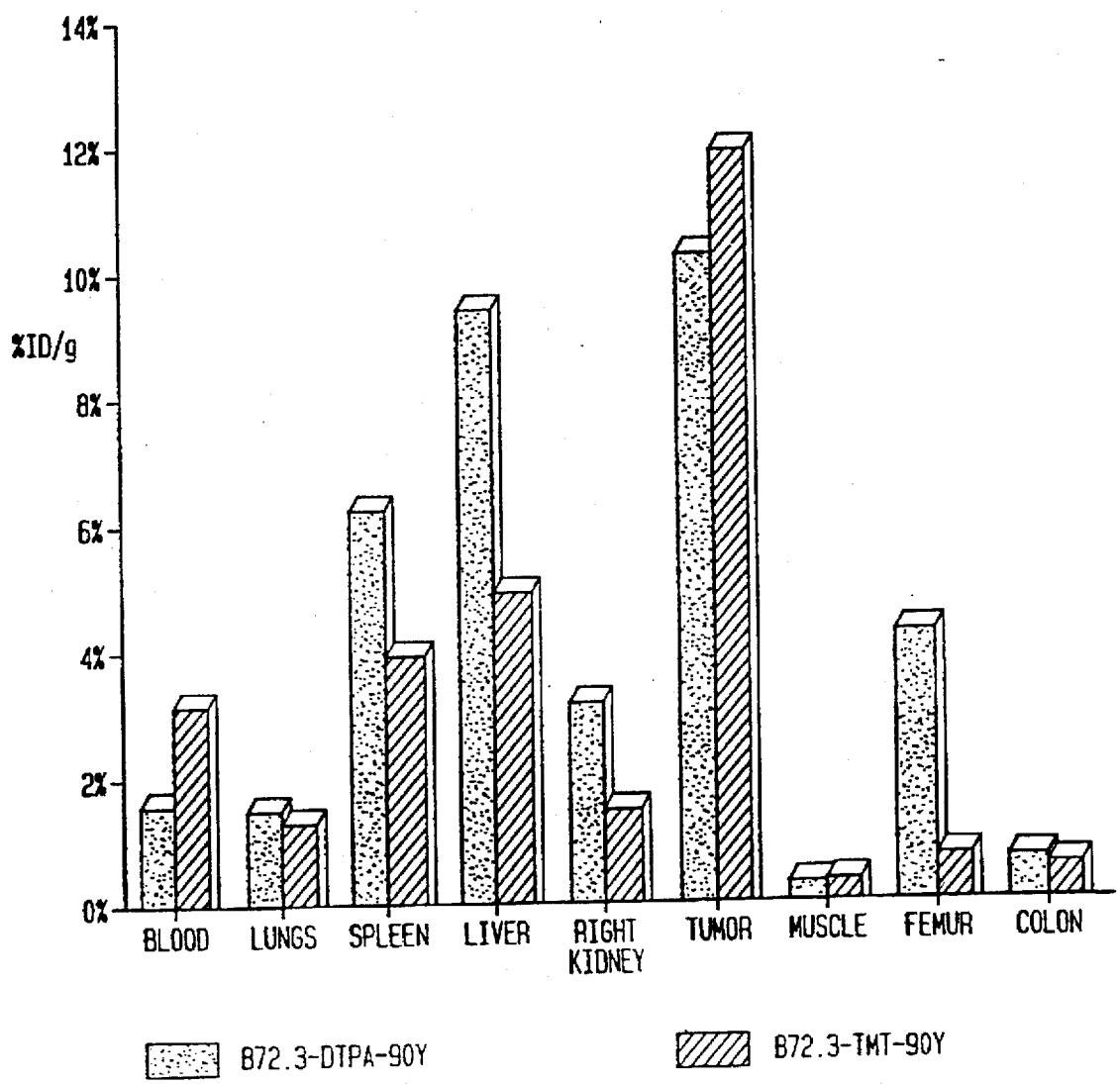
FIG. 4 depicts the results of a biodistribution study of B72.3-TMT-$^{90}$Y, a radioactive immunoreagent of the invention, and B72.3-DTPA-$^{90}$Y.

The biodistrubtions shown in FIG. 4 are those obtained eight days after injection of the radioactive immunoreagent. The average biodistribution value for each group of five mice is graphed for the tissue type examined. The data from the $^{90}$Y biodistribution show that the B72.3-TMT-$^{90}$Y conjugate targeted $^{90}$Y to the tumor as well as the B72.3-DTPA-$^{90}$Y conjugate. However, considerably less $^{90}$Y was found in the femur when the B72.3-TMT-90Y conjugate was used compared to the B72.3-DTPA-$^{90}$Y conjugate. Since the femur (bone marrow) is the dose-limiting organ for $^{90}$Y therapy, this result indicates that TMT is a better chelate for antibody targeted radionuclide therapy using this isotope. Of the other tissues examined, only the blood was found to have a higher $^{90}$Y level when TMT was the chelator used to prepare the immunoconjugate. This is believed to be due to superior in vivo stability of the B72.3-TMT-$^{90}$Y complex compared to the B72.3-DTPA-$^{90}$Y complex.

B. Survival Study

Figure 5:
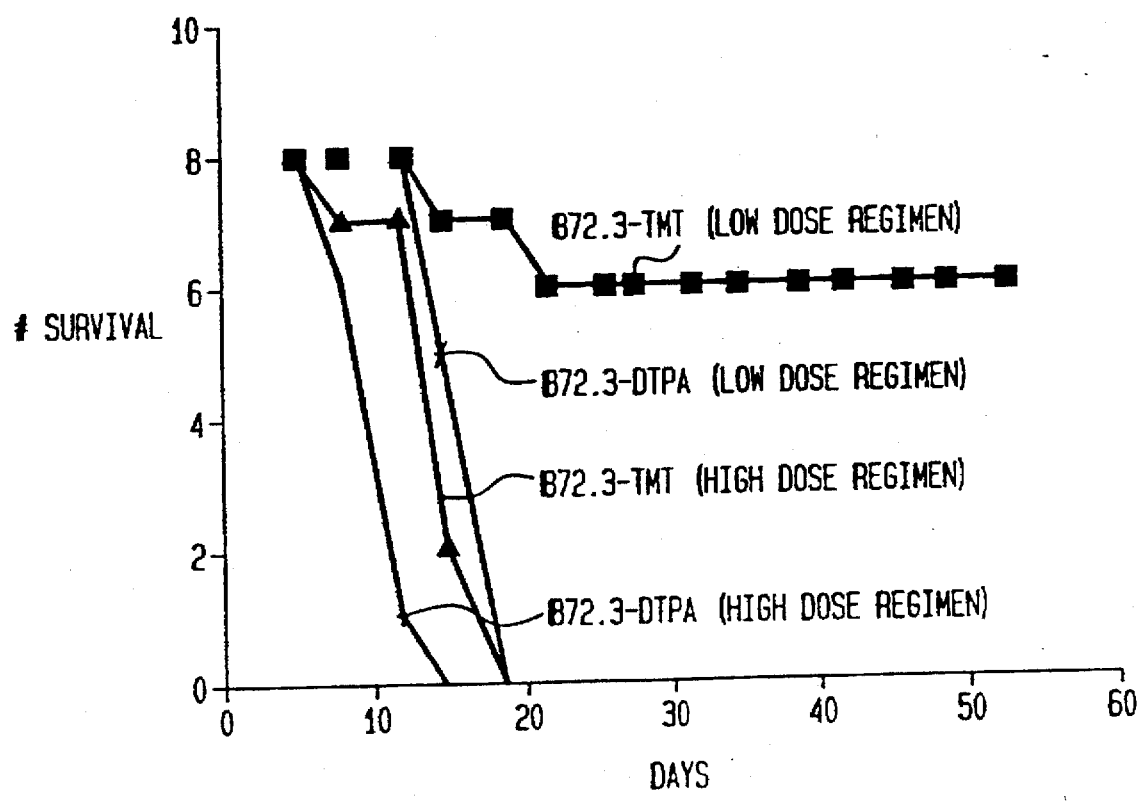
FIG. 5 is a survival curve, i.e., the number of mice surviving each day past the first day of innoculation for a low dose regimen of B72.3-DTPA and a high dose regimen of B72.3-TMT and of B72.3-DTPA.

If the B72.3-TMT-$^{90}$Y complex decreases the amount of $^{90}$Y that gets to the bone marrow compared to B72.3-DTPA-$^{90}$Y and if the bone marrow is the dose-limiting tissue, then mice innoculated with these conjugates should find the B72.3-TMT-$^{90}$Y conjugate less toxic than those innoculated with B72.3-DTPA-$^{90}$Y. The general procedures to test this hypothesis (survival study) were the same as those described for the biodistribution study with the following exceptions. There were 8 tumor bearing nude mice in each test group. The injection schedule was as follows: 200 µCi, 120 µCi, and 120 µCi were given on days 0, 4 and 8, respectively, for both the B72.3-TMT-90Y or B72.3-DTPA-$^{90}$Y conjugate (low dose regimen). Two other sets of mice received 400 µCi, 320 µCi and 320 µCi of the two immunoconjugates on days 0, 4 and 8, respectively (high dose regimen). The survival of the mice was observed (no biodistributions of the test material were performed). Results (FIG. 5) indicate that the survival of the mice was prolonged if $^{90}$Y is administered using the B72.3-TMT conjugate.

C. TMT-Immunoconjugate with anti-tumor specificity

TMT or a suitable derivative thereof can be conjugated to an antibody molecule to yield an antibody-TMT conjugate molecule that displays the ability to bind to a target antigen recognized by the antibody variable region. Such a conjugate molecule can be used to deliver a radioisotope that is chelated by the TMT moiety in order to localize and/or treat the lesion that is targeted by such an immunoconjugate. In one preferred embodiment, the antibody is selected such that it has a broad reactivity with an antigen molecule expressed on tumor cells, thereby providing an antibody-TMT conjugate that can deliver radioisotope to the tumors for therapeutic or diagnostic purposes. ING-1 is a chimeric antibody (described in International Patent Publication Number WO 90/02569, dated 22 March 1990) consisting of a murine variable region and a human immunoglobulin constant region. The antibody molecule is produced by culturing a mouse myeloma cell line expressing the chimeric antibody essentially as described in the above-referenced publication. The chimeric ING-1 antibody is used at a concentration of 5.2 mg/mL in 50 mM sodium acetate buffer at pH 5.6 and supplemented with 150 mM NaCl To 1.15 mL of antibody solution is added a solution of 50 mM sodium borate at pH 9.0 supplemented with 100 mM sodium chloride to a final total volume of 2.5 mL. The solution is applied to a PD-10 chromatography column equilibrated with the sodium borate buffer added to the antibody solution. The antibody is eluted off the column with 3.5 mL of the same sodium borate buffer. The eluate is concentrated using a Centricon-30 ultrafiltration device to a concentration of approximately 4.0 mg ING-1 chimeric antibody per milliliter solution. The solution of the NCS derivative of TMT (from preparation 6, designated herein after as TMT-NCS) is prepared in the sodium borate buffer at a concentration of 10 mg/mL and added to the antibody solution to a final concentration of 138 µM of TMT-NCS. The solution is gently mixed and incubated in the dark at ambient temperature (approx. 22° C.) overnight (approx. 12 hr). The ING-1:TMT conjugate is separated from free TMT-NCS and other low molecular weight products using a Superose 12 HPLC column equilibrated and eluted in 50 mM sodium acetate buffer at pH 5.6 supplemented with 150 mM sodium chloride. The TMT immunoconjugate is then tested for its ability to bind to the tumor cell antigen and also to bind Yttrium-90 isotope to demonstrate that the conjugate can be radiolabeled in the TMT moiety and can target the tumor cell.

EXAMPLE 3

Preparation of a Conjugate of ING-1 with TMT

The antibody ING-1 was produced as above. After purification, ING-1 was used at a concentration of 5.0 mg/mL in 50 mM sodium acetate and 150 mM sodium chloride buffer, pH 5.6.

The conjugation of ING-1 to TMT-NCS was achieved by first adding 1.0M carbonate, 150 mM sodium chloride buffer, pH 9.3 to ING-1 until the antibody solution reaches a pH of 9.0. A sample of that ING-1 solution containing 5 mg of then pipetted into an acid washed, conical, glass reaction vial. A solution of TMT-NCS (Preparation 6) was prepared by dissolving 100 mg in 10 mL of 1.0M carbonate, 150 mM sodium chloride buffer, pH9.3. The conjugation reaction was started by the addition of 96.5 µL of the TMT-NCS solution to the antibody solution to give a 4-fold molar excess of TMT-NCS over ING-1. The solution was stirred briefly to mix the reactants and then left was in the dark at room temperature. After 16 hours, the ING-1 conjugate with TMT was separated from unconjugated TMT by applying the reaction mixture to a PD10 chromatography column which had been pre-washed and equilibriated with 50 mM sodium acetate in 150 mM sodium chloride buffer, pH 5.6. The pure conjugate was eluted off the column with 3.5 mL of that same buffer.

Analysis of Chelator to Antibody Ratio

The concentrations of ING-1 in the conjugate solutions were determined by the BioRad protein assay using bovine immunoglobulin as the protein standard.

In order to calculate the number of functional TMT molecules per antibody, the ING-1 conjugate with TMT (ING-1/TMT) was reacted with a solution of europium chloride until saturation of the metal-binding capacity of the TMT occurred. A 0.5 mg aliquot of the ING-1/TMT in 2.5 mL in 0.05M Tris HCl buffer, pH 7.5, was pipetted into a 5 mL quartz cuvette. A 20 µM europium chloride (europium chloride hexahydrate: Aldrich) solution in 0.05M Tris HCl buffer, pH 7.5, was prepared. An aliquot (50 µL) of this europium chloride solution was added to the cuvette containing ING-1/TMT, and the resulting solution was slowly stirred on a magnetic stirrer at room temperature for 10 min using a small magnetic stir bar placed in the cuvette. The fluorescence of the metal-ING-1/TMT complex was determined in a Perkin Elmer LS 50 spectrofluorometer using an excitation wavelength of 340 nm (10 nm slit width). The fluorescent emission was monitored at 618 nm using a 10 nm slit width and a 430 nm cutoff filter. The above procedure was repeated and fluorescent readings were made after each addition. Aliquots of europium chloride were added until the increase in fluorescence intensity was less than 5% of the preceding reading. A dilution correction was applied to the fluorescence intensity measured at each mole ratio to compensate for the change in volume of the test solution. As each chelating site on the ING-1/TMT conjugate binds one europium ion, and as a europium ion has to be in a chelate site for fluorescence to occur, this method allows the number of functional chelation sites to be quantitated.

Using this method, the ratio of TMT molecules per molecule of antibody was in the range 1:1 to 2:1.

ING-1/TMT Immunoreactiviy assay.

a) By ELISA

The antigen to which the antibody, ING-1, binds was prepared from LS174T or HT 29 cells (available from ATTC) by scraping confluent monolayers of cells from the walls of culture flasks with a cell scraper. The cells from many flasks were combined and a sample was taken and counted to estimate the total number of cells harvested. At all times the cells were kept on ice. Following centrifugation of the cells at 1500 rpm for 10 minutes at 4° C., the cells were washed once in ice-cold 50 mM sodium phosphate buffer, pH 7.4 supplemented with 150 mM sodium chloride (PBS), pelleted under the same conditions and transfered to an ice-cold glass mortar. The cells were homogenized at 4° C. using a motor-driven pestle and then centrifuged at 3000×g for 5 minutes. The antigen-rich supernatant was removed from the other cell debris and subjected to further centrifugation at 100,000×g for one hour at 4° C. The pellet (antigen fraction) from this final step was suspended in 100 µL of PBS for every million cells harvested. Following an estimate of the protein concentration (BioRad BCA protein assay using bovine immunoglobulin as the protein standard) the antigen was stored at at −20° C. until use.

Each well of a 96-well Costar microtiter plates was coated with antigen by adding 100 µL/well of cell lysate (10 µg/mL) prepared as described above. The microtitre plates were allowed to dry overnight in a 37° C. incubator. After washing the plate five times with 0.05% Tween-20 (Sigma), the wells were blocked by adding 125 µL/well of a 1% BSA (bovine serum albumin, Sigma A-7906) solution in PBS and incubated for 1 h at room temperature. The plates were washed five times with 0.05% Tween-20. Samples (50 µL/well in duplicate) of ING-1/TMT conjugates and standard ING-1 antibody solutions were prepared at a range of concentrations in PBS. Biotinylated ING-1 (1.0 µg/mL in 0.1% BSA) was added to each well (50µL/well) and the plates were then incubated for 2 hours at room temperature. Following five washes with 0.05% Tween-20, the plates were blotted dry and incubated at room temperature for one hour with diluted (1:4000 in 0.1% BSA) streptavidin-alkaline phosphatase (Tago; #6567). After a further five washes, color was developed in each well upon the addition of 100 µL per well of phosphatase substrate reagent (two Sigma 104 phosphatase tablets dissolved in 10 mL distilled water and 20 µL Sigma 221 alkaline buffer). After one hour at room temperature, the color was read using a 405 nm filter in a Titertek Multiscan microplate reader.

When tested by this procedure, the immunoconjugates of ING-1 with TMT were found to have immunoreactivity comparable to native ING-1.

ING-1/TMT Immunoreactivity assay.

b) By Flow Cytometry

Target HT29 cells were grown to confluency in tissue culture flasks using DMEM media supplemented with 10% fetal calf serum. The cells were harvested by scraping the flask walls with a cell scraper. Cells from many separate flasks were pooled, centrifuged to a pellet, resuspended at 5×10$^5$/mL in a solution of ice-cold 50 mM sodium phosphate with 150 mM sodium chloride buffer pH 7.4 (PBS)

supplemented with 0.1% bovine serum albumin (Sigma) and 0.02% sodium azide (Flow buffer). The cells were washed in this same buffer and then counted. An antibody standard curve was constructed by diluting ING-1 with an irrelevant (non binding), isotype-matched control antibody (human IgG1) to give a number of samples ranging in ING-1 content from 10% to 100%. The standard curve was made in flow buffer so that each sample contained 1.0 μg protein per mL. Samples from the standard curve and unknowns were then incubated with $5 \times 10^5$ HT29 cells at 4° C. for 1 hour. After extensive washing to remove unbound antibody, the cells were resuspended in 100 μL flow buffer and incubated at 4° C. for 1 hour with goat-anti-human antibody labelled with fluorescene isothiocyanate (FITC). After further washing in flow buffer the samples were analyzed by flow cytometry on a Coulter EPICS 753 flow cytometer. Fluorescene isothiocyanate (FITC) and propidium iodide (PI) were excited using the 488 nm emission line of an argon laser. The output is set at 500 mw in light regulation mode. Single cells were identified by 90 degree and forward angle light scatter. Analysis windows were applied to these parameters to separate single cells from aggregates and cell debris. Fluorescence from FITC and propidium were separated with a 550 nm long pass dichroic filter and collected through a 530 nm band pass filter (for FITC), and a 635 nm band pass filter (for PI). Light scatter parameters were collected as integrated pulses and fluorescence was collected as log integrated pulses. Dead cells were excluded from the assay by placing an analysis window on cells negative for PI uptake. The mean fluorescence per sample (weighted average from 2500 cells) was calculated for each histogram. FITC calibration beads were analysed in each experiment to establish a standard curve. The average fluorescence intensity for each sample was then expressed as the average FITC equivalents per cell. Immunoreactivity was calculated by comparing the average fluorescence intensity of the unknown sample with values from the standard curve. Samples of ING-1/TMT had immunoreactivity values comparable to the native ING-1 antibody by this method.

Determination of aggregate formation by size-exclusion HPLC.

A 30 cm×7.5 mm TSK-G3000SW size-exclusion HPLC column (Supelco) fitted with a guard column of the same material was equilibrated with 12 column volumes of 10 mM sodium phosphate buffer pH 6.0 supplemented with 150 mM sodium chloride using a Waters 600E HPLC system with a flow rate of 1.0 mL per minute at 400–600 PSI. A sample (25 μL) of BioRad gel filtration protein standards was injected onto the column. The retention time of each standard was monitored by a Waters 490 UV detector set at 280 nm. Following the recovery of the final standard from the column, it was washed with a further 10 volumes of 10 mM sodium phosphate buffer pH 6.0 supplemented with 150 mM sodium chloride. Samples (50 μL) of either native ING-1 antibody or ING-1/TMT were injected onto the column and their retention times recorded. From the areas of the retained peaks and the retention time, the amount of aggregated material in the ING-1/TMT sample was calculated.

By this method the native ING-1 antibody had a retention time of 9.1 minutes. ING-1/TMT had a major peak also at 9.1 minutes but a minor peak, attributable to aggregates, was sometimes seen at 7.3 minutes. By comparison of the peak areas, the aggregate peak was less than 5% of the total.

Radiolabeling of ING-1/TMT with $^{90}$Y.

A volume of radioactive yttrium chloride ($^{90}$Y in 0.04M hydrochloric acid at a specific activity of >500 Ci/g: Amersham-Mediphysics) was neutralized using two volumes of 0.5M sodium acetate pH 6.0. The neutralized $^{90}$Y (1.0 mCi) was added to 1.0 mL of ING-1/TMT (1 mg/mL) in 50 mM sodium acetate buffer containing 150 mM sodium chloride at pH 5.6. The labelling was allowed to proceed for one hour and then the reaction mixture was loaded onto a PD-10 chromatography column which had been pre-washed and equilibrated in a buffer containing 50 mM sodium phosphate with 150 mM sodium chloride pH 7.4 (PBS). The sample was eluted from the column with 1.5 mL of PBS. Fractions of radiolabeled ING-1/TMT (0.5 mL) were collected, assayed for radioactivity, and pooled. The labeling efficiency was determined by removing 1.0 μL of the sample and spotting it on to a Gelman ITLC-SG strip. The strip was developed in a glass beaker containing 0.1M sodium citrate, pH 6.0 for a few minutes until the solvent front had reached three-quaters of the way to the top of the paper. The strip was inserted into a System 200 Imaging Scanner (Bioscan) which had been optimized for $^{90}$Y and which was controlled by a Compaq 386/20e computer. In this system free $^{90}$Y migrates at the solvent front while the ING-1/TMT ($^{90}$Y) remains at the origin.

Using this system more than 98% of the total $^{90}$Y radioactivity was always found associated with ING-1/TMT.

Labeling ING-1/TMT with fluorescent metals.

Binding of lanthanides such as europium(III) to chelating agents that contain an aromatic moiety held close to the co-ordination sphere can lead to "sensitized" fluorescence wherein light is absorbed through the aromatic system and the energy is transfered to the metal. The metal then produces emissions characterized by a very large Stokes shift and fluorescence lifetimes of up to several seconds. A 0.5 mg aliquot of the ING-1/TMT in 2.5 mL in 0.05M Tris HCl buffer pH 7.5 was pipetted into a 4 mL conical reaction vial containing a small stirring bar. A 250 μM europium chloride (europium chloride hexahydrate: Aldrich) solution in 0.05M Tris HCl buffer pH 7.5 was prepared. An aliquot (50 μL) of this europium chloride solution was added to the reaction vial containing ING-1/TMT, and the resulting solution was stirred very slowly on a magnetic stirrer at room temperature. The labelling was allowed to proceed for one hour and then the reaction mixture was loaded on to a PD-10 chromatography column which had been pre-washed and equilibrated in a buffer containing 10 mM sodium phosphate and 150 mM sodium chloride at pH 6.0 (PBS). The sample was eluted from the column with 3.5 mL of PBS. The fluorescence of a 50 μL sample of the metal-ING-1/TMT complex was determined in a Perkin Elmer LS 50 spectrofluorometer using an excitation wavelength of 340 nm (10 nm slit width). The fluorescent emission was recorded at 618 nm using a 10 nm slit width and a 430 nm cutoff filter. Each functional chelating site on the ING-1/TMT conjugate binds one europium ion. Using this method, between 1 and 3 fluorescent europium ions were bound per molecule of antibody.

EXAMPLE 4

Preparation of a Conjugate of PR1A3 with TMT

PR1A3 is a murine antibody (Developed by ICRF, U.K.) The antibody was used at a concentration of 4.0 mg/mL in 50 mM sodium acetate buffer at pH 5.6 and supplemented with 150 mM NaCl. To 1.0 mg of antibody solution was added a solution of 50 mM sodium borate at pH 9.0 supplemented with 100 mM sodium chloride to a final total volume of 2.5 mL. The solution was applied to a PD-10 chromatography column equilibrated with the sodium borate buffer added to the antibody solution. The antibody was eluted off the column with 3.5 mL of the same sodium borate buffer. The eluate was concentrated using a Centricon-30 ultrafiltration device to a concentration of 5.0 mg of PR1A3 antibody per milliliter solution. A solution of the TMT-NCS (Preparation 6) was prepared in the sodium borate buffer at a concentration of 2.0 mg/mL and added to the antibody solution to a final concentration of 104 µM of TMT-NCS. The solution was gently mixed and incubated in the dark at ambient temperature (approx. 22° C.) overnight (14–16 hr). The PR1A3:TMT conjugate was separated from free TMT-NCS and other low molecular weight products using a Superose 6 HPLC column equilibrated and eluted in 50 mM sodium phosphate buffer at pH 7.2 supplemented with 150 mM sodium chloride. The eluate was concentrated using a Centricon-30 ultrafiltration device to a concentration of 0.25 mg PR1A3:TMT per milliliter solution. The TMT immunoconjugate is then tested for its ability to bind to the tumor cell antigen and also to bind yttrium-90 isotope.

Analytical tests on PR1A3/TMT conjugates.

Analytical tests performed on PR1A3/TMT conjugates were very similar to those outlined above for the testing of ING-1/TMT conjugates. The most notable exception is that SW 1222 cells were used to test the immunoreactivity using flow cytometry. These cells (ATCC) were grown in MEM medium supplemented with 10% fetal calf serum and non-essential amino acids in Earles balanced salt solution. ELISA tests for immunoreactivity were not performed on PR1A3/TMT conjugates.

EXAMPLE 5

Preparation of a Conjugate of NRLU-10 with TMT

NRLU-10 is a murine antibody (Developed by Okabe as TFS-2). The antibody was used at a concentration of 3.4 mg/mL in 50 mM sodium phosphate buffer at pH 7.2 and supplemented with 150 mM NaCl To 12 mg of antibody solution was added 1.5 mL of a solution of 50 mM sodium borate at pH 9.0 supplemented with 150 mM sodium chloride. Two aliquots (2.5 mL each) of that solution were applied to separate PD-10 chromatography columns equilibrated with 50 mM sodium borate at pH 9.0 supplemented with 150 mM sodium chloride. The antibody was eluted off each column with 3.5 mL of the same sodium borate buffer. These eluates were pooled. A solution of the TMT-NCS was prepared in the sodium borate buffer at a concentration of 10 mg/mL and 19 microliters was added to the antibody preparation. The solution was gently mixed and incubated in the dark at ambient temperature (approx. 22° C.) overnight (approx. 12 hr). The NRLU-10:TMT conjugate was separated from free TMT-NCS and other low molecular weight products using a Superose 12 HPLC column equilibrated and eluted in 50 mM sodium phosphate buffer at pH 6.0 supplemented with 150 mM sodium chloride. The TMT immunoconjugate was then tested for its ability to bind to the tumor cell antigen and also to bind yttrium-90 isotope.

Analytical tests on NRLU-10 TMT conjugates.

Analytical tests performed on NRLU-10/TMT conjugates were very similar to those outlined above for the testing of ING-1/TMT conjugates.

EXAMPLE 6

Preparation of an immunoreactivy agent comprising of an oligonucleotide covalently bonded to the complexing agent.

The complexing agent TMT can be covalently linked to an immunoreactive group other than an antibody, for example an oligonucleotide. This immunoreagent can be labelled with $^{90}$y and the radioactive immunoreagent thus prepared can react with its compliment, namely the complimentary oligonucleotide.

Part A.

Preparation of an oligonucleotide, cI

A 20-mer oligonucleotide containing a 3'-amine group, 5'-TTAGCTTCTCCGTCCATAA-$C_5$Amine-T-3', cI, is prepared on an Applied Biosystems DNA synthesizer as directed by the equipment manufacturer using Uni-link Amino Modifier (Clonetech) as the precursor to the 3'-amine group and the 2-deoxynucleotide phosphoramidite reagent precursors 5'-dimethoxytrityl cytidine 3'-O-phosphoramidite, 5'-dimethoxytrityl adenosine-3'-O-phosphoramidite, 5'-dimethoxytrityl guanosine-3'-O-phosphoramidite, and 5'-dimethoxytrityl thymidine-3'-O-phosphoramidite (Applied Biosystems). After deblocking the protecting groups with ammonium hydroxide, the aminefunctionalized oligonucleotide is further purified by elution down an OPEC Cartridge (Polymer RPI) column (Clonetech) with deionized water. The concentration of oligonucleotide is monitored using absorbance at 260 nm.

Part B.

Preparation of an oligonucleotide conjugated to TMT, cI-TMT.

To a 2.5 mM oligonucleotide solution of Part A in 0.033 mM carbonate/bicarbonate buffer at pH 9.0 is added 10 mg of TMT isothiocyanate of Preparation 6. The reaction mixture is vortex mixed and kept at 23° C. for 16 hours. The product is purified by Sephadex G-25 column chromatography, eluting with deionized water.

Part C.

Preparation of a radionuclide labeled oligonucleotide TMT conjugate of Part B A solution of the oligonucleotide TMT conjugate of part B in 0.01 mM sodium acetate buffer at 20° C. is treated with a solution of $^{90}$YCl$_3$ in 0.01M sodium acetate buffer at pH 6.0. Uptake of the radiolabel into the conjugate is demonstrated using thin layer chromatography.

Part D.

Preparation of an oligonucleotide, I, which is complimentary to oligonucleotide cI of Part A A 20-mer oligonucleotide containing a 3'-amine group, 5'-TCT TAT GGA CGG AGA AGC-$C_5$ Amine-T-3, is prepared on an Applied Biosystems DNA synthesizer as in Part A using UniLink Amino Modifier (Clonetech) as the precursor to the 3'-amine group, and 2-deoxynucleotide phosphoramidite reagent precursors 5'-dimethoxytrityl cytidine-3'-O-phosphoramidite, 5'-dimethoxytrityl adenosine-3'-O-phosphoramidite, 5'-dimethoxytrityl guanosine-3'-O-phosphoramidite, and 5'-dimethoxytrityl thymidine-3'-O-phesphoramidite (Applied Biosystems). After deblocking the protecting groups with ammonium hydroxide, the amine-functionalized oligonucleotide is further purified by elution down an OPEC cartridge (Polymer RPI) column (Clonetech) with deionized water. The concentration of oligonucleotide is monitored using absorbunce at 260 nm.

Part E.

Hybridization of cI conjugated to TMT and labelled with $^{90}$Y to the complimentary oligonucleotide, designated I.

To a solution of oligonucleotide I prepared in part D in phosphate buffered saline, pH 7.4, at 4° C. is added a solution of the $^{90}$Y-labeled TMC-cI as described above. After 1 hour, the components of the reaction mixture are analyzed by polyacrylamide gel electrophoresis. The radiolabel is observed at the position in the gel corresponding to the hybridized oligonucleotide.

The invention has been described in detail with particular reference to certain preferred embodiments thereof, but it will be understood that variations and modifications can be effected within the spirit and scope of the invention.

What is claimed is:

1. A targeting radioactive immunoreagent comprising a metal radionuclide ion, a complexing agent, and an immunoreactive group covalently bonded to said complexing agent, said complexing agent having the structure

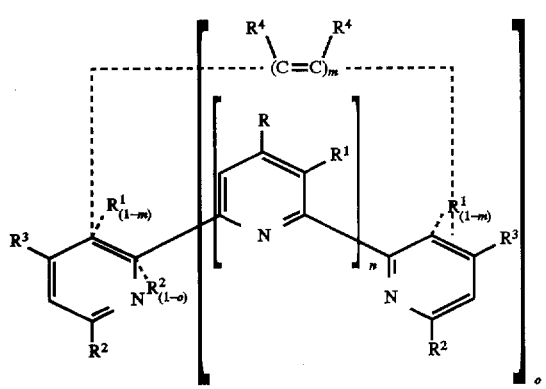

wherein

R is selected from hydrogen, alkyl, alkoxy, alkylthio, alkylamino, alkylformamido, aryl, aryloxy, heterocyclyl and a protein reactive group;

each $R^1$ is independently selected from hydrogen, alkyl, alkoxy, alkylthio, alkylamino, alkylformamido, aryl, aryloxy, heterocyclyl and a protein reactive group, wherein each alkyl and alkylene moiety contains 1 to 20 carbon atoms, each aryl or arylene moiety contains 6-20 carbon atoms, and each heterocyclyl group contains at least 1, 5 or 6 membered ring and a heteroatom selected from the group consisting of N, S, P and O;

each $R^2$ is independently selected from hydroxy, carboxy, hydroxyalkyl, carbonyliminodiacetic acid, methyleneiminodiacetic acid, methylenethioethyleneiminodiacetic acid, hydrazinylidenediacetic acid, and a salt of such acids, or the two $R^2$ groups, taken together, represent the atoms necessary to complete a macrocyclic ring structure containing at least one heteroatom coordinating site and at least one alkylene group forming part of the ring structure;

each $R^3$ is independently selected from hydrogen, alkyl, alkoxy, alkylthio, alkylamino, alkylformamido, aryl, aryloxy, heterocyclyl and a protein reactive group;

each $R^4$ is independently selected from hydrogen and a protein reactive group;

n is 0, 1, 2, 3, or 4;

o is 0 or 1;

m is 0 or 1;

provided that at least one of n and m is 0 and at least one of R, $R^1$, $R^3$ and $R^4$ is a protein reactive group.

2. The immunoreagent of claim 1 wherein the complexing agent has the structure:

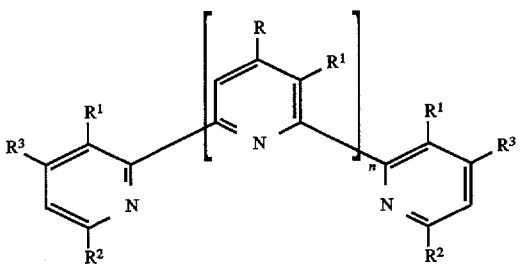

wherein R, $R^1$, $R^2$ and $R^3$ are as defined in claim 1 and n is 0, 1, 2, 3 or 4.

3. The immunoreagent of claim 2 wherein n is 1, 2, 3, or 4 and R is

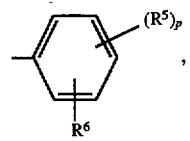

wherein $R^5$ is alkoxy or alkyl, p is 0, 1, 2, 3 or 4 and $R^6$ is a protein reactive group.

4. The immunoreagent of claim 3 wherein n is 1.

5. The immunoreagent of claim 3 wherein $R^6$ is selected from the group consisting of amino, alkylamino, arylamino, semicarbazido, thiocarbazido, thiosemicarbazido, isocyanato and isothiocyanato, vinyl sulfonylalkyloxy, vinyl sulfonylalkyl(polyoxyalkyl)oxy, amidatoalkyloxy, hydrazidoalkyloxy, azidocarbonylalkyloxy, aryloxycarbonyloxyalkyloxy, aryloxycarbonyl (polyoxyalkyl)oxy, 4,6-dichloro-2-triazinyloxy, dichlorotriazinyl(polyoxyalkyl)oxy, 4-alkoxy-6-chloro-2-triazinyloxy, 4-alkoxy-6-chloro-2-triazinyl(polyoxyalkyl) oxy, formylalkyl, aminoalkyl, thioalkyimidoaminoalkyloxy, thioalkylcarbonylaminoalkyloxy, maleimidoalkylcarbonylaminoalkyloxy, azido, 4,6-dichloro-2-triazinylamino, iodoalkylcarbonylamino, amidatoalkylamino, and amidatoarylalkylamino.

6. The immunoreagent of claim 3 wherein $R^6$ is selected from the group consisting of amino, isothiocyanato and thiosemicarbazido.

7. The immunoreagent of claim 3 wherein said complexing agent is 4'-(3-amino-4-methoxy-phenyl)-6,6"-bis[N,N-di-(carboxymethyl)aminomethyl]-2,2':6',2"-terpyridine tetrasodium salt or 4'-(3-amino-4-methoxyphenyl)-6,6"-bis(N', N'-dicarboxymethyl-N-methylhydrazino)-2,2':6'2"-terpyridine tetrasodium salt.

8. The immunoreagent of claim 1 wherein the complexing agent has the structure:

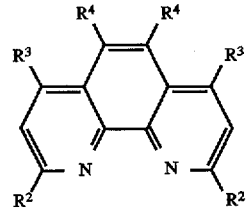

wherein $R^2$, $R^3$ and $R^4$ are as defined in claim 1.

9. The immunoreagent of claim 8 wherein at least one $R^4$ is selected from the group consisting of amino, isothiocyanato and thiosemicarbazido, vinyl sulfonylalkyloxy, vinyl sulfonylalkyl(polyoxyalkyl)oxy, amidatoalkyloxy, hydrazidoalkyloxy, azidocarbonylalkyloxy, aryloxycarbonyloxyalkyloxy, aryloxycarbonyl (polyoxyalkyl)oxy, 4,6-dichloro-2-triazinyloxy, dichlorotriazinyl(polyoxyalkyl)oxy, 4-alkoxy-6-chloro-2-triazinyloxy, 4-alkoxy-6-chloro-2-triazinyl(polyoxyalkyl)oxy, formylalkyl, aminoalkyl, thioalkyimidoaminoalkyloxy, thioalkylcarbonylaminoalkyloxy, maleimidoalkylcarbonylaminoalkyloxy, azido, 4,6-dichloro-2-triazinylamino, iodoalkylcarbonylamino, amidatoalkylamino, and amidatoarylalkylamino.

10. The immunoreagent of claim 1 wherein said protein reactive group is selected from the group consisting of amino; alkylamino; arylamino; hydrazino; alkylhydrazino; arylhydrazino; carbazido; semicarbazido; thiocarbazido; thiosemicarbazido; sulfhydryl; sulfhydrylalkyl; sulfhydrylaryl; hydroxy; carboxy; carboxyalkyl and carboxyaryl; active halogen containing groups, 2-leaving group-substituted ethylsulfonyl and ethylcarbonyl; vinylsulfonyl; vinylcarbonyl; epoxy; isocyanato; isothiocyanato; aldehyde; aziridine; succinimidoxycarbonyl; activated acyl groups; mixed anhydrides; and groups that can be linked to protein or modified protein by use of a crosslinking agent.

11. The immunoreagent of claim 1, wherein said protein reactive group is selected from the group consisting of amino, isocyanato, isothiocyanato, carbazido, semicarbazido, thiocarbazido and thiosemicarbazido, vinyl sulfonylalkyloxy, vinyl sulfonylalkyl(polyoxyalkyl)oxy, amidatoalkyloxy, hydrazidoalkyloxy, azidocarbonylalkyloxy, aryloxycarbonyloxyalkyloxy, aryloxycarbonyl(polyoxyalkyl)oxy, 4,6-dichloro-2-triazinyloxy, dichlorotriazinyl(polyoxyalkyl)oxy, 4-alkoxy-6-chloro-2-triazinyloxy, 4-alkoxy-6-chloro-2-triazinyl(polyoxyalkyl)oxy, formylalkyl, aminoalkyl, thioalkyimidoaminoalkyloxy, thioalkylcarbonylaminoalkyloxy, maleimidoalkylcarbonylaminoalkyloxy, azido, 4,6-dichloro-2-triazinylamino, iodoalkylcarbonylamino, amidatoalkylamino, and amidatoarylalkylamino.

12. The immunoreagent of claim 1, wherein said immunoreactive group is selected from the group consisting of enzymes, amino acids, peptides, polypeptides, proteins, lipoproteins, glycoproteins, hormones, drugs, steroids, vitamins, polysaccharides, pharmaceuticals, haptens, lectins, toxins, nucleic acids, oligonucleotides, antibodies, antibody fragments, antigenic materials, avidin and biotin.

13. The immunoreagent of claim 1, wherein said immunoreactive group is an antibody.

14. The immunoreagent of claim 12, wherein said immunoreactive group is a protein.

15. The immunoreagent of claim 1, wherein said radionuclide ion is selected from the group consisting of Sc, Fe, Pb, Ga, Y, Bi, Lu, Mn, Cu, Cr, Zn, Ge, Mo, Tc, Ru, In, Sn, Sm, Sb, W, Re, Po, Ta and Tl ions.

16. The immunoreagent claim 15 wherein said radionuclide ion is selected from the group consisting of $^{111}In^{+++}$, $^{212}Pb^{++}$, $^{68}Ga^{++}$, $^{90}Y^{+++}$ and $^{212}Bi^{+++}$ ions.

17. The immunoreagent of claim 1, wherein R is a 4-alkoxy-3-aminophenyl or 4-alkoxy-3-isothiocyanatophenyl group.

18. The immunoreagent of claim 1 wherein each $R^2$ is methyleneiminodiacetic acid or a salt thereof.

19. The immunoreagent of claim 1 wherein each $R^3$ is H.

20. The immunoreagent of claim 1 wherein $R^4$ is amino or isothiocyanato.

21. The immunoreagent of claim 15 wherein said metal radionuclide ion is $^{90}Y^{+++}$.

22. The immunoreagent of claim 13 wherein said antibody is selected from the group consisting of B72.3, 9.2.27, D612, UJ13A, NRLU-10, 7E11C$_5$, CC49, TNT, PR1A3, ING-1, B174 and B43 antibodies.

23. The immunoreagent of claim 22 wherein said antibody is selected from B72.3 and ING-1 antibodies.

24. The immunoreagent of claim 22 wherein said metal radionuclide ion is $^{90}Y^{+++}$.

25. The immunoreagent of claim 1 selected from the group consisting of B72.3-TMT-$^{90}$Y, ING-1-TMT-$^{90}$Y, ING-1-THT-$^{111}$In, B72.3-TMT-$^{111}$In, B72.3-THT-$^{90}$Y, and B72.3-THT-$^{111}$In.

26. A diagnostic imaging composition comprising the radioactive immunoreagent of claim 1.

27. A therapeutic composition comprising the radioactive immunoreagent of claim 1 and a pharmaceutically acceptable carrier therefor.

* * * * *